(12) United States Patent
Thomas et al.

(10) Patent No.: US 7,807,704 B2
(45) Date of Patent: Oct. 5, 2010

(54) BICYCLIC, NITROGEN-CONTAINING COMPOUNDS MODULATING CXCR4 AND/OR CCXCKR2

(75) Inventors: William D. Thomas, San Jose, CA (US); Manmohan Reddy Leleti, Sunnyvale, CA (US); Andrew M. K. Pennell, San Francisco, CA (US)

(73) Assignee: Chemocentryx, Inc., Mountain View, CA (US)

( * ) Notice: Subject to any disclaimer, the term of this patent is extended or adjusted under 35 U.S.C. 154(b) by 72 days.

(21) Appl. No.: 11/731,695

(22) Filed: Mar. 30, 2007

(65) Prior Publication Data

US 2007/0275965 A1    Nov. 29, 2007

Related U.S. Application Data

(60) Provisional application No. 60/787,925, filed on Mar. 30, 2006.

(51) Int. Cl.
*A01N 43/38* (2006.01)
*A61K 31/40* (2006.01)
*C09B 5/00* (2006.01)

(52) U.S. Cl. ...................................... 514/412; 548/416
(58) Field of Classification Search ........................ None
See application file for complete search history.

(56) References Cited

U.S. PATENT DOCUMENTS

| 5,612,360 | A | 3/1997 | Boyd et al. |
| 6,864,265 | B2 | 3/2005 | Bridger et al. |
| 2003/0148940 | A1 | 8/2003 | Tudan et al. |
| 2003/0232818 | A1 | 12/2003 | Anderson et al. |
| 2005/0002939 | A1 | 1/2005 | Zlotnik et al. |

FOREIGN PATENT DOCUMENTS

| WO | WO 9403483 | * | 2/1994 |
| WO | WO 99/56765 | A1 | 11/1999 |
| WO | WO 2005/000333 | A1 | 1/2006 |
| WO | WO 2007/115232 | A2 | 10/2007 |
| WO | WO 2007/115232 | A3 | 10/2007 |

OTHER PUBLICATIONS

Nicolaou et al.; "The CP Molecule Labyrinth: A Paradigm of How Endeavors in Total Synthesis Lead to Discoveries and Inventions in Organic Synthesis"; 2002; Angew. Chem. Int. Ed.; 41: 2678-2720.*
Yang. Tetrahedron Letters, 2000, 41, 6981-84.*
Busillo, J.M. et al., "Regulation of CXCR4 Signaling," *Biochimica et Biophysica Acta*, Nov. 10, 2006, vol. 1768, pp. 952-963.
Dairaghi, D.J. et al., "Chemokine Receptor CCR3 Function is Highly Dependent on Local pH and Ionic Strength," *The Journal of Biological Chemistry*, Nov. 7, 1997, vol. 272, No. 45, pp. 28206-28209.
Dairaghi, D.J. et al., "HHV8-Encoded vMIP-I Selectively Engages Chemokine Receptor GCR8. Agonist and antagonist Profiles of Viral Chemokines," *The Journal of Biological Chemistry*, Jul. 30, 1999, vol. 274, No. 31, pp. 21569-21574.
Gosling, J. et al., "Cutting Edge: Identification of a Novel Chemokine Receptor That Binds Dendritic Cell- and T Cell-Active Chemokines Including ELC, SLC, and TECK," *J. Immunol.*, Mar. 15, 2000, vol. 164, No. 6, pp. 2851-2856.
Paluchowska, M.H. et al., "Structure Activity Relationship Studies of CNS Agents. Effect of the Amide Fragment on 5-HT$_{1A}$ Receptor Activity of Some Analogs of MP 3022," *Polish Journal of Medicinal Chemistry*, 1999, vol. 51, No. 5, pp. 415-421.
Penfold, M.E.T. et al., "Cytomegalovirus Encodes a Potent α Chemokine," *Proc. Natl. Acad. Sci. USA*, Aug. 1999, vol. 96, pp. 9839-9844.

* cited by examiner

*Primary Examiner*—James O Wilson
*Assistant Examiner*—Noble Jarrell
(74) *Attorney, Agent, or Firm*—Townsend and Townsend and Crew LLP

(57) ABSTRACT

The present invention is directed to novel compounds and pharmaceutical compositions that inhibit the binding of the SDF-1 chemokine to the chemokine receptor CXCR4 and/or the binding of the SDF-1 or I-TAC chemokines to the chemokine receptor CCXCKR2 (CXCR7). These compounds are useful in preventing tumor cell proliferation, tumor formation, metastasis, inflammatory diseases, treatment of HIV infectivity, treatment of stem cell differentiation and mobilization disorders, and ocular disorders.

18 Claims, 4 Drawing Sheets

BICYCLIC, NITROGEN-CONTAINING COMPOUNDS MODULATING CXCR4 AND/OR CCXCKR2

CROSS-REFERENCES TO RELATED APPLICATIONS

This application claims priority to provisional U.S. application No. 60/787,925, filed on Mar. 30, 2006 which is incorporated herein by reference for all purposes.

STATEMENT AS TO RIGHTS TO INVENTIONS MADE UNDER FEDERALLY SPONSORED RESEARCH AND DEVELOPMENT

Federally sponsored research or development money from Grant No. U19 AIO56690 from the National Institute of Allergy and Infectious Diseases was used in the development of this invention. The government may have rights to aspects of the invention.

REFERENCE TO A "SEQUENCE LISTING," A TABLE, OR A COMPUTER PROGRAM LISTING APPENDIX SUBMITTED ON A COMPACT DISK

BACKGROUND OF THE INVENTION

Chemokines are a superfamily of small, cytokine-like proteins that induce cytoskeletal rearrangement, firm adhesion to endothelial cells, and directional migration, and may also effect cell activation and proliferation. Chemokines act in a coordinated fashion with cell surface proteins to direct the specific homing of various subsets of cells to specific anatomical sites. Chemokines are thought to mediate their effect by binding to seven-transmembrane G protein-coupled receptors to attract leukocyte subsets to sites of inflammation, and are generally thought to play an important role in the initiation and maintenance of inflammation (Baglionini et al. (1998) Nature 392: 565-568); Luster, A. D., New Eng. J. Med., (1998) 338(7), 436).

Stromal cell derived factor one (SDF-1) is a member of the CXC family of chemokines. SDF-1 has two isoforms (SDF-1α and SDF-1β); Genbank accession numbers L36033 and L36034, respectively), which are closely related, and is referred to herein collectively as SDF-1. SDF-1 is the natural ligand for the chemokine receptor CXCR4. CXCR4 receptor was originally cloned by Loetscher et al. (see, Loetscher, M., et al. J. Biol. Chem. (1994) 269, 232) and is found to be expressed on neutrophils, monocytes, myeloid cells and T lymphocytes (see, Murdoch, C., et al. Blood, (2000) 95(10), 3032).

CXCR4 has been found to be the major co-receptor for T-tropic HIV-1 entry, i.e., it interacts with HIV and with the cellular CD4 receptor to facilitate viral entry into cells (See, Feng, Y., et al. Science (1996) 272, 872). In addition to functioning as a HIV entry co-receptor, the CXCR4 receptor plays a role in many cell signaling processes. The importance of the signaling mechanism between the CXCR4 natural ligand, pre-B-cell growth-stimulating factor/stromal cell derived factor (PBSF/SDF-1) to the CXCR4 chemokine receptor has been described by researchers. CXCR4 receptor has been found to be essential for the vascularization of the gastrointestinal tract (Tachibana, et al., Nature (1998) 393:591-594) as well as haematopoiesis and cerebellar development (Zou, et al., Nature (1998) 393:591-594). Interference with any of these important functions served by the binding of pre-B-cell growth-stimulating factor/stromal derived factor (PBSF/SDF-1) to the CXCR4 chemokine receptor results in lethal deficiencies in vascular development, haematopoiesis and cardiogenesis.

SDF-1 is functionally distinct from other chemokines in that it is reported to have a fundamental role in the trafficking, export and homing of bone marrow progenitor cells (See, Hattori, K., et al. Blood (2000) 97, 3354-3360; WO 2005/000333). It has been reported that CXCR4-deficient mice display hematopoietic defects (Nagasawa et al. Nature (1996) 382, 635-638). The migration of CXCR4 expressing leukocytes and hematopoietic progenitors to SDF-1 appears to be important for maintaining B-cell lineage and localization of CD34+ progenitor cells in bone marrow (see, Bleul et al. J. Exp. Med. (1998) 187, 753-762; Viardot et al. Ann. Hematol. (1998) 77, 195-197; Auiti et al. J. Exp. Med. (1997) 185, 111-120; Peled et al. Science (1999) 283, 845-848; Qing et al. Immunity (1999) 10, 463-471; Lataillade et al. Blood (1999) 95, 756-768; Ishii et al. J. Immunol. (1999) 163, 3612-3620; Maekawa et al. Internal Medicine (2000) 39, 90-100; Fedyk et al. J. Leukocyte Biol. (1999) 66, 667-673; Peled et al. Blood (2000) 95, 3289-3296). Particularly high levels of SDF-1 are found in bone-marrow stromal cells (Shirozu, M. et al. (1995) Genomics, 28, 495-500; Bleul, C. C. et al., (1996) J. Exp. Med. 184, 1101-1109).

The cell signaling initiated upon binding of SDF-1 to CXCR4 may also play an important role in tumor cell proliferation and regulation of angiogenesis associated with tumor growth (See, "Chemokines and Cancer" published by Humana Press (1999), Edited by B. J. Rollins; Arenburg et al. J Leukocyte Biol. (1997) 62, 554-562; Moore et al. J. Invest. Med. (1998) 46, 113-120; Moore et al. Trends Cardiovasc. Med. (1998) 8, 51-58; Seghal et al. J. Surg. Oncol. (1998) 69, 99-104). The expression of CXCR4 has been associated with osteosarcoma, pancreatic cancer, brain, breast, and colon cancer. (See, Paoletti et al. Int J. Oncol; (2001) 18, 11-6); Koshiba et al. Clin Cancer Res. (2000) 6, 3530-5); Muller, et al., Nature (2001) 410:50-56; and Murphy et al., WO 99/50461). In addition, some chemokines have been linked to metastasis of cancer from specific organs, including lymph node, bone marrow, and skin; or from carcinomas of breast, head and neck, melanoma or prostate origin. (See, Mueller et al., WO 01/38352).

The SDF-1/CXCR4 cell signaling pathway have been found to be involved in modulating non-tumor associated angiogenesis. Mice deficient for either CXCR4 or SDF-1 have defects in the formation of the large blood vessels that supply the organs of the GI tract and the brain, see Yong-Rui Zou, et. al., Nature 393, 591-594 (1998); Kazunobu Tachibana et. al., Nature 393, 595-599 (1998) and Takashi Nagasawa et. al., Nature 382, 635-638 (1996). In addition, subcutaneous injection of SDF-1 causes localized neovascularization (Rosalba Salcedo et al., American Journal of Pathology 154: 1125-1135 (1999)).

A role for CXCR4 in ocular neovascular disease is suggested by its expression pattern in the eye. mRNA for CXCR4 has been shown to "be expressed in vascular endothelial cells that are a component of blood vessels and capillaries (Orribretta Salvucci et al., Blood 99: 2703-2711 (2002). In addition, CXCR4 is expressed in the retinal pigmented epithelium (RPE) that lies between the choroidal vasculature and the retinal neurons (Isabel Crane et al., Journal of Immunology 165: 4372-4378 (2000). Thus, CXCR4 is in the right location to influence the process of CNV and diabetic retinopathy. It is also possible that CXCR4 may play a role in the non-neovascular form of AMD, also called dry or atrophic AMD. There is evidence to suggest that inflammation may contribute to the pathogenesis of dry AMD (Philip Penfold et al., Progress in

*Retinal and Eye Research* 20: 385-414 (2001), and CXCR4 has been implicated in the inflammatory process (Nicholas Lukacs et al., *American Journal of Pathology* 160: 1353-1360 (2002); Patrick Matthys et al., *Journal of Immunology* 167: 4686-4692 (2001) and Jose-Angel Gonzalo et al., *Journal of Immunology* 165: 499-508 (2000).

The interaction of SDF-1 to CXCR4 has also been implicated in the pathogenesis of atherosclerosis (Abi-Younes et al. Circ. Res. 86, 131-138 (2000)), renal allograft rejection (Eitner et al. Transplantation 66, 1551-1557 (1998)), asthma and allergic airway inflammation (Yssel et al. Clinical and Experimental Allergy 28, 104-109 (1998); J. Immunol. 164, 5935-5943 (2000); Gonzalo et al. J. Immunol. 165, 499-508 (2000)), Alzheimer's disease (Xia et al. J. Neurovirology 5, 32-41 (1999)), rheumatoid arthritis (US 2005/0202005) and Arthritis (Nanki et al. J. Immunol. 164, 5010-5014 (2000)).

As described above, early research efforts by a number of groups have indicated a role for the chemokine receptor CXCR4 in metastasis and tumor growth. Muller, et al., "Involvement of Chemokine Receptors in Breast Cancer Metastasis," Nature, 410:50-56 (2001) demonstrated that breast tumor cells use chemokine-mediated mechanisms, such as those regulating leukocyte trafficking, during the process of metastasis. Tumor cells express a distinct, non-random pattern of functionally active chemokine receptors. Signaling through CXCR4 mediates actin polymerization and pseudopodia formation in breast cancer cells, and induces chemotactic and invasive responses. Additionally, the organs representing the main sites of breast cancer metastasis (such as lymph nodes, bone marrow, and lungs) are the most abundant sources of ligand for the CXCR4 receptor.

Using immunodeficient mice, Muller and colleagues succeeded in reducing the metastasis of injected human breast cancer cells by treating mice with an antibody known to bind CXCR4. Their finding suggests that breast cancer metastasis could be reduced by treating a patient with a CXCR4 antagonist.

Bertolini, et al., "CXCR4 Neutralization, a Novel Therapeutic Approach for Non-Hodgkin's Lymphoma," Cancer Research, 62:3106-3112 (2002) demonstrated a reduction of tumor volume as well as prolonged survival of immunodeficient mice injected with human lymphoma cells treated with anti-CXCR4 antibodies. They interpreted their finding to mean that tumor volume could be reduced by treating a patient with a CXCR4 antagonist.

More recent studies suggest that another chemokine receptor, CCXCKR2, may also be a potential candidate in the treatment of cancer. CCXCKR2 is preferentially expressed in transformed cells over normal cells, with detectable expression in a number of human cancers. In vitro studies indicate that proliferation of CCXCKR2 expressing cells can be inhibited by an antagonist of CCXCKR2. In vivo studies in mice indicate that CCXCKR2 antagonists can inhibit tumor formation and tumor growth.

The potential importance of CCXCKR2 is illustrated by an alternative interpretation of the reduction in tumor volume seen by Bertolini and colleagues. This reduction could clearly be the result of an antibody-mediated clearance, and not the result of the anti-CXCR4 antibody as originally believed. In an antibody-mediated clearance, any antibody that recognized a protein on the cell surface of the lymphoma cells would have had the same effect as that attributed to the anti-CXCR4 antibody. Unfortunately, Bertolini and colleagues studies are inconclusive as to whether the observed tumor response was due to antibody-mediated clearance or interaction with CXCR4.

However it is now known that the lymphoma cells used by Bertolini and colleagues express both CXCR4 and CCXCKR2. SDF-1 is the only ligand for CXCR4. SDF-1 and I-TAC both bind CCXCKR2. Using anti-SDF-1 antibody, it has now been shown that antagonists of CCXCKR2 are responsible for the reduction in tumor load and increased survival rate. Because SDF-1 is the only ligand for CXCR4, one would expect neutralization of SDF-1 with anti-SDF-1 antibody would be equivalent to the neutralization of CXCR4 with anti-CXCR4 antibody. However, experiments using an anti-SDF-1 antibody demonstrated only a partial reduction in tumor load and an increased survival rate. As a result, CCXCKR2 is the likely target, as the continued activity appears due to the interactions of the second ligand, I-TAC, with CCXCKR2.

Until recently, the possible importance of CCXCKR2 in tumor cell proliferation, tumor growth, and metastasis was unknown. Now, with recent evidence pointing to the ability of certain CCXCKR2 antagonists to prevent the growth and spread of cancer, and expression patterns indicating a limited tissue distribution for the CCXCKR2 receptor.

Moreover, recently it has been discovered that CCXCKR2 can serve as a co-receptor for certain genetically divergent human immunodeficiency virus (HIV) and simian immunodeficiency virus (SIV), in particular for the HIV-2-ROD, an X4-tropic isolate (Shimizu, N. et al., *J. Virol.*, (2000) 74: 619-626; Balabanian, K., et al., *J. Biol. Chem.*, in press; published on Aug. 17, 2005 as Manuscript M508234200).

Still further, SDF-1, has been described to have a role in the mobilization of hematopoietic progenitor cells and stem cells, and in particular of those cells bearing the CXCR4 receptor, to specific hematopoietic tissues including bone marrow has been described (Hattori, K., et al., *Blood*, (2000) 97:3354-3360; WO 2005/000333, the disclosure of which are incorporated herein by reference). For example, it is known that CD34+ progenitor cells express CXCR4 and require SDF-1 produced by bone marrow stromal cells for chemoattraction and engraftment, and that in vitro, SDF-1 is chemotactic for both CD34+ cells and for progenitor/stem cells. SDF-1 is also an important chemoattractant, signaling via the CXCR4 receptor, for several other more committed progenitors and mature blood cells including T-lymphocytes and monocytes, pro- and pre-B lymphocytes, and megakaryocytes. As mentioned above, SDF-1 is the only ligand for the CXCR4 receptor. SDF-1 and I-TAC are both ligands for CCXCKR2 receptor. More recent studies suggest that the CCXCKR2 receptor may also play a part in stem cell mobilization processes.

It is apparent that the CXCR4 chemokine receptor and associated cell signaling processes plays a role in the pathology diseases, such as cancer, inflammation, HIV, stem cell related disorders, ocular disorders, etc. As such, it would be beneficial to have small molecule inhibitors of the CXCR4 receptor, that could serve to modulate (e.g., antagonize, agonize) the binding, signaling and chemotactic effects of the SDF-1 for the receptor. CXCR4. In addition, in view of the above, it is also apparent that compounds that are able to bind specifically to CCXCKR2 receptors may be useful to treating diseases and other biological conditions that may benefit from such interactions. The present invention fulfills this and other needs.

BRIEF SUMMARY OF THE INVENTION

In one aspect, the present invention provides for compounds having the formula I

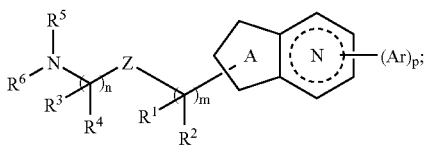

and pharmaceutically acceptable salts, hydrates and N-oxides thereof. In formula I, the substituents $R^1$, $R^2$, $R^3$ and $R^4$ at each occurrence are each independently selected from the group consisting of, hydrogen, halogen, $C_{1-8}$ alkyl, $C_{1-8}$ haloalkyl, $C_{1-8}$ heteroalkyl, $C_{2-8}$ alkenyl, $C_{2-8}$ alkynyl, in which the aliphatic portions of $R^1$-$R^4$ are each independently substituted with from 0-3 substituents selected from the group consisting of —OH, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein R$^m$ at each occurrence is independently an unsubstituted $C_{1-6}$ alkyl. The substituents $R^5$ and $R^6$ are each independently selected from the group consisting of hydrogen, $C_{1-8}$ alkyl, $C_{1-8}$ haloalkyl, $C_{2-8}$ alkenyl, $C_{2-8}$ alkynyl, $C_{3-10}$ cycloalkyl, $C_{3-10}$ heterocycloalkyl, $C_{1-8}$ acyl, $C_{1-8}$ alkyl-S(O)$_2$—, aryl, heteroaryl, aryl-$C_{1-6}$ alkyl and aryl-$C_{1-6}$ heteroalkyl. Optionally, the substituents $R^5$ and $R^6$ are combined to form a 5- to 10-membered ring system having from 1-3 heteroatoms selected from N, O and S. The aliphatic portions of $R^5$ and $R^6$ are further substituted with 0-3 substituents selected from the group consisting of —OH, —OR$''$, —OC(O)NHR$''$, —OC(O)N(R$''$)$_2$, —SH, —SR$''$, —S(O)R$''$, —S(O)$_2$R$''$, —SO$_2$NH$_2$, —S(O)$_2$NHR$''$, —S(O)$_2$N(R$''$)$_2$, —NHS(O)$_2$R$''$, —NR$''$S(O)$_2$R$''$, —C(O)NH$_2$, —C(O)NHR$''$, —C(O)N(R$''$)$_2$, —C(O)R$''$, —NHC(O)R$''$, —NR$''$C(O)R$''$, —NHC(O)NH$_2$, —NR$''$C(O)NH$_2$, —NR$''$C(O)NHR$''$, —NHC(O)NHR$''$, —NR$''$C(O)N(R$''$)$_2$, —NHC(O)N(R$''$)$_2$, —CO$_2$H, —CO$_2$R$''$, —NHCO$_2$R$''$, —NR$''$CO$_2$R$''$, —CN, —NO$_2$, —NH$_2$, —NHR$''$, —N(R$''$)$_2$, —NR$''$S(O)NH$_2$ and —NR$''$S(O)$_2$NHR$''$, in which the group R$''$ at each occurrence is independently an unsubstituted $C_{1-6}$ alkyl. The symbol Z, in formula I, is a linking group selected from the group consisting of —C(O)—, —C(=NOR$^b$)—, —C(=NR$^d$)—, —C(O)O—, —CONR$^b$—, —OC(O)NR$^b$—, —NR$^b$C(O)—, —NR$^b$C(O)$_2$—, —NR$^b$C(O)NR$^c$—, —NHC(=NH)NH—, —NR$^d$C(=NH)NH—, —NHC(=NR$^d$)NH—, —NHC(=NH)—NR$^d$—, —S(O)—, —S(O)$_2$—, —NR$^b$S(O)$_2$—, —S(O)$_2$NR$^b$— and —NR$^b$S(O)$_2$NR$^c$—. R$^b$ and R$^c$ at each occurrence are members independently selected from the group consisting of hydrogen, $C_{1-8}$ acyl, $C_{1-8}$ alkyl-S(O)$_2$—, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl, aryl-$C_{1-4}$ alkyl; and R$^d$ is a member independently selected from the group including, but not limited to $C_{1-8}$ alkyl, $C_{1-8}$ acyl, $C_{1-8}$ alkyl-S(O)$_2$—, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl. The aliphatic portions of the linking group Z are substituted with from 0-3 substituents selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, in which R$^o$ at each occurrence is independently an unsubstituted $C_{1-6}$ alkyl. The subscripts m and n are each independently an integer from 1 to 6. In formula I, the substituents $R^1$ and $R^2$, $R^3$ and $R^4$, $R^3$ and $R^5$, $R^3$ and $R^6$, $R^5$ and the R$^b$, R$^c$ or R$^d$ group of Z, $R^6$ and the R$^b$, R$^c$ or R$^d$ group of Z, $R^3$ and the R$^b$, R$^c$ or R$^d$ group of Z, and $R^2$ and the R$^b$, R$^c$ or R$^d$ group of Z are optionally combined to form a 5-10 membered ring having from 0-2 heteroatoms selected from the group consisting of N, O and S. Also, when the subscripts m or n in formula I, is an integer from 2-6, the $R^1$ and $R^2$, or $R^3$ and $R^4$ substituents that are combined can be attached to the same or different carbon atoms. The ring represented by

in formula I, is a fused 5-membered heteroaromatic or heterocycloalkane ring selected from the group including, but not limited to, pyrazole, pyrrole, imidazole, triazole, furan, thiene, oxazole, oxadiazole, pyrrolidine, 2-oxopyrrolidine, 2-oxo-oxazolidine and 2-oxo-imidazolidine, in which said ring is substituted with 0-2 substitutents selected from the group consisting of -L$^1$R$^8$ and —R$^8$. R$^8$ at each occurrence is a member selected from the group consisting of hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkyl-$C_{1-6}$ alkyl, aryl-$C_{1-6}$ alkyl, heterocycloalkyl-$C_{1-6}$ alkyl, aryl-$C_{1-6}$ heteroalkyl, aryl, heteroaryl or halogen; or any two R$^8$ group can be combined to form a 5- to 6-membered aryl or heteroaryl ring. The symbol L$^1$ represents a linking group selected from the group consisting of —C(O)—, —C(=NOR$^e$)—, —C(=NR$^g$)—, —CO$_2$—, —CONR$^e$—, —OC(O)NR$^e$—, —NR$^e$C(O)—, —NR$^e$C(O)$_2$—, —NR$^e$C(O)NR$^f$—, —NHC(=NH)NH—, —NR$^g$C(=NH)NH—, —NHC(=NR$^g$)NH—, —NHC(=NH)—NR$^g$—, —S(O)—, —S(O)$_2$—, —NR$^e$S(O)$_2$—, —S(O)$_2$NR$^e$— and —NR$^e$S(O)$_2$NR$^f$—. R$^e$ and R$^f$, at each occurrence, is independently is a member selected from the group consisting of hydrogen, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl, aryl-$C_{1-4}$ alkyl. R$^g$, at each occurrence, is independently a member selected from the group consisting of $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl. The aliphatic portions of the R$^8$ group is substituted with from 0-3 substituents selected from the group consisting of halogen, —OH, —OR$^q$, —OC(O)NHR$^q$, —OC(O)N(R$^q$)$_2$, —SH, —SR$^q$, —S(O)R$^q$, —S(O)$_2$R$^q$, —SO$_2$NH$_2$, —S(O)$_2$NHR$^q$, —S(O)$_2$N(R$^q$)$_2$, —NHS(O)$_2$R$^q$, —NR$^q$S(O)$_2$R$^q$, —C(O)NH$_2$, —C(O)NHR$^q$, —C(O)N(R$^q$)$_2$, —C(O)R$^q$, —NHC(O)R$^q$, —NR$^q$C(O)R$^q$, —NHC(O)NH$_2$, —NR$^q$C(O)NH$_2$, —NR$^q$C(O)NHR$^q$, —NHC(O)NHR$^q$, —NR$^q$C(O)N(R$^q$)$_2$, —NHC(O)N(R$^q$)$_2$, —CO$_2$H, —CO$_2$R$^q$, —NHCO$_2$R$^q$, —NR$^q$CO$_2$R$^q$, —CN, —NO$_2$, —NH$_2$, —NHR$^q$, —N(R$^q$)$_2$, —NR$^q$S(O)NH$_2$ and —NR$^q$S(O)$_2$NHR$^q$, in which each R$^q$ is independently an unsubstituted C$_{1-6}$ alkyl. The ring represented by

in formula I, is a fused 6-membered aromatic, heteroaromatic, cycloalkane or heterocycloalkane ring selected from the group including, but not limited to, benzene, pyridine, pyrimidine, pyrazine, pyridazine, 2-oxopiperidine, 1-oxocyclohexane, 2,4-dioxo-5,6-dihydropyrimidine, 2-oxo-4,5-dehydropiperidine and cyclohexane, in which said ring has from 0-4 R$^7$ substituents independently selected from the group consisting of halogen, cyano, heteroaryl, —R$^j$, —NO$_2$, —CO$_2$R$^h$, —C(O)NR$^h$R$^i$, —C(O)R$^h$, —S(O)R$^j$, —S(O)$_2$R$^j$, —OC(O) R$^h$, —NR$^h$—C(O)NR$^h$R$^i$, —NH—C(NH$_2$)=NH, —NR$^i$C(NH$_2$)=NH, —NH—C(NH$_2$)=NR$^j$, —NH—C(NHR$^j$)=NH, —NR$^h$S(O)$_2$R$^j$, —NR$^h$S(O)$_2$R$^j$, —NR$^h$S(O)$_2$NR$^h$R$^i$, —N$_3$, —C(NOR$^h$)R$^i$, —C(NR$^h$V)=NV, —N(V)C(R$^h$)=NV, —X$^1$C(NOR$^h$)R$^i$, —X$^1$C(NR$^h$V)=NV, —X$^1$N(V)C(R$^h$)=NV, —X$^1$NR$^h$R$^i$, —X$^1$SR$^h$, —X$^1$CN, —X$^1$NO$_2$, —X$^1$CO$_2$R$^h$, —X$^1$CONR$^h$R$^i$, —X$^1$C(O)R$^h$, —X$^1$OC(O)NR$^h$R$^i$, —X$^1$NR$^i$C(O)R$^h$, —X$^1$NR$^i$C(O)$_2$R$^j$, —X$^1$NR$^h$C(O)NR$^i$R$^j$, —X$^1$ NH—C(NH$_2$)=NH, —X$^1$NR$^i$C(NH$_2$)=NH, —X$^1$NH—C(NH$_2$)=NR$^j$, —X$^1$NH—C(NHR$^j$)=NH, —X$^1$S(O)R$^j$, —X$^1$S(O)$_2$R$^j$, —X$^1$NR$^h$S(O)$_2$R$^j$, —X$^1$S(O)$_2$NR$^h$R$^i$, —X$^1$N$_3$, —NR$^h$R$^i$, —OR$^h$, —SR$^h$, —NR$^i$C(O)R$^h$, —NR$^i$C(O)$_2$R$^j$, —S(O)$_2$NR$^h$R$^i$, —X$^1$OR$^h$, —O—X$^1$OR$^h$, —O—X$^1$NR$^h$R$^i$ and —NR$^i$—X$^1$CO$_2$R$^h$. Optionally, any two R$^7$ substituents located on adjacent atoms can be combined to form a 5- to 7-membered ring optionally having from 1-3 heteroatoms selected from the group consisting of N, O and S. The linking group X$^1$ is selected from the group consisting of C$_{1-4}$ alkylene, C$_{1-4}$ heteroalkylene, C$_{2-4}$ alkenylene and C$_{2-4}$ alkynylene. Each R$^h$ and R$^i$ is a member independently selected from the group consisting of hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl and aryl-C$_{1-4}$ alkyl. Optionally, R$^h$ and R$^i$, when attached to the same nitrogen atom, can be combined to form a five or six-membered ring having from 0 to 2 additional heteroatoms as ring members. Each R$^j$ is independently a member selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl. Each of X$^1$, R$^h$, R$^i$ and R$^j$ is further substituted with from 0-3 members selected from the group consisting of halogen, —OH, —OR$^r$, —OC(O)NHR$^r$, —OC(O)N(R$^r$)$_2$, —SH, —SR$^r$, —S(O)R$^r$, —S(O)$_2$R$^r$, —SO$_2$NH$_2$, —S(O)$_2$NHR$^r$, —S(O)$_2$N(R$^r$)$_2$, —NHS(O)$_2$R$^r$, —NR$^r$S(O)$_2$R$^r$, —C(O)NH$_2$, —C(O)NHR$^r$, —C(O)N(R$^r$)$_2$, —C(O)R$^r$, —NHC(O)R$^r$, —NR$^r$C(O)R$^r$, —NHC(O)NH$_2$, —NR$^r$C(O)NH$_2$, —NR$^r$C(O)NHR$^r$, —NHC(O)NHR$^r$, —NR$^r$C(O)N(R$^r$)$_2$, —NHC(O)N(R$^r$)$_2$, —CO$_2$H, —CO$_2$R$^r$, —NHCO$_2$R$^r$, —NR$^r$CO$_2$R$^r$, —CN, —NO$_2$, —NH$_2$, —NHR$^r$, —N(R$^r$)$_2$, —NR$^r$S(O)NH$_2$ and —NR$^r$S(O)$_2$NHR$^r$, wherein each R$^r$ is independently an unsubstituted C$_{1-6}$ alkyl. The symbol V is independently selected from the group including, but not limited to —R$^j$, —CN, —CO$_2$R$^h$ and —NO$_2$. The substituent Ar is a 5-10 membered aryl or a heteroaryl ring system having from 1-3 nitrogen atoms. The Ar group has from 1-5 R$^9$ substituents independently selected from the group consisting of hydroxy, halogen, cyano, heteroaryl, —R$^m$, —NO$_2$, —CO$_2$R$^k$, —C(O)NR$^k$R$^L$, —C(O)R$^k$, —S(O)R$^m$, —S(O)$_2$R$^m$, —OC(O)R$^k$, —NR$^k$—C(O)NR$^k$R$^L$, —NH—C(NH$_2$)=NH, —NR$^m$C(NH$_2$)=NH, —NH—C(NH$_2$)=NR$^m$, —NH—C(NHR$^m$)=NH, —NR$^k$S(O)$_2$R$^m$, —NR$^k$S(O)$_2$R$^m$, —NR$^k$S(O)$_2$NR$^k$R$^L$, —N$_3$, —C(NOR$^k$)R$^L$, —C(NR$^k$U)=NU, —N(U)C(R$^k$)=NU, —X$^2$C(NOR$^k$) R$^L$, —X$^2$C(NR$^k$U)=NU, —X$^2$N(U)C(R$^k$)=NU, —X$^2$NR$^k$R$^L$, —X$^2$SR$^k$, —X$^2$CN, —X$^2$NO$_2$, —X$^2$CO$_2$R$^k$, —X$^2$CONR$^k$R$^L$, —X$^2$C(O)R$^k$, —X$^2$OC(O)NR$^k$R$^L$, —X$^2$NR$^L$C(O)R$^k$, —X$^2$NR$^L$C(O)$_2$R$^m$, —X$^2$NR$^k$C(O)NR$^L$R$^m$, —X$^2$NH—C(NH$_2$)=NH, —X$^2$NR$^m$C(NH$_2$)=NH, —X$^2$ NH—C(NH$_2$)=NR$^m$, —X$^1$NH—C(NHR$^m$)=NH, —X$^1$S(O)R$^m$, —X$^2$S(O)$_2$R$^m$, —X$^2$NR$^k$S(O)$_2$R$^m$, —X$^2$S(O)$_2$NR$^k$R$^L$, —X$^2$N$_3$, —NR$^k$R$^L$, —OR$^m$, —SR$^k$, —NR$^L$C(O)R$^k$, —NR$^L$C(O)$_2$R$^m$, —S(O)$_2$NR$^k$R$^L$, —X$^2$OR$^k$, —O—X$^2$OR$^k$, —O—X$^2$NR$^k$R$^L$ and —NR$^L$—X$^2$CO$_2$R$^k$. Optionally any two R$^9$ substituents located on adjacent atoms can be combined to form a 5- to 7-membered ring optionally having from 1-3 heteroatoms selected from the group consisting of N, O and S. The linking group X$^2$ is selected from the group consisting of C$_{1-4}$ alkylene, C$_{1-4}$ heteroalkylene, C$_{2-4}$ alkenylene and C$_{2-4}$ alkynylene. Each R$^k$ and R$^L$ is independently selected from the group consisting of hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl. Optionally, the groups R$^k$ and R$^L$ when attached to the same nitrogen atom can be combined to form a five or six-membered ring having from 0 to 2 additional heteroatoms as ring members. Each R$^m$ is independently a member selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl, aryl-C$_{1-6}$ alkyl. The aliphatic portions of X$^2$, R$^k$, R$^L$ and R$^m$ are further substituted with from 0-3 members selected from the group consisting of halogen, —OH, —OR$^s$, —OC(O)NHR$^s$, —OC(O)N(R$^s$)$_2$, —SH, —SR$^s$, —S(O)R$^s$, —S(O)$_2$R$^s$, —SO$_2$NH$_2$, —S(O)$_2$NHR$^s$, —S(O)$_2$N(R$^s$)$_2$, —NHS(O)$_2$R$^s$, —NR$^s$S(O)$_2$R$^s$, —C(O)NH$_2$, —C(O)NHR$^s$, —C(O)N(R$^s$)$_2$, —C(O)R$^s$, —NHC(O)R$^s$, —NR$^s$C(O)R$^s$, —NHC(O)NH$_2$, —NR$^s$C(O)NH$_2$, —NR$^s$C(O)NHR$^s$, —NHC(O)NHR$^s$, —NR$^s$C(O)N(R$^s$)$_2$, —NHC(O)N(R$^s$)$_2$, —CO$_2$H, —CO$_2$R$^s$, —NHCO$_2$R$^s$, —NR$^s$CO$_2$R$^s$, —CN, —NO$_2$, —NH$_2$, —NHR$^s$, —N(R$^s$)$_2$, —NR$^s$S(O)NH$_2$ and —NR$^q$S(O)$_2$NHR$^s$, wherein each R$^s$ is independently an unsubstituted C$_{1-6}$ alkyl; and the symbol U is independently selected from the group consisting of —R$^m$, —CN, —CO$_2$R$^k$ and —NO$_2$. The subscript p, in formula I, is an integer from 0-1.

In another embodiment, the present invention provides for pharmaceutical compositions comprising compounds of formula I. Also described herein is a method of preventing the binding the CXCR4 receptor expressed on cells with its natural ligand SDF-1α or SDF-1β and for treating CXCR4-mediated diseases or conditions comprising administering to a patient in need thereof a therapeutically effective amount of a compound of formula I. Also described herein is a method of preventing the binding the CCXCKR2 (CXCR7) receptor expressed on cells with its SDF-1 or I-TAC and for treating CCXCKR2-mediated diseases or conditions comprising administering to a patient in need thereof a therapeutically effective amount of a compound of formula I.

DETAILED DESCRIPTION OF THE INVENTION

I. Abbreviation and Definitions

Figure 1A:
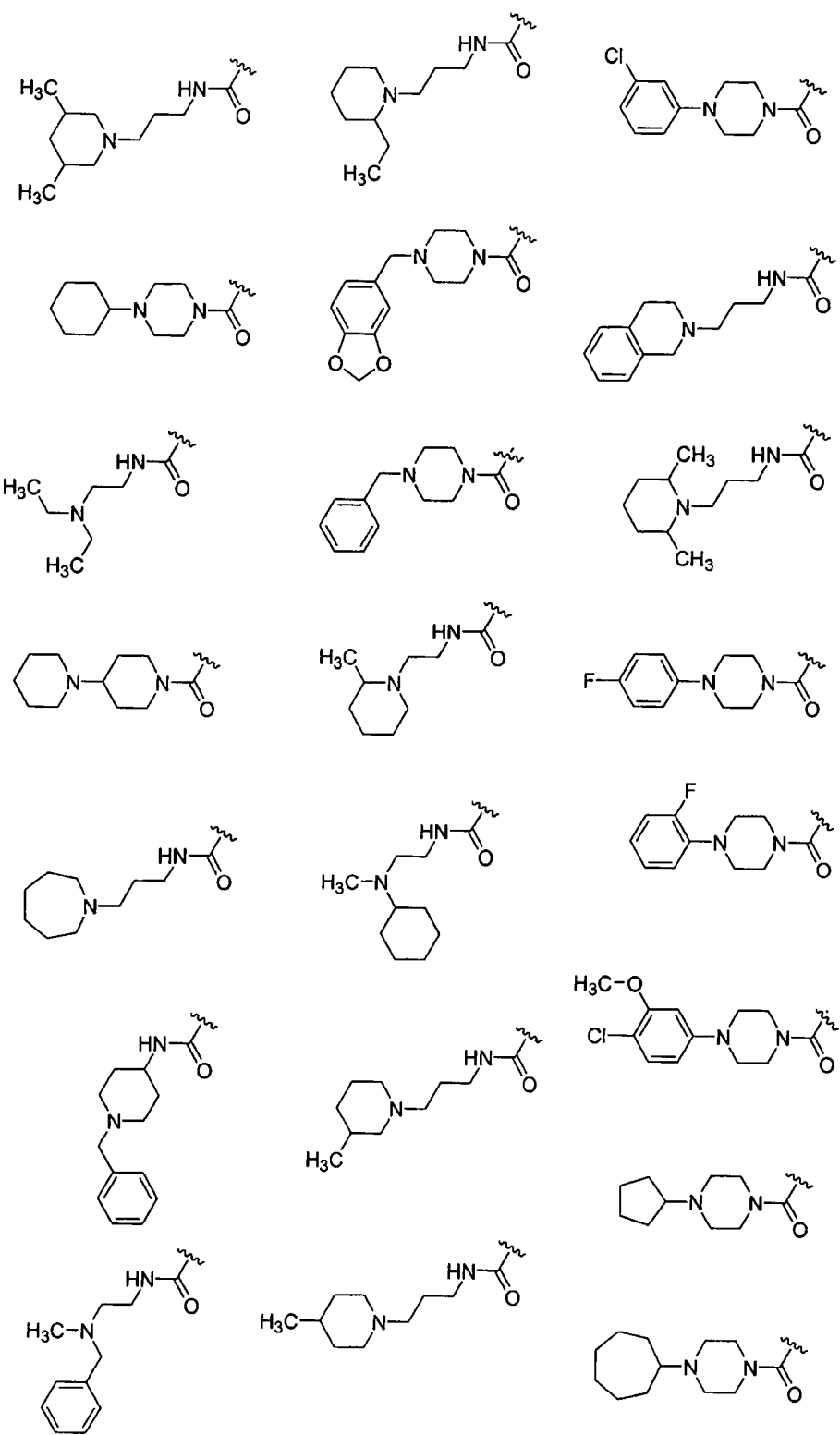
FIGS. 1A-1D show preferred R$^5$R$^6$N—(CR$^3$R$^4$)$_n$Z-groups in Formula I of the invention.

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" or "cycloalkane" refers to hydrocarbon rings having the indicated number of ring atoms (e.g., $C_{3-6}$ cycloalkyl) and being fully saturated or having no more than one double bond between ring vertices. "Cycloalkyl" or "cycloalkane" is also meant to refer to bicyclic and polycyclic hydrocarbon rings such as, for example, bicyclo[2.2.1]heptane, bicyclo[2.2.2]octane, etc. The term "heterocycloalkyl" or "heterocycloalkane" refers to a cycloalkyl or cycloalkane group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl and heterocycloalkane groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-5-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-10 membered ring with the nitrogen atom to which each is attached. The ring may be monocyclic, bicyclic or polycyclic. Accordingly, a group represented as —$NR^aR^b$ is meant to include piperidinyl, pyrrolidinyl, morpholinyl, azetidinyl, decahydro-isoquinolinyl, decahydroquinolinyl, tetrahydroquinolinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" or "aromatic" means, unless otherwise stated, a polyunsaturated, typically aromatic, hydrocarbon group which can be a single ring or multiple rings (up to three rings) which are fused together or linked covalently. The term "heteroaryl" or "heteroaromatic" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, 7-, 8-, 9- or 10-membered monocyclic or polycyclic ring. For example, —NR'R" is meant to include 1-pyrrolidinyl, 1-tetrahydroquinolinyl and 4-morpholinyl. The term "acyl" as used by itself or as part of another group refers to an alkyl radical wherein two substitutents on the carbon that is closest to the point of attachment for the radical is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substitutent of the formula —(CH$_2$)$_s$— X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

A wavy bond, ~~~, that intersects a single, double, or triple bond in a chemical structure depicted herein, indicated the point of attachment the single, double, or triple bond to the remainder of the molecule.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. EMBODIMENTS OF THE INVENTION

A. Compounds

In one aspect, the present invention provides for compounds having the formula

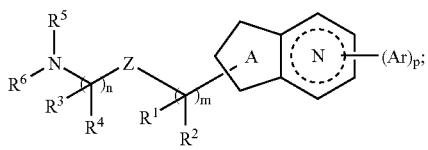

and pharmaceutically acceptable salts, hydrates and N-oxides thereof.

In formula I, the substituents $R^1$, $R^2$, $R^3$ and $R^4$ at each occurrence are each independently selected from the group consisting of hydrogen, halogen, $C_{1-8}$ alkyl, $C_{1-8}$ haloalkyl, $C_{1-8}$ heteroalkyl, $C_{2-8}$ alkenyl, and $C_{2-8}$ alkynyl, in which the aliphatic portions of $R^1$-$R^4$ are each independently substituted with from 0-3 substituents selected from the group consisting of —OH, —OR''', —OC(O)NHR''', —OC(O)N(R''')$_2$, —SH, —SR''', —S(O)R''', —S(O)$_2$R''', —SO$_2$NH$_2$, —S(O)$_2$NHR''', —S(O)$_2$N(R''')$_2$, —NHS(O)$_2$R''', —NR'''S(O)$_2$R''', —C(O)NH$_2$, —C(O)NHR''', —C(O)N(R''')$_2$, —C(O)R''', —NHC(O)R''', —NR'''C(O)R''', —NHC(O)NH$_2$, —NR'''C(O)NH$_2$, —NR'''C(O)NHR''', —NHC(O)NHR''', —NR'''C(O)N(R''')$_2$, —NHC(O)N(R''')$_2$, —CO$_2$H, —CO$_2$R''', —NHCO$_2$R''', —NR'''CO$_2$R''', —CN, —NO$_2$, —NH$_2$, —NHR''', —N(R''')$_2$, —NR'''S(O)NH$_2$ and —NR'''S(O)$_2$NHR''', wherein R''' at each occurrence is an unsubstituted $C_{1-6}$ alkyl.

The substituents $R^5$ and $R^6$, in formula I, are each independently selected from the group consisting of hydrogen, $C_{1-8}$ alkyl, $C_{1-8}$ haloalkyl, $C_{2-8}$ alkenyl, $C_{2-8}$ alkynyl, $C_{3-10}$ cycloalkyl, $C_{3-10}$ heterocycloalkyl, $C_{1-8}$ acyl, $C_{1-8}$ alkyl-S(O)$_2$—, aryl, heteroaryl, aryl-$C_{1-6}$ alkyl and aryl-$C_{1-6}$ heteroalkyl. Optionally, the substituents $R^5$ and $R^6$ are combined to form a 5- to 10-membered ring system having from 1-3 heteroatoms selected from N, O and S; in which the aliphatic portions of $R^5$ and $R^6$ are further substituted with 0-3 substituents selected from the group consisting of —OH, —OR'', —OC(O)NHR'', —OC(O)N(R'')$_2$, —SH, —SR'', —S(O)R'', —S(O)$_2$R'', —SO$_2$NH$_2$, —S(O)$_2$NHR'', —S(O)$_2$N(R'')$_2$, —NHS(O)$_2$R'', —NR''S(O)$_2$R'', —C(O)NH$_2$, —C(O)NHR'', —C(O)N(R'')$_2$, —C(O)R'', —NHC(O)R'', —NR''C(O)R'', —NHC(O)NH$_2$, —NR''C(O)NH$_2$, —NR''C(O)NHR'', —NHC(O)NHR'', —NR''C(O)N(R'')$_2$, —NHC(O)N(R'')$_2$, —CO$_2$H, —CO$_2$R'', —NHCO$_2$R'', —NR''CO$_2$R'', —CN, —NO$_2$, —NH$_2$, —NHR'', —N(R'')$_2$, —NR''S(O)NH$_2$ and —NR''S(O)$_2$NHR'', wherein the group R'' at each occurrence is an unsubstituted $C_{1-6}$ alkyl.

The symbol Z, in formula I, is a linking group selected from the group consisting of —C(O)—, —C(=NOR$^b$)—, —C(=NR$^d$)—, —C(O)O—, —CONR$^b$—, —OC(O)NR$^b$—, —NR$^b$C(O)—, —NR$^b$C(O)$_2$—, —NR$^b$C(O)NR$^c$—, —NHC(=NH)NH—, —NR$^d$C(=NH)NH—, —NHC(=NR$^d$)NH—, —NHC(=NH)—NR$^d$—, —S(O)—, —S(O)$_2$—, —NR$^b$S(O)$_2$—, —S(O)$_2$NR$^b$— and —NR$^b$S(O)$_2$NR$^c$—. $R^b$ and $R^c$ at each occurrence are members independently selected from the group consisting of hydrogen, $C_{1-8}$ acyl, $C_{1-8}$ alkyl-S(O)$_2$—, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl; $R^d$ is a member independently selected from the group consisting of $C_{1-8}$ alkyl, $C_{1-8}$ acyl, $C_{1-8}$ alkyl-S(O)$_2$—, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl. The aliphatic portions of the linking group Z are substituted with from 0-3 substituents selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, in which R° at each occurrence is independently an unsubstituted $C_{1-6}$ alkyl.

The subscripts m and n, in formula I, are each independently an integer from 1 to 6. In formula I, the substituents $R^1$ and $R^2$, $R^3$ and $R^4$, $R^3$ and $R^5$, $R^3$ and $R^6$, $R^5$ and the $R^b$, $R^c$ or $R^d$ group of Z, $R^6$ and the $R^b$, $R^c$ or $R^d$ group of Z, $R^3$ and the $R^b$, $R^c$ or $R^d$ group of Z, and $R^2$ and the $R^b$, $R^c$ or $R^d$ group of Z are optionally combined to form a 5-10 membered ring having from 0-2 heteroatoms selected from the group consisting of N, O and S. Also, when the subscripts m or n, in formula I, is an integer from 2-6, the $R^1$ and $R^2$, or $R^3$ and $R^4$ substituents that are combined can be attached to the same or different carbon atoms.

The ring represented by

in formula I, is a fused 5-membered heteroaromatic or heterocycloalkane ring selected from the group including, but not limited to, pyrazole, pyrrole, imidazole, triazole, furan, thiene, oxazole, oxadiazole, pyrrolidine, 2-oxopyrrolidine, 2-oxo-oxazolidine and 2-oxo-imidazolidine, in which said ring is substituted with 0-2 substituents selected from the group consisting of -L$^1$R$^8$ and —R$^8$. R$^8$ at each occurrence is a member selected from the group consisting of hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkyl-$C_{1-6}$ alkyl, aryl-$C_{1-6}$ alkyl, heterocycloalkyl-$C_{1-6}$ alkyl, aryl-$C_{1-6}$ heteroalkyl, aryl, heteroaryl and halogen; or any two $R^8$ substituents located on adjacent atoms can be combined to form a 5- to 6-membered aryl or heteroaryl ring. The symbol $L^1$ represents a linking group selected from the group consisting of —C(O)—, —C(=NOR$^e$)—, —C(=NR$^g$)—, —CO$_2$—, —CONR$^e$—, —OC(O)NR$^e$—, —NR$^e$C(O)—, —NR$^e$C(O)$_2$—, —NR$^e$C(O)NR$^f$—, —NHC(=NH)NH—, —NR$^g$C(=NH)NH—, —NHC(=NR$^g$)NH—, —NHC(=NH)—NR$^g$—, —S(O)—, —S(O)$_2$—, —NR$^e$S(O)$_2$—, —S(O)$_2$NR$^e$— and —NR$^e$S(O)$_2$NR$^f$—. R$^e$ and R$^f$, at each occurrence, are independently a member selected from the group consisting of hydrogen, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl. R$^8$, at each occurrence, is independently a member selected from the group consisting of $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl. The aliphatic portions of the $R^8$ group is substituted with from 0-3 substituents selected from the group consisting of halogen, —OH, —OR$^q$, —OC(O)NHR$^q$, —OC(O)N(R$^q$)$_2$, —SH, —SR$^q$, —S(O)R$^q$, —S(O)$_2$R$^q$, —SO$_2$NH$_2$, —S(O)$_2$NHR$^q$, —S(O)$_2$N(R$^q$)$_2$, —NHS(O)$_2$R$^q$, —NR$^q$S(O)$_2$R$^q$, —C(O)NH$_2$, —C(O)NHR$^q$, —C(O)N(R$^q$)$_2$, —C(O)R$^q$, —NHC(O)R$^q$, —NR$^q$C(O)R$^q$, —NHC(O)NH$_2$, —NR$^q$C(O)NH$_2$, —NR$^q$C(O)NHR$^q$, —NHC(O)NHR$^q$, —NR$^q$C(O)N(R$^q$)$_2$, —NHC(O)N(R$^q$)$_2$, —CO$_2$H, —CO$_2$R$^q$, —NHCO$_2$R$^q$, —NR$^q$CO$_2$R$^q$, —CN, —NO$_2$, —NH$_2$, —NHR$^q$, —N(R$^q$)$_2$, —NR$^q$S(O)NH$_2$ and —NR$^q$S(O)$_2$NHR$^q$, in which each R$^q$ is independently an unsubstituted $C_{1-6}$ alkyl.

The ring represented by

in formula I, is a fused 6-membered aromatic, heteroaromatic, cycloalkane or heterocycloalkane ring system selected from the group including, but not limited to, benzene, pyridine, pyrimidine, pyrazine, pyridazine, 2-oxopiperidine, 1-oxocyclohexane, 2,4-dioxo-5,6-dihydropyrimidine, 2-oxo-4,5-dehydropiperidine and cyclohexane, in which said ring has from 0-4 R$^7$ substituents independently selected from the group consisting of halogen, cyano, heteroaryl, —R$^j$, —NO$_2$, —CO$_2$R$^h$, —C(O)NR$^h$R$^i$, —C(O)R$^h$, —S(O)R$^j$, —S(O)$_2$R$^j$, —OC(O)R$^h$, —NR$^h$—C(O)NR$^h$R$^i$, —NH—C(NH$_2$)=NH, —NR$^j$C(NH$_2$)=NH, —NH—C(NH$_2$)=NR$^j$, —NH—C(NHR$^j$)=NH, —NR$^h$S(O)$_2$R$^j$, —NR$^h$S(O)$_2$R$^j$, —NR$^h$S(O)$_2$NR$^h$R$^i$, —N3, —C(NOR$^h$)R$^i$, —C(NR$^h$V)=NV, —N(V)C(R$^h$)=NV, —X$^1$C(NOR$^h$)R$^i$, —X$^1$C(NR$^h$V)=NV, —X$^1$N(V)C(R$^h$)=NV, —X$^1$NR$^h$R$^i$, —X$^1$SR$^h$, —X$^1$CN, —X$^1$NO$_2$, —X$^1$CO$_2$R$^h$, —X$^1$CONR$^h$R$^i$, —X$^1$C(O)NR$^h$R$^i$, —X$^1$NR$^i$(O)$_2$R$^j$, —X$^1$NR$^h$C(O)NR$^i$R$^j$, —X$^1$NH—C(NH$_2$)=NH, —X$^1$NR$^j$C(NH$_2$)=NH, —X$^1$NH—C(NH$_2$)=NR$^j$, —X$^1$NH—C(NHR$^j$)=NH, —X$^1$S(O)R$^j$, —X$^1$S(O)$_2$R$^j$, —X$^1$NR$^h$S(O)$_2$R$^j$, —X$^1$S(O)$_2$NR$^h$R$^i$, —X$^1$N$_3$, —NR$^h$R$^i$, —OR$^h$, —SR$^h$, —NR$^i$C(O)R$^h$, —NR$^i$C(O)$_2$R$^j$, —S(O)$_2$NR$^h$R$^i$, —X$^1$OR$^h$, —O—X$^1$OR$^h$, —O—X$^1$NR$^h$R$^i$ and —NR$^i$—X$^1$CO$_2$R$^h$. Optionally, any two R$^7$ substituents located on adjacent atoms can be combined to form a 5- to 7-membered ring optionally having from 1-3 heteroatoms selected from the group consisting of N, O and S. The linking group X$^1$ is a member selected from the group consisting of $C_{1-4}$ alkylene, $C_{1-4}$ heteroalkylene, $C_{2-4}$ alkenylene and $C_{2-4}$ alkynylene. Each R$^h$ and R$^i$ is a member independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-4}$ alkyl. Optionally, R$^h$ and R$^i$ when attached to the same nitrogen atom can be combined to form a five or six-membered ring having from 0 to 2 additional heteroatoms as ring members. Each R$^j$ is independently a member selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl. Each of X$^1$, R$^h$, R$^i$ and R$^j$ is further substituted with from 0-3 members selected from the group including but not limited to halogen, —OH, —OR$^r$, —OC(O)NHR$^r$, —OC(O)N(R$^r$)$_2$, —SH, —SR$^r$, —S(O)R$^r$, —S(O)$_2$R$^r$, —SO$_2$NH$_2$, —S(O)$_2$NHR$^r$, —S(O)$_2$N(R$^r$)$_2$, —NHS(O)$_2$R$^r$, —NR$^r$S(O)$_2$R$^r$, —C(O)NH$_2$, —C(O)NHR$^r$, —C(O)N(R$^r$)$_2$, —C(O)R$^r$, —NHC(O)R$^r$, —NR$^r$C(O)R$^r$, —NHC(O)NH$_2$, —NR$^r$C(O)NH$_2$, —NR$^r$C(O)NHR$^r$, —NHC(O)NHR$^r$, —NR$^r$C(O)N(R$^r$)$_2$, —NHC(O)N(R$^r$)$_2$, —CO$_2$H, —CO$_2$R$^r$, —NHCO$_2$R$^r$, —NR$^r$CO$_2$R$^r$, —CN, —NO$_2$, —NH$_2$, —NHR$^r$, —N(R$^r$)$_2$, —NR$^r$S(O)NH$_2$ and —NR$^r$S(O)$_2$NHR$^r$, wherein each R$^r$ is independently an unsubstituted $C_{1-6}$ alkyl. The symbol V is independently selected from the group consisting of —R$^j$, —CN, —CO$_2$R$^h$ and —NO$_2$.

The substituent Ar, in formula I, is a 5-10 membered aryl or a heteroaryl ring system having from 1-3 nitrogen atoms. The Ar group has from 1-5 R$^9$ substituents independently selected from the group including, but not limited to, hydroxy, halogen, cyano, heteroaryl, —R$^m$, —NO$_2$, —CO$_2$R$^k$, —C(O)NR$^k$R$^L$, —C(O)R$^k$, —S(O)R$^m$, —S(O)$_2$R$^m$, —OC(O)R$^k$, —NR$^k$—C(O)NR$^k$R$^L$, —NH—C(NH$_2$)=NH, —NR$^m$C(NH$_2$)=NH, —NH—C(NH$_2$)=NR$^m$, —NH—C(NHR$^m$)=NH, —NR$^k$S(O)$_2$R$^m$, —NR$^k$S(O)$_2$R$^m$, —NR$^k$S(O)$_2$NR$^k$R$^L$, —N$_3$, —C(NOR$^k$)R$^L$, —C(NR$^k$U)=NU, —N(U)C(R$^k$)=NU, —X$^2$C(NOR$^k$)R$^L$, —X$^2$C(NR$^k$U)=NU, —X$^2$N(U)C(R$^k$)=NU, —X$^2$NR$^k$R$^L$, —X$^2$SR$^k$, —X$^2$CN, —X$^2$NO$_2$, —X$^2$CO$_2$R$^k$, —X$^2$CONR$^k$R$^L$, —X$^2$C(O)R$^k$, —X$^2$OC(O)NR$^k$R$^L$, —X$^2$NR$^L$C(O)R$^k$, —X$^2$NR$^L$ C(O)$_2$R$^m$, —X$^2$NR$^k$C(O)NR$^L$R$^m$, —X$^2$NH—C(NH$_2$)=NH, —X$^2$NR$^m$C(NH$_2$)=NH, —X$^2$NH—C(NH$_2$)=NR$^m$, —X$^2$NH—C(NHR$^m$)=NH, —X$^2$S(O)R$^m$, —X$^2$S(O)$_2$R$^m$, —X$^2$NR$^k$S(O)$_2$R$^m$, —X$^2$S(O)$_2$NR$^k$R$^L$, —X$^2$ N$_3$, —NR$^k$R$^L$, —OR$^m$, —SR$^k$, —NR$^L$C(O)R$^k$, —NR$^L$C(O)$_2$R$^m$, —S(O)$_2$NR$^k$R$^L$, —X$^2$ OR$^k$, —O—X$^2$OR$^k$, —O—X$^2$NR$^k$R$^L$ and —NR$^L$—X$^2$CO$_2$R$^k$. Optionally any two R$^9$ substituents located on adjacent atoms can be combined to form a 5- to 7-membered ring optionally having from 1-3 heteroatoms selected from the group consisting of N, O and S; wherein X$^2$ is $C_{1-4}$ alkylene, $C_{1-4}$ heteroalkylene, $C_{2-4}$ alkenylene or $C_{2-4}$ alkynylene. Each R$^k$ and R$^L$ is independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-4}$ alkyl. Optionally, the groups R$^k$ and R$^L$ when attached to the same nitrogen atom can be combined to form a five or six-membered ring having from 0 to 2 additional heteroatoms as ring members. Each R$^m$ is independently a member selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-6}$ alkyl. The aliphatic portions of X$^2$, R$^k$, R$^L$ and R$^m$ are further substituted with from 0-3 members selected from the group consisting of halogen, —OH, —OR$^s$, —OC(O)NHR$^s$, —OC(O)N(R$^s$)$_2$, —SH, —SR$^s$, —S(O)R$^s$, —S(O)$_2$R$^s$, —SO$_2$NH$_2$, —S(O)$_2$NHR$^s$, —S(O)$_2$N(R$^s$)$_2$, —NHS(O)$_2$R$^s$, —NR$^s$S(O)$_2$R$^s$, —C(O)NH$_2$, —C(O)NHR$^s$, —C(O)N(R$^s$)$_2$, —C(O)R$^s$, —NHC(O)R$^s$, —NR$^s$C(O)R$^s$, —NHC(O)NH$_2$, —NR$^s$C(O)NH$_2$, —NR$^s$C(O)NHR$^s$, —NHC(O)NHR$^s$, —NR$^s$C(O)N(R$^s$)$_2$, —NHC(O)N(R$^s$)$_2$, —CO$_2$H, —CO$_2$R$^s$, —NHCO$_2$R$^s$, —NR$^s$CO$_2$R$^s$, —CN, —NO$_2$, —NH$_2$, —NHR$^s$, —N(R$^s$)$_2$, —NR$^s$S(O)NH$_2$ and —NR$^q$S(O)$_2$NHR$^s$, wherein each R$^s$ is independently an unsubstituted C$_{1-6}$ alkyl; and the symbol U is independently selected from the group consisting of —R$^m$, —CN, —CO$_2$R$^k$ and —NO$_2$. The subscript p, in formula I, is an integer from 0-1. In one embodiment, the subscript p in formula I is 1.

In some embodiments of the invention, the substituent Ar in formulae I is an optionally substituted phenyl ring. The substituents for the phenyl ring is selected from the group consisting of hydroxy, halogen, cyano, —R$^m$, —NO$_2$, —C(O)NR$^k$R$^L$, —C(O)R$^k$, —NR$^k$S(O)$_2$R$^m$, —NR$^k$R$^L$, —OR$^m$, and —NR$^L$C(O)R$^k$. Within certain aspects of this embodiment, the Ar group is a phenyl ring having the formula

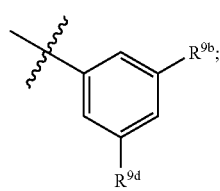

ia wherein R$^{9b}$ and R$^{9d}$ are selected from the group consisting of hydroxy, halogen, cyano, —R$^m$, —NO$_2$, —C(O)NR$^k$R$^L$, —C(O)R$^k$, —NR$^k$S(O)$_2$R$^m$, —NR$^k$R$^L$, —OR$^m$, —NR$^L$C(O)R$^k$, —SR$^k$, and —CO$_2$R$^k$. Within certain other aspects of this embodiment, the Ar group is a phenyl ring having the formula

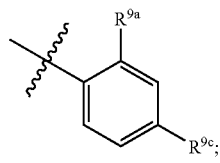

ib wherein R$^{9a}$ and R$^{9c}$ are selected from the group consisting of hydroxy, halogen, cyano, R$^m$, —NO$_2$, —C(O)NR$^k$R$^L$, —C(O)R$^k$, —NR$^k$S(O)$_2$R$^m$, —NR$^k$R$^L$, —OR$^m$, —NR$^L$C(O)R$^k$, —SR$^k$, and —CO$_2$R$^k$. Within certain other aspects of this embodiment, the Ar group is a phenyl ring having the formula

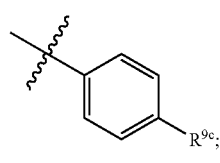

ic wherein R$^{9c}$ is selected from the group consisting of hydroxy, halogen, cyano, R$^m$, —NO$_2$, —C(O)NR$^k$R$^L$, —C(O)R$^k$, —NR$^k$S(O)$_2$R$^m$, —NR$^k$R$^L$, —OR$^m$, —NR$^L$C(O)R$^k$, —SR$^k$, and —CO$_2$R$^k$. Within certain other aspects of this embodiment, the Ar group is an optionally substituted phenyl ring selected from the group consisting of:

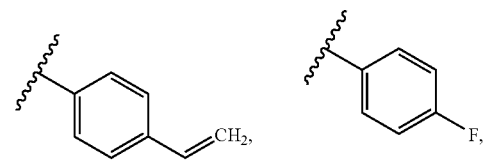
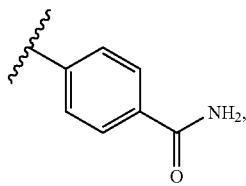
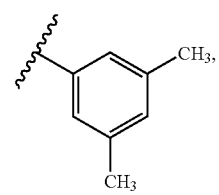
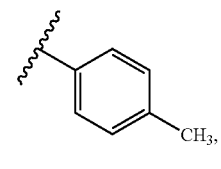
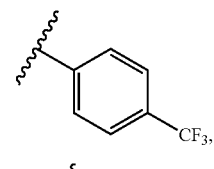
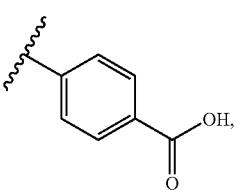
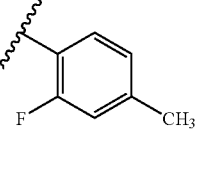
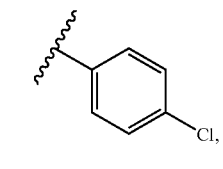
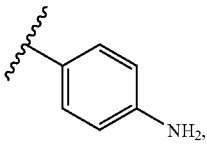
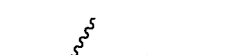
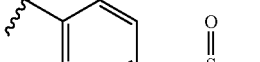
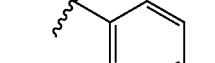
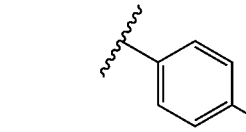

-continued

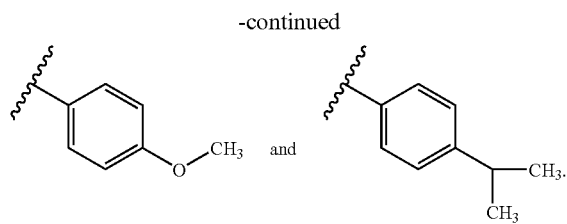

In another embodiment the Ar group in formula I is selected from the group consisting of:

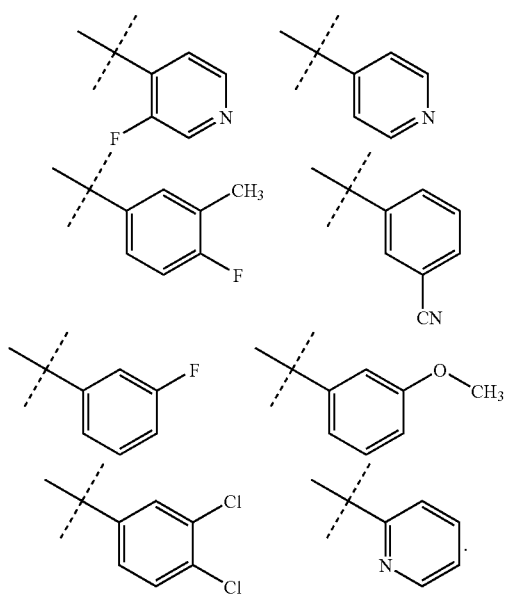

In yet another embodiment of the invention, the Ar group in formula I is an optionally substituted heteroaryl ring selected from the group consisting of 2-quinolinyl, 1-isoquinolinyl, 2-pyridyl, 3-pyridyl, 4-pyridyl, 4-pyrimidinyl, 3-quinolinyl, 5-indolyl and 2-benzofuranyl. In certain aspects of this embodiment, the Ar group is selected from the group consisting of

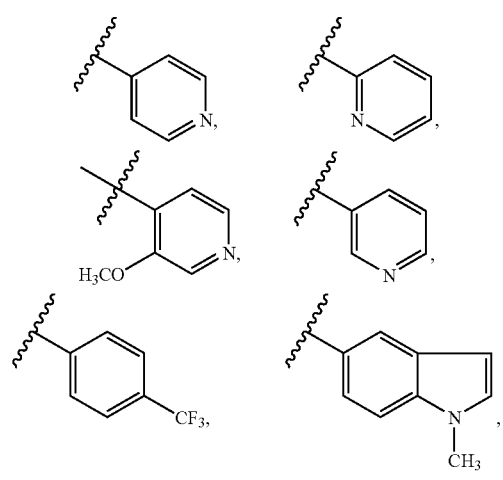

The Ar group in formula I can be attached to the remainder of the molecule through any of the ring vertex positions of fused 6-membered aryl, heteroaryl, cycloalkyl or heterocycloalkyl ring system in formula I.

In some embodiments of the invention, the $R^1$, $R^2$, $R^3$ and $R^4$ substituents in formula I are each independently selected from the group consisting of hydrogen and $C_{1-8}$ alkyl, wherein the aliphatic portions of $R^1$-$R^4$ are independently substituted with from 0-3 substituents selected from the group consisting of —OH, —OR'", —OC(O)NHR'", —OC(O)N(R'")$_2$, —SH, —SR'", —S(O)R'", —S(O)$_2$R'", —SO$_2$NH$_2$, —S(O)$_2$NHR'", —S(O)$_2$N(R'")$_2$, —NHS(O)$_2$R'", —NR'"S(O)$_2$R'", —C(O)NH$_2$, —C(O)NHR'", —C(O)N(R'")$_2$, —C(O)R'", —NHC(O)R'", —NR'"C(O)R'", —NHC(O)NH$_2$, —NR'"C(O)NH$_2$, —NR'"C(O)NHR'", —NHC(O)NHR'", —NR'"C(O)N(R'")$_2$, —NHC(O)N(R'")$_2$, —CO$_2$H, —CO$_2$R'", —NHCO$_2$R'", —NR'"CO$_2$R'", —CN, —NO$_2$, —NH$_2$, —NHR'", —N(R'")$_2$, —NR'"S(O)NH$_2$ and —NR'"S(O)$_2$NHR'".

In some embodiments of the invention, $R^5$ and $R^6$, in formula I are each independently selected from the group consisting of hydrogen, $C_{1-8}$ alkyl, $C_{1-8}$ haloalkyl, $C_{2-8}$ alkenyl, $C_{2-8}$ alkynyl and $C_{3-8}$ cycloalkyl, or optionally $R^5$ and $R^6$ are combined to form a 5- to 10-membered heterocycloalkyl ring; wherein the aliphatic portions of $R^5$ and $R^6$ are substituted with from 0-3 substituents selected from the group consisting of, —OH, —OR", —OC(O)NHR", —OC(O)N(R")$_2$, —SH, —SR", —S(O)R", —S(O)$_2$R", —SO$_2$NH$_2$, —S(O)$_2$NHR", —S(O)$_2$N(R")$_2$, —NHS(O)$_2$R", —NR"S(O)$_2$R", —C(O)NH$_2$, —C(O)NHR", —C(O)N(R")$_2$, —C(O)R", —NHC(O)R", —NR"C(O)R", —NHC(O)NH$_2$, —NR"C(O)NH$_2$, —NR"C(O)NHR", —NHC(O)NHR", —NR"C(O)N(R")$_2$, —NHC(O)N(R")$_2$, —CO$_2$H, —CO$_2$R", —NHCO$_2$R", —NR"CO$_2$R", —CN, —NO$_2$, —NH$_2$, —NHR", —N(R")$_2$, —NR"S(O)NH$_2$ and —NR"S(O)$_2$NHR". In certain aspects of this embodiment, $R^5$ is an optionally substituted member selected from the group consisting of $C_{1-8}$ alkyl, $C_{2-8}$ alkenyl and $C_{2-8}$ alkynyl; and $R^6$ is an optionally substituted $C_{3-10}$ membered cycloalkyl ring. In another aspect of this embodiment, $R^5$ is methyl, ethyl, n-propyl, isopropyl, isobutyl, tert-butyl or n-butyl; and $R^6$ is cyclopentyl, cyclohexyl, cycloheptyl or cyclooctyl. In yet another aspect of this embodiment, the $R^5$ and $R^6$ groups are combined to form a 5- to 10-membered ring system having from 1-3 heteroatoms selected from the group consisting of N, O and S. In another aspect of this embodiment, —NR$^5$R$^6$ group is selected from the group consisting of

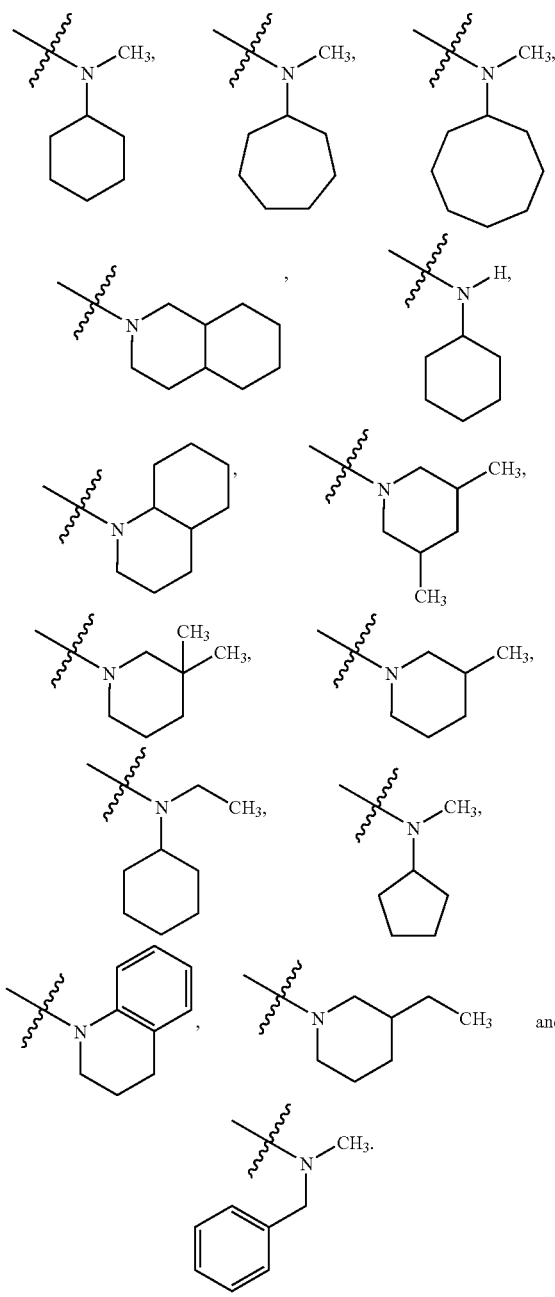

In some embodiments, the symbol Z, in formula I, is selected from the group consisting of —CONR$^b$— and —NR$^b$C(O)—, wherein R$^b$ is selected from the group consisting of hydrogen, C$_{1-8}$ acyl, C$_{1-8}$ alkyl-S(O)$_2$—, C$_{1-8}$ alkyl, C$_{1-8}$ haloalkyl, C$_{2-8}$ heteroalkyl, C$_{3-6}$ cycloalkyl, C$_{2-8}$ alkenyl, C$_{2-8}$ alkynyl, aryl, heteroaryl and aryl-C$_{1-4}$ alkyl; and wherein the aliphatic portions of the linking group Z are substituted with from 0-3 substituents selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O) R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$.

In some embodiments, subscript p, in formula I, is 0 and R$^7$ is selected from the group consisting of halogen, cyano, —R$^j$, —OR$^h$, —NO$_2$ and —CO$_2$R$^h$.

Figure 1B:
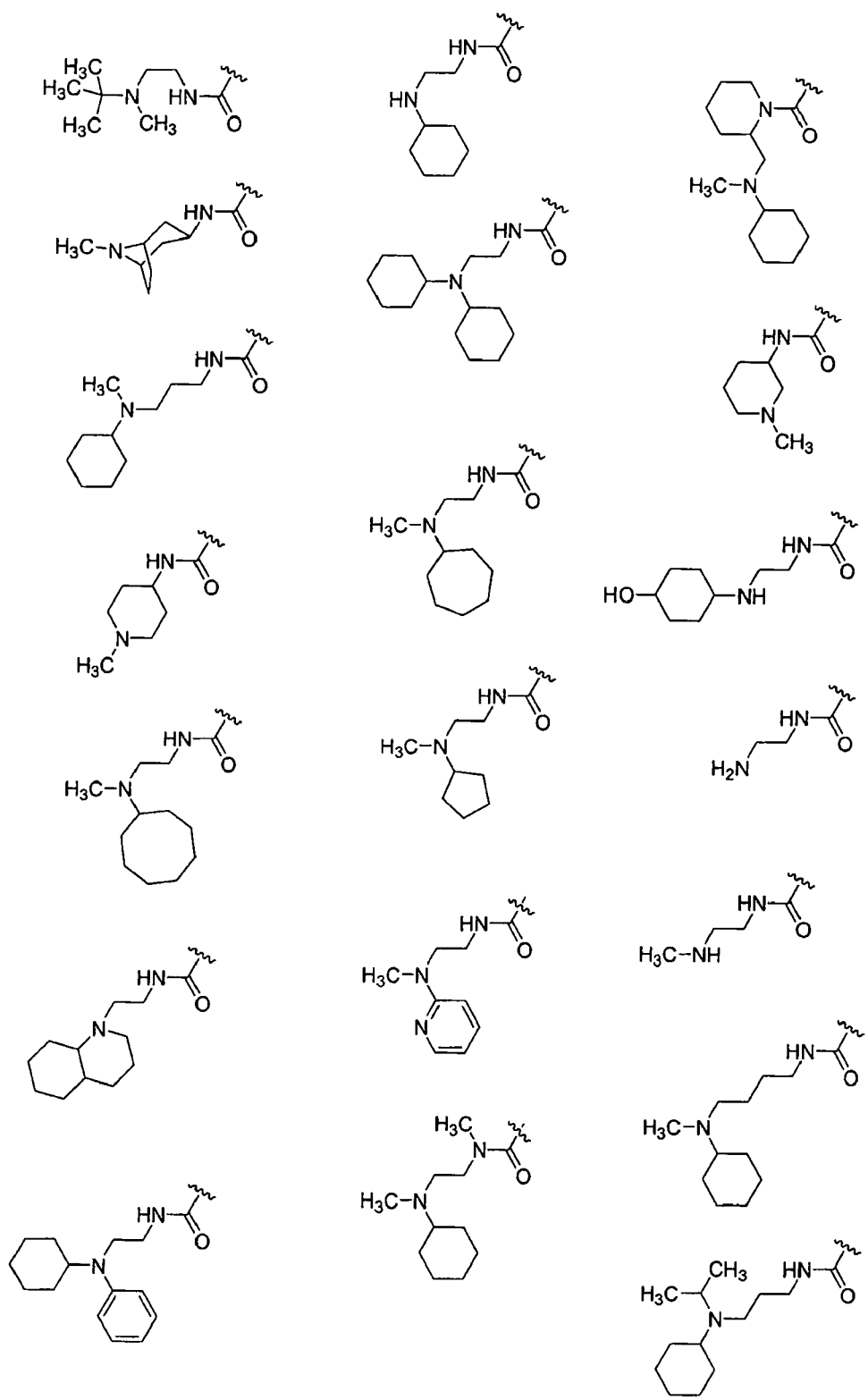
Figure 1C:
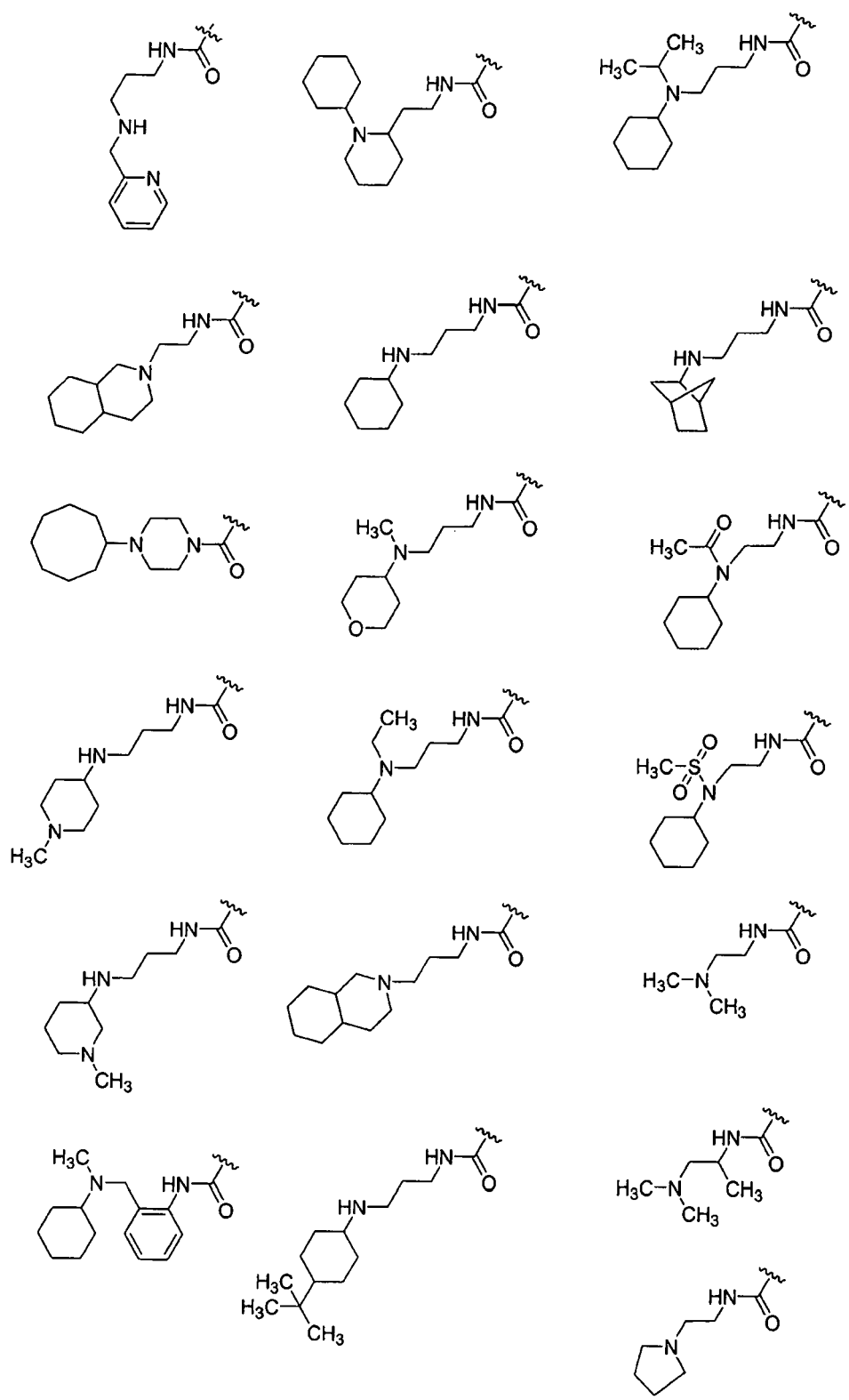
Figure 1D:
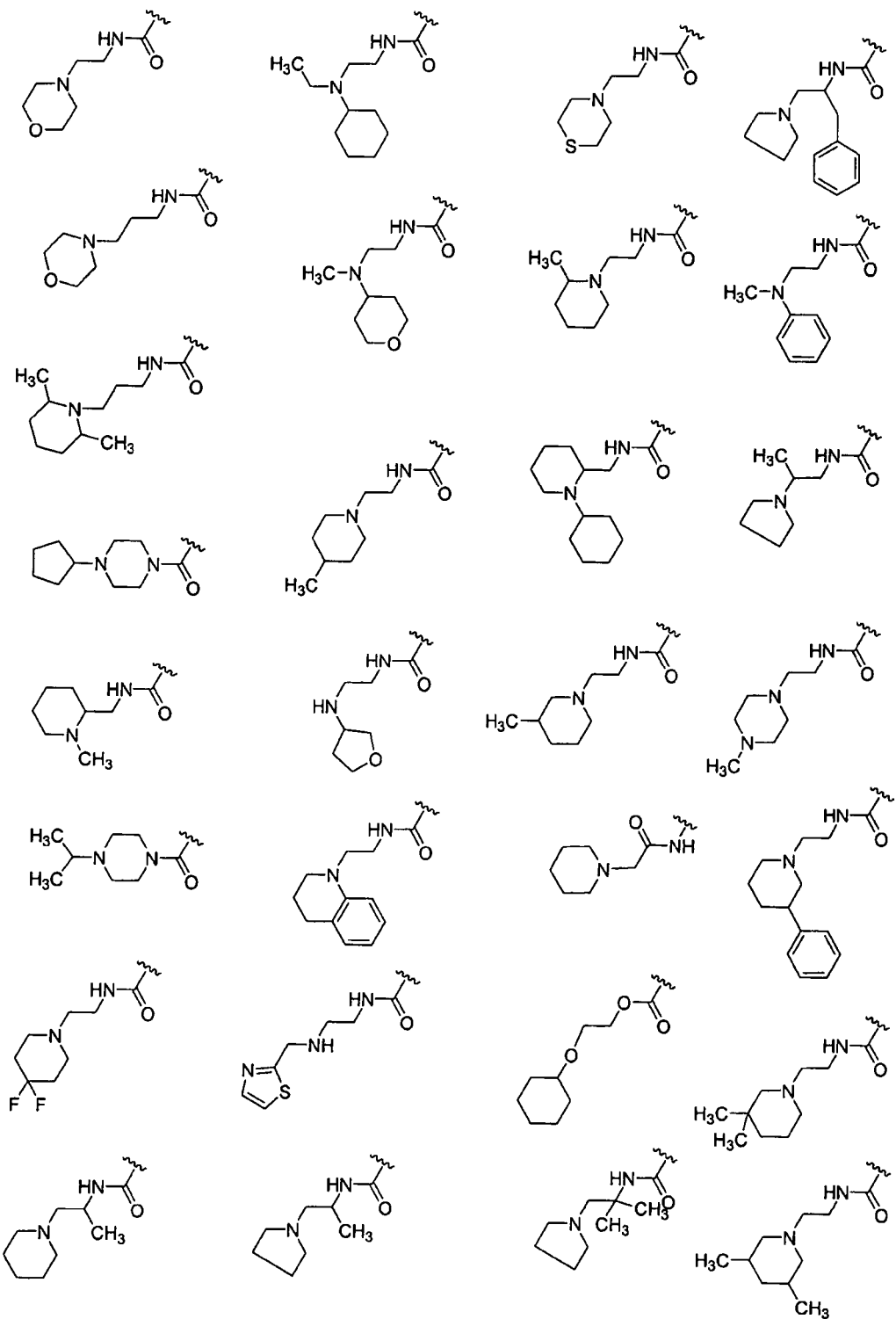

In some embodiments, the group R$^5$R$^6$N—(CR$^3$R$^4$)$_n$Z-, in formulae I is selected from the group as set forth in FIGS. 1a to 1d.

It should be readily apparent to a skilled artisan that any combination of the groups set forth above for compounds having formula I would form additional preferred embodiments that are also within the scope of the invention.

In one embodiment, compounds of the invention have a formula selected from

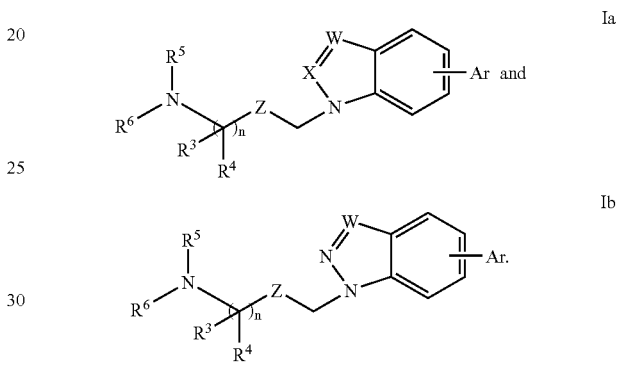

In formulae Ia and Ib, the substituents R$^3$ and R$^4$ at each occurrence is independently selected from the group consisting of hydrogen, halogen and C$_{1-8}$ alkyl. The substituents R$^5$ and R$^6$ are each independently selected from the group consisting of hydrogen, C$_{1-8}$ alkyl, C$_{3-10}$ cycloalkyl, C$_{3-10}$ heterocycloalkyl, C$_{1-8}$ acyl, C$_{1-8}$ alkyl-S(O)$_2$—, aryl, heteroaryl, aryl-C$_{1-6}$ alkyl and aryl-C$_{1-6}$ heteroalkyl. Optionally, R$^3$ and R$^5$ or R$^5$ and R$^6$ are combined to form a 5- to 10-membered ring system having from 1-3 additional heteroatoms selected from the group consisting of N, O and S. In formula Ia and Ib, the symbols W and X are each independently selected from the group consisting of CH, CR$^8$ and C(L$^1$R$^8$). The symbol Z represents a group selected from the group consisting of —CONR$^b$— and —NR$^b$C(O)—. The subscript n is an integer from 2-4. The Ar group in formula Ia and Ib is an optionally substituted member selected from the group consisting of phenyl, pyridyl, pyrimidinyl, benzofuranyl, quinolinyl, isoquinolinyl and indolyl.

In a second embodiment, compounds of the invention have a formula selected from

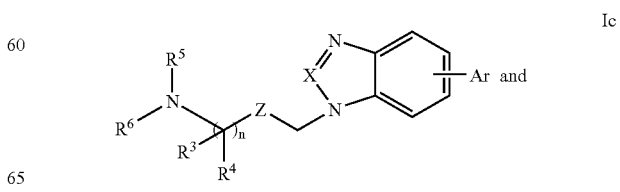

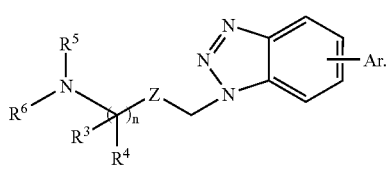

In formulae Ic and Id, the substituents $R^3$ and $R^4$ at each occurrence is independently selected from the group consisting of hydrogen, halogen or $C_{1-8}$ alkyl. The substituents $R^5$ and $R^6$ are each independently selected from the group consisting of hydrogen, $C_{1-8}$ alkyl, $C_{3-10}$ cycloalkyl, $C_{3-10}$ -heterocycloalkyl, $C_{1-8}$ acyl, $C_{1-8}$ alkyl-$S(O)_2$—, aryl, heteroaryl, aryl-$C_{1-6}$ alkyl and aryl-$C_{1-6}$ heteroalkyl. Optionally $R^3$ and $R^5$ or $R^5$ and $R^6$ are combined to form a 5- to 10-membered ring system having from 1-3 heteroatoms selected from the group consisting of N, O and S. The symbol X is selected from the group consisting of CH, $CR^8$, or $C(L^1R^8)$. In certain embodiments, the symbol X is CH or $CR^8$ wherein in $R^8$ is $C_{1-6}$ alkyl, $C_{1-6}$ haloalkyl, phenyl, pyridyl, pyrimidinyl or halogen. The symbol Z is a linking group selected from the group consisting of —$CONR^b$— and —$NR^bC(O)$—. The subscript n is an integer from 2-4. The Ar group is an optionally substituted group selected from the group consisting of phenyl, pyridyl, pyrimidinyl, benzofuranyl, quinolinyl, isoquinolinyl and indolyl.

In a third embodiment, compounds of the invention have a formula selected from

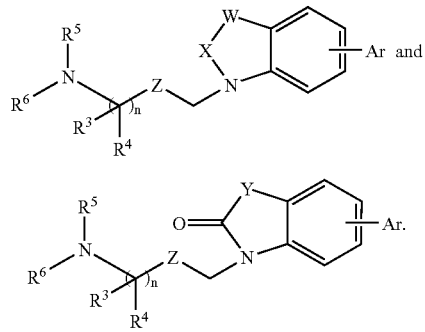

In formula Ie and If, $R^3$ and $R^4$ at each occurrence is independently selected from the group consisting of hydrogen, halogen and $C_{1-8}$ alkyl. The substituents $R^5$ and $R^6$ are each independently selected from the group consisting of hydrogen, $C_{1-8}$ alkyl, $C_{3-10}$ cycloalkyl, $C_{3-10}$ heterocycloalkyl, $C_{1-8}$ acyl, $C_{1-8}$ alkyl-$S(O)_2$—, aryl, heteroaryl, aryl-$C_{1-6}$ alkyl and aryl-$C_{1-6}$ heteroalkyl. Optionally, $R^3$ and $R^5$ or $R^5$ and $R^6$ are combined to form a 5- to 10-membered ring system having from 1-3 heteroatoms selected from the group consisting of N, O and S. The symbols W and X are each independently selected from the group consisting of —$CH_2$—, —$C(R^8)_2$—, —$CH(R^8)$—, —$C(L^1R^8)(R^8)$— and —$CH(L^1R^8)$—. The symbol Y is selected from the group consisting of —NH—, —$NR^8$—, $NL^1R^8$—, —$CH_2$—, —$C(R^8)_2$—, —$CH(R^8)$—, —$C(L^1R^8)(R^8)$—, —CH($L^1R^8$)— and —O—. The symbol Z represents a group selected from the group consisting of —$CONR^b$— and —$NR^bC(O)$—. The subscript n is an integer from 2-4; and Ar is an optionally substituted group selected from the group consisting of phenyl, pyridyl, pyrimidinyl, benzofuranyl, quinolinyl, isoquinolinyl and indolyl.

In some embodiments, the Ar group in formula Ia-If can be attached to the remainder of the molecule through any of the ring vertex positions of the fused benzene ring in formula Ia-If. For example, the Ar group in formula Ia-If can be attached to the fused benzene ring at the 4, 5, 6 or 7 position of said ring. For illustrative purposes, the ring vertex positions of the fused benzene ring represented in formula Ia-If are numbered and shown below:

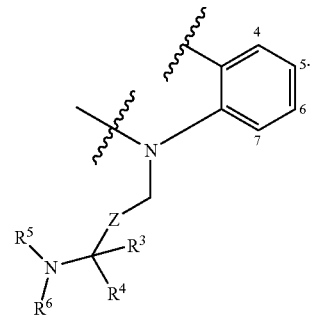

In one embodiment of the invention, the Ar group of formulae Ia-If is attached to the remainder of the molecule at the 4 position of said benzene ring. In another embodiment, the Ar group of formulae Ia-If is attached to the remainder of the molecule at the 5 position of said fused benzne ring. In another embodiment, the Ar group of formulae Ia-If is attached to the remainder of the molecule at the 6 position of said fused benzene ring. In another embodiment, the Ar group of formulae Ia-if is attached to the remainder of the molecule at the 7 position of said fused benzene ring. Preferably, the Ar group is attached to the remainder of the molecule, in formulae Ia-If, at the 4 or 6 position of said fused benzene ring.

In another embodiment, the present invention provides for compounds of formula I and subformulae (Ia-If) that comprise one or more radioisotopic atoms. These radioactive variants of formula I are useful for radioimaging and radiotherapy purposes, especially in cancer diagnostics and therapies.

In one embodiment, one or more atoms in a compound of formula I is replaced with a radioactive atom. In one aspect of this embodiment, the radioactive atom in formula I is a radioactive bromine, such as, bromine-76 and bromine-77. A bromine-76 compound can be used for PET (Positron Emission Tomography) radioimaging, while a bromine-77 compound can be used for radiotherapy. In another aspect of this embodiment, the radioactive atom is radioactive iodine, such as, iodine-123, iodine-124, or iodine-131. An iodine-123 labeled compound can be used for SPECT (Single Photon Emission Compute Tomography) radioimaging, an iodine 124 labeled compound can be used for both PET radioimaging and/or radiotherapy and an iodine-131 labeled compound can be used for radiotherapy. In particular, the iodine-124 radioisotope is becoming increasingly significant in PET diagnostic use. It decays (t1/2=4.2 days) simultaneously by positron emission (25.6%) and by electron capture (74.4%). Due to its quantity of short-range Auger electrons (9.2/decay) it has the potential to be a therapeutic nuclide. The substantially longer half-life of this isotope, as compared with the other optional radioisotopes considered, enables a prolonged follow-up after injection of a radiolabeled agent. In yet another aspect of this embodiment, the radioactive atom in formula I is a radioactive fluorine, and the radioactive fluorine is fluorine-18.

In another embodiment, a compound of formula I can be conjugated to a chelating group that is capable of chelating to a radioactive atom, such as, for example, Actinium-225, Bismut-212, Bismut-213, Lead-203, Copper-64, Copper-67, Gallium-66, Gallium-67, Gallium-68, Lutetium-177, Indium-111, Indium-113, Yttrium-86 and Yttrium-90, Dysprosium 162, Dysprosium 165, Dysprosium 167, Holmium-166, Praseodymium-142, Praseodymium-143, Promethium-149, and Terbium-149, to form a radioactive variant of formula I. Chelating groups that are useful in the present invention for chelating to the above-listed radioactive atoms include, but are not limited to, 1-(1,3-carboxy-propyl)-4,7,10-(carboxymethyl)-1,4,7,10-tetraazacyclododec-ane (chelator DOTAGA), 1-(1,2-carboxyethyl)-4,7,10-(carboxymethyl)-1,4,7,10-tetraazacyclododecane (chelator DOTASA) or 1,4,7,10-tetraazaacyclo-dodecane-1,4,7,10-tetra-acetic acid (chelator DOTA), among others. The chelating agent can be conjugated, for example, to a substituent (e.g., an —OH, —NH$_2$) located on the

ring, the

ring or the Ar group in formula I. Preferably, the chelating group is attached to a compound of formula I through a linking group, such as, for example, a $C_{1-10}$ alkyl, $C_{1-10}$ heteroalkyl linker.

A family of preferred compounds of the invention having formula I is set forth in Table 1.

TABLE 1

1. N-[2-(Cyclohexyl-methyl-amino)-ethyl]-2-indazol-1-yl-acetamide
2. N-[2-(Cyclohexyl-methyl-amino)-ethyl]-2-(3a,4,5,6,7,7a-hexahydro-indazol-1-yl)-acetamide
3. N-[2-(Cyclohexyl-methyl-amino)-ethyl]-2-pyrazolo[3,4-b]pyridin-1-yl-acetamide
4. 2-(3-Chloro-pyrazolo[3,4-b]pyridin-1-yl)-N-[2-(cyclohexyl-methyl-amino)-ethyl]-acetamide
5. N-[2-(Cyclohexyl-methyl-amino)-ethyl]-2-(3a,6,7,7a-tetrahydro-4H-pyrano[4,3-c]pyrazol-1-yl)-acetamide
6. N-[2-(Cyclohexyl-methyl-amino)-ethyl]-2-(3-methyl-indazol-1-yl)-acetamide
7. N-[2-(Cyclohexyl-methyl-amino)-ethyl]-2-indazol-2-yl-acetamide
8. N-[2-(Cyclohexyl-methyl-amino)-ethyl]-2-(5,7-dimethyl-4,6-dioxo-4,5,6,7-tetrahydro-pyrazolo[3,4-d]pyrimidin-2-yl)-acetamide
9. N-[2-(Cyclohexyl-methyl-amino)-ethyl]-2-(2-methyl-benzoimidazol-1-yl)-acetamide
10. N-[2-(Cyclohexyl-methyl-amino)-ethyl]-2-(2-ethyl-benzoimidazol-1-yl)-acetamide
11. N-[2-(Cyclohexyl-methyl-amino)-ethyl]-2-(2-isopropyl-benzoimidazol-1-yl)-acetamide
12. N-[2-(Cyclohexyl-methyl-amino)-ethyl]-2-(2-trifluoromethyl-benzoimidazol-1-yl)-acetamide
13. N-[2-(Cyclohexyl-methyl-amino)-ethyl]-2-(2-pyridin-2-yl-benzoimidazol-1-yl)-acetamide
14. N-[2-(Cyclohexyl-methyl-amino)-ethyl]-2-(2-phenyl-benzoimidazol-1-yl)-acetamide
15. 2-(2-Chloro-benzoimidazol-1-yl)-N-[2-(cyclohexyl-methyl-amino)-ethyl]-acetamide
16. N-[2-(Cyclohexyl-methyl-amino)-ethyl]-2-imidazo[4,5-b]pyridin-1-yl-acetamide
17. N-[2-(Cyclohexyl-methyl-amino)-ethyl]-2-imidazo[4,5-b]pyridin-3-yl-acetamide
18. 2-(4-Chloro-2-methyl-benzoimidazol-1-yl)-N-[2-(cyclohexyl-methyl-amino)-ethyl]-acetamide
19. N-[2-(Cyclohexyl-methyl-amino)-ethyl]-2-(4,5-difluoro-benzoimidazol-1-yl)-acetamide
20. 2-(5-Chloro-benzoimidazol-1-yl)-N-[2-(cyclohexyl-methyl-amino)-ethyl]-acetamide
21. N-[2-(Cyclohexyl-methyl-amino)-ethyl]-2-(5-methyl-benzoimidazol-1-yl)-acetamide
22. N-[2-(Cyclohexyl-methyl-amino)-ethyl]-2-(5-methoxy-benzoimidazol-1-yl)-acetamide
23. 2-(4-Chloro-pyrazolo[4,3-c]pyridin-1-yl)-N-[2-(cyclohexyl-methyl-amino)-ethyl]-acetamide
24. 2-(7-Chloro-1H-pyrrolo[2,3-c]pyridin-3-yl)-N-[2-(cyclohexyl-methyl-amino)-ethyl]-acetamide
25. N-[2-(Cyclohexyl-methyl-amino)-ethyl]-3-(1H-indol-3-yl)-propionamide
26. 2-(6-Chloro-benzoimidazol-1-yl)-N-[2-(cyclohexyl-methyl-amino)-ethyl]-acetamide
27. N-[2-(Cyclohexyl-methyl-amino)-ethyl]-2-(7-trifluoromethyl-indazol-1-yl)-acetamide
28. N-[2-(Cyclohexyl-methyl-amino)-ethyl]-2-(5-methyl-4-oxo-4,5-dihydro-pyrazolo[4,3-c]pyridin-1-yl)-acetamide
29. N-[2-(Cyclohexyl-methyl-amino)-ethyl]-2-indol-1-yl-acetamide TABLE 1-continued 30. 2-Benzotriazol-1-yl-N-[2-(cyclohexyl-methyl-amino)-ethyl]-acetamide
31. N-[2-(Cyclohexyl-methyl-amino)-ethyl]-2-(7-nitro-indol-1-yl)-acetamide
32. 2-(7-Benzyloxy-indol-1-yl)-N-[2-(cyclohexyl-methyl-amino)-ethyl]-acetamide
33. N-[2-(Cyclohexyl-methyl-amino)-ethyl]-2-(7-methyl-indol-1-yl)-acetamide
34. N-[2-(Cyclohexyl-methyl-amino)-ethyl]-2-(7-methoxy-indol-1-yl)-acetamide
35. N-[2-(Cyclohexyl-methyl-amino)-ethyl]-2-[7-(4-fluoro-phenyl)-indol-1-yl]-acetamide
36. N-[2-(Cyclohexyl-methyl-amino)-ethyl]-2-(7-ethyl-indol-1-yl)-acetamide
37. N-[2-(Cyclohexyl-methyl-amino)-ethyl]-2-(5,6-dichloro-benzoimidazol-1-yl)-acetamide
38. N-[2-(Cyclohexyl-methyl-amino)-ethyl]-2-(4-fluoro-indol-1-yl)-acetamide
39. N-[2-(Cyclohexyl-methyl-amino)-ethyl]-2-(4-oxo-4,5,6,7-tetrahydro-indol-1-yl)-acetamide
40. 2-(7-Bromo-indol-1-yl)-N-[2-(cyclohexyl-methyl-amino)-ethyl]-acetamide
41. N-[2-(Cyclohexyl-methyl-amino)-ethyl]-2-(7-phenyl-indol-1-yl)-acetamide
42. N-[3-(Cyclohexyl-methyl-amino)-propyl]-2-[7-(4-fluoro-phenyl)-indol-1-yl]-acetamide
43. 2-[7-(4-Fluoro-phenyl)-indol-1-yl]-N-[2-(octahydro-quinolin-1-yl)-ethyl]-acetamide
44. N-[2-(Cyclohexyl-methyl-amino)-ethyl]-2-[7-(4-methoxy-phenyl)-indol-1-yl]-acetamide
45. N-[2-(Cyclohexyl-methyl-amino)-ethyl]-2-[7-(4-trifluoromethyl-phenyl)-indol-1-yl]-acetamide
46. N-[2-(Cyclohexyl-methyl-amino)-ethyl]-2-(7-p-tolyl-indol-1-yl)-acetamide
47. 2-[7-(4-Chloro-phenyl)-indol-1-yl]-N-[2-(cyclohexyl-methyl-amino)-ethyl]-acetamide
48. N-[2-(Cyclohexyl-methyl-amino)-ethyl]-2-[7-(3,4-dichloro-phenyl)-indol-1-yl]-acetamide
49. N-[2-(Cyclohexyl-methyl-amino)-ethyl]-2-(7-pyridin-3-yl-indol-1-yl)-acetamide
50. N-[2-(Cyclohexyl-methyl-amino)-ethyl]-2-(7-pyridin-4-yl-indol-1-yl)-acetamide
51. N-[2-(Cyclohexyl-methyl-amino)-ethyl]-2-(7-pyrimidin-5-yl-indol-1-yl)-acetamide
52. 2-[7-(3-Cyano-phenyl)-indol-1-yl]-N-[2-(cyclohexyl-methyl-amino)-ethyl]-acetamide
53. N-[2-(Cyclohexyl-methyl-amino)-ethyl]-2-(6-phenyl-indol-1-yl)-acetamide
54. N-[2-(Cyclohexyl-methyl-amino)-ethyl]-2-[6-(4-fluoro-phenyl)-indol-1-yl]-acetamide
55. N-[2-(Cyclohexyl-methyl-amino)-ethyl]-2-(6-p-tolyl-indol-1-yl)-acetamide
56. N-[2-(Cyclohexyl-methyl-amino)-ethyl]-2-[6-(4-trifluoromethyl-phenyl)-indol-1-yl]-acetamide
57. N-[2-(Cyclohexyl-methyl-amino)-ethyl]-2-[6-(4-methoxy-phenyl)-indol-1-yl]-acetamide
58. 2-(6-Bromo-indol-1-yl)-N-[2-(cyclohexyl-methyl-amino)-ethyl]-acetamide
59. N-[2-(Cyclohexyl-methyl-amino)-ethyl]-2-[7-(3-fluoro-phenyl)-indol-1-yl]-acetamide
60. N-[2-(Cyclohexyl-methyl-amino)-ethyl]-2-[7-(3-methoxy-phenyl)-indol-1-yl]-acetamide
61. N-[2-(Cyclohexyl-methyl-amino)-ethyl]-2-[6-(3,4-dichloro-phenyl)-indol-1-yl]-acetamide
62. N-[2-(Cyclohexyl-methyl-amino)-ethyl]-2-[6-(3-methoxy-phenyl)-indol-1-yl]-acetamide
63. N-[2-(Cyclohexyl-methyl-amino)-ethyl]-2-[6-(3-fluoro-phenyl)-indol-1-yl]-acetamide
64. 2-[6-(4-tert-Butyl-phenyl)-indol-1-yl]-N-[2-(cyclohexyl-methyl-amino)-ethyl]-acetamide
65. 2-[6-(3-Cyano-phenyl)-indol-1-yl]-N-[2-(cyclohexyl-methyl-amino)-ethyl]-acetamide
66. 2-[6-(4-Chloro-phenyl)-indol-1-yl]-N-[2-(cyclohexyl-methyl-amino)-ethyl]-acetamide
67. N-[2-(Cyclohexyl-methyl-amino)-ethyl]-2-(6-o-tolyl-indol-1-yl)-acetamide
68. 2-[6-(3,5-Bis-trifluoromethyl-phenyl)-indol-1-yl]-N-[2-(cyclohexyl-methyl-amino)-ethyl]-acetamide
69. 2-[6-(4-Butyl-phenyl)-indol-1-yl]-N-[2-(cyclohexyl-methyl-amino)-ethyl]-acetamide
70. N-[2-(Cyclohexyl-methyl-amino)-ethyl]-2-[6-(3,5-dimethyl-phenyl)-indol-1-yl]-acetamide
71. N-[2-(Cyclohexyl-methyl-amino)-ethyl]-2-[6-(4-fluoro-3-methyl-phenyl)-indol-1-yl]-acetamide
72. N-[2-(Cyclohexyl-methyl-amino)-ethyl]-2-[6-(4-isopropoxy-phenyl)-indol-1-yl]-acetamide
73. N-[2-(Cyclohexyl-methyl-amino)-ethyl]-2-(1-methyl-1H-[4,6']biindolyl-1'-yl)-acetamide
74. N-[2-(Cyclohexyl-methyl-amino)-ethyl]-2-(6-quinolin-4-yl-indol-1-yl)-acetamide
75. 2-(6-Benzofuran-3-yl-indol-1-yl)-N-[2-(cyclohexyl-methyl-amino)-ethyl]-acetamide TABLE 1-continued 76. N-[2-(Cyclohexyl-methyl-amino)-ethyl]-2-[6-(4-ethyl-phenyl)-indol-1-yl]-acetamide
77. N-[2-(Cyclohexyl-methyl-amino)-ethyl]-2-[6-(4-isopropyl-phenyl)-indol-1-yl]-acetamide
78. N-[2-(Cyclohexyl-methyl-amino)-ethyl]-2-(6-m-tolyl-indol-1-yl)-acetamide
79. N-[2-(Cyclohexyl-methyl-amino)-ethyl]-2-(6-pyridin-4-yl-indol-1-yl)-acetamide
80. N-[2-(Cyclohexyl-methyl-amino)-ethyl]-2-(6-pyridin-3-yl-indol-1-yl)-acetamide
81. N-[2-(Cyclohexyl-methyl-amino)-ethyl]-2-(6-pyrimidin-5-yl-indol-1-yl)-acetamide
82. N-[2-(Cyclohexyl-methyl-amino)-ethyl]-2-(5-p-tolyl-indol-1-yl)-acetamide
83. N-[2-(Cyclohexyl-methyl-amino)-ethyl]-2-[5-(4-fluoro-phenyl)-indol-1-yl]-acetamide
84. N-[2-(Cyclohexyl-methyl-amino)-ethyl]-2-(4-methyl-indol-1-yl)-acetamide
85. N-[2-(Cyclohexyl-methyl-amino)-ethyl]-2-(4-fluoro-indol-1-yl)-acetamide
86. N-[2-(Octahydro-quinolin-1-yl)-ethyl]-2-(6-p-tolyl-indol-1-yl)-acetamide
87. N-[2-(Cyclohexyl-methyl-amino)-ethyl]-2-[6-(4-vinyl-phenyl)-indol-1-yl]-acetamide
88. N-[2-(Cyclohexyl-methyl-amino)-ethyl]-2-[6-(3,4-dimethyl-phenyl)-indol-1-yl]-acetamide
89. N-[2-(Cyclohexyl-methyl-amino)-ethyl]-2-[6-(2-fluoro-4-methyl-phenyl)-indol-1-yl]-acetamide
90. N-[2-(Cyclohexyl-methyl-amino)-ethyl]-2-[6-(3-fluoro-4-methyl-phenyl)-indol-1-yl]-acetamide
91. N-[2-(Cyclohexyl-methyl-amino)-ethyl]-2-(6-p-tolyl-indazol-1-yl)-acetamide
92. N-[2-(Cyclohexyl-methyl-amino)-ethyl]-2-[6-(3-fluoro-pyridin-4-yl)-indol-1-yl]-acetamide
93. N-[2-(Cyclohexyl-methyl-amino)-ethyl]-2-[6-(3-methoxy-pyridin-4-yl)-indol-1-yl]-acetamide
94. 4-(1-{[2-(Cyclohexyl-methyl-amino)-ethylcarbamoyl]-methyl}-1H-indol-6-yl)-benzoic acid
95. 4-(1-{[2-(Cyclohexyl-methyl-amino)-ethylcarbamoyl]-methyl}-1H-indol-6-yl)-benzamide
96. N-[2-(Cyclopentyl-methyl-amino)-ethyl]-2-(6-p-tolyl-indol-1-yl)-acetamide
97. N-[2-(Acetyl-cyclohexyl-amino)-ethyl]-2-(6-p-tolyl-indol-1-yl)-acetamide
98. N-[2-(Cyclohexyl-methanesulfonyl-amino)-ethyl]-2-(6-p-tolyl-indol-1-yl)-acetamide
99. N-(2-Piperidin-1-yl-ethyl)-2-(6-p-tolyl-indol-1-yl)-acetamide
100. N-(2-Cyclohexylamino-ethyl)-2-(6-p-tolyl-indol-1-yl)-acetamide
101. N-(2-Dimethylamino-ethyl)-2-(6-p-tolyl-indol-1-yl)-acetamide
102. N-(2-Diethylamino-ethyl)-2-(6-p-tolyl-indol-1-yl)-acetamide
103. N-(2-Dimethylamino-1-methyl-ethyl)-2-(6-p-tolyl-indol-1-yl)-acetamide
104. N-(2-Pyrrolidin-1-yl-ethyl)-2-(6-p-tolyl-indol-1-yl)-acetamide
105. 3-(1-{[2-(Cyclohexyl-methyl-amino)-ethylcarbamoyl]-methyl}-1H-indol-6-yl)-benzamide
106. 2-(1-{[2-(Cyclohexyl-methyl-amino)-ethylcarbamoyl]-methyl}-1H-indol-6-yl)-benzamide
107. N-(2-Morpholin-4-yl-ethyl)-2-(6-p-tolyl-indol-1-yl)-acetamide
108. N-(3-Morpholin-4-yl-propyl)-2-(6-p-tolyl-indol-1-yl)-acetamide
109. N-[3-(2,6-Dimethyl-piperidin-1-yl)-propyl]-2-(6-p-tolyl-indol-1-yl)-acetamide
110. N-[3-(3-Methyl-piperidin-1-yl)-propyl]-2-(6-p-tolyl-indol-1-yl)-acetamide
111. N-[2-(Cyclohexyl-methyl-amino)-ethyl]-2-(2-oxo-5-p-tolyl-benzooxazol-3-yl)-acetamide
112. 1-(4-Cyclopentyl-piperazin-1-yl)-2-(6-p-tolyl-indol-1-yl)-ethanone
113. 1-(4-Isopropyl-piperazin-1-yl)-2-(6-p-tolyl-indol-1-yl)-ethanone
114. N-(1-Methyl-piperidin-2-ylmethyl)-2-(6-p-tolyl-indol-1-yl)-acetamide
115. N-(2-Azepan-1-yl-ethyl)-2-(6-p-tolyl-indol-1-yl)-acetamide
116. N-[2-(2,6-Dimethyl-piperidin-1-yl)-ethyl]-2-(6-p-tolyl-indol-1-yl)-acetamide
117. N-[2-(Cyclohexyl-ethyl-amino)-ethyl]-2-(6-p-tolyl-indol-1-yl)-acetamide
118. N-[2-(4-Methyl-piperidin-1-yl)-ethyl]-2-(6-p-tolyl-indol-1-yl)-acetamide
119. N-{2-[Methyl-(tetrahydro-pyran-4-yl)-amino]-ethyl}-2-(6-p-tolyl-indol-1-yl)-acetamide
120. N-{2-[Methyl-(tetrahydro-furan-3-yl)-amino]-ethyl}-2-(6-p-tolyl-indol-1-yl)-acetamide
121. N-[2-(1,2,3,4-Tetrahydro-naphthalen-1-ylamino)-ethyl]-2-(6-p-tolyl-indol-1-yl)-acetamide
122. N-{2-[(Thiazol-2-ylmethyl)-amino]-ethyl}-2-(6-p-tolyl-indol-1-yl)-acetamide
123. N-(2-Thiomorpholin-4-yl-ethyl)-2-(6-p-tolyl-indol-1-yl)-acetamide
124. N-[2-(Cyclohexyl-methyl-amino)-ethyl]-2-(6-pyridin-2-yl-indol-1-yl)-acetamide
125. 2-[6-(2-Amino-phenyl)-indol-1-yl]-N-[2-(cyclohexyl-methyl-amino)-ethyl]-acetamide
126. N-[2-(Cyclohexyl-methyl-amino)-ethyl]-2-[6-(4-morpholin-4-yl-phenyl)-indol-1-yl]-acetamide
127. N-[2-(Cyclohexyl-methyl-amino)-ethyl]-2-[6-(4-methanesulfonylamino-phenyl)-indol-1-yl]-acetamide
128. 2-[6-(4-Acetylamino-phenyl)-indol-1-yl]-N-[2-(cyclohexyl-methyl-amino)-ethyl]-acetamide TABLE 1-continued 129. 2-[6-(4-Cyano-phenyl)-indol-1-yl]-N-[2-(cyclohexyl-methyl-amino)-ethyl]-acetamide
130. N-(1-Cyclohexyl-piperidin-2-ylmethyl)-2-(6-p-tolyl-indol-1-yl)-acetamide
131. 2-Piperidin-1-yl-N-[2-(6-p-tolyl-indol-1-yl)-ethyl]-acetamide
132. 1-{[2-(Cyclohexyl-methyl-amino)-ethylcarbamoyl]-methyl}-6-p-tolyl-1H-indole-2-carboxylic acid methyl ester
133. 1-{[2-(Cyclohexyl-methyl-amino)-ethylcarbamoyl]-methyl}-6-p-tolyl-1H-indole-2-carboxylic acid
134. N-(1-Methyl-2-piperidin-1-yl-ethyl)-2-(6-p-tolyl-indol-1-yl)-acetamide
135. N-(1-Methyl-2-pyrrolidin-1-yl-ethyl)-2-(6-p-tolyl-indol-1-yl)-acetamide
136. N-(1,1-Dimethyl-2-pyrrolidin-1-yl-ethyl)-2-(6-p-tolyl-indol-1-yl)-acetamide
137. N-(1-Benzyl-2-pyrrolidin-1-yl-ethyl)-2-(6-p-tolyl-indol-1-yl)-acetamide
138. N-[2-(Methyl-phenyl-amino)-ethyl]-2-(6-p-tolyl-indol-1-yl)-acetamide
139. N-[2-(Cyclohexyl-methyl-amino)-ethyl]-2-(6-p-tolyl-benzoimidazol-1-yl)-acetamide
140. N-(2-Pyrrolidin-1-yl-propyl)-2-(6-p-tolyl-indol-1-yl)-acetamide
141. N-[2-(Cyclohexyl-methyl-amino)-ethyl]-2-(4-methoxy-6-p-tolyl-indol-1-yl)-acetamide
142. N-[2-(3,3-Dimethyl-piperidin-1-yl)-ethyl]-2-(6-p-tolyl-indol-1-yl)-acetamide
143. N-[2-(3-Phenyl-piperidin-1-yl)-ethyl]-2-(6-p-tolyl-indol-1-yl)-acetamide
144. N-[2-(3,5-Dimethyl-piperidin-1-yl)-ethyl]-2-(6-p-tolyl-indol-1-yl)-acetamide
145. N-[2-(Cyclohexyl-methyl-amino)-ethyl]-2-(4-oxo-5-p-tolyl-4,5-dihydro-imidazo[4,5-c]pyridin-3-yl)-acetamide
146. N-[2-(Cyclohexyl-methyl-amino)-ethyl]-2-(3-phenyl-6-p-tolyl-indazol-1-yl)-acetamide
147. N-[2-(Cyclohexyl-methyl-amino)-ethyl]-2-(3-pyridin-4-yl-6-p-tolyl-indazol-1-yl)-acetamide
148. N-[2-(Cyclohexyl-methyl-amino)-ethyl]-2-(3-pyrimidin-5-yl-6-p-tolyl-indazol-1-yl)-acetamide
149. N-[2-(Cyclohexyl-methyl-amino)-ethyl]-2-[6-(2-methyl-pyridin-4-yl)indol-1-yl]-acetamide
150. 2-(3-Chloro-indazol-1-yl)-N-[2-(cyclohexyl-methyl-amino)-ethyl]-acetamide; compound with methane
151. N-[2-(Cyclohexyl-methyl-amino)-ethyl]-2-(6-phenyl-indol-1-yl)-acetamide
152. N-[2-(Cyclohexyl-methyl-amino)-ethyl]-2-[6-(4-fluoro-phenyl)indol-1-yl]-acetamide
153. N-[2-(Cyclohexyl-methyl-amino)-ethyl]-2-(6-p-tolyl-indol-1-yl)-acetamide
154. N-[2-(Cyclohexyl-methyl-amino)-ethyl]-2-[6-(4-trifluoromethyl-phenyl)-indol-1-yl]-acetamide
155. N-[2-(Cyclohexyl-methyl-amino)-ethyl]-2-[6-(4-methoxy-phenyl)-indol-1-yl]-acetamide
156. N-[2-(Cyclohexyl-methyl-amino)-ethyl]-2-[6-(3,4-dichloro-phenyl)-indol-1-yl]-acetamide
157. 2-[6-(3-Cyano-phenyl)-indol-1-yl]-N-[2-(cyclohexyl-methyl-amino)-ethyl]-acetamide
158. 2-[6-(4-Chloro-phenyl)-indol-1-yl]-N-[2-(cyclohexyl-methyl-amino)-ethyl]-acetamide
159. N-[2-(Cyclohexyl-methyl-amino)-ethyl]-2-(6-o-tolyl-indol-1-yl)-acetamide
160. 2-[6-(4-Butyl-phenyl)-indol-1-yl]-N-[2-(cyclohexyl-methyl-amino)-ethyl]-acetamide
161. N-[2-(Cyclohexyl-methyl-amino)-ethyl]-2-[6-(3,5-dimethyl-phenyl)-indol-1-yl]-acetamide
162. N-[2-(Cyclohexyl-methyl-amino)-ethyl]-2-[6-(4-fluoro-3-methyl-phenyl)-indol-1-yl]-acetamide
163. N-[2-(Cyclohexyl-methyl-amino)-ethyl]-2-[6-(4-isopropoxy-phenyl)-indol-1-yl]-acetamide
164. N-[2-(Cyclohexyl-methyl-amino)-ethyl]-2-(1-methyl-1H-[5,6']biindolyl-1'-yl)-acetamide
165. N-[2-(Cyclohexyl-methyl-amino)-ethyl]-2-(6-quinolin-3-yl-indol-1-yl)-acetamide
166. 2-(6-Benzofuran-2-yl-indol-1-yl)-N-[2-(cyclohexyl-methyl-amino)-ethyl]-acetamide
167. N-[2-(Cyclohexyl-methyl-amino)-ethyl]-2-[6-(4-ethyl-phenyl)-indol-1-yl]-acetamide
168. N-[2-(Cyclohexyl-methyl-amino)-ethyl]-2-(6-m-tolyl-indol-1-yl)-acetamide
169. N-[2-(Cyclohexyl-methyl-amino)-ethyl]-2-(6-pyridin-4-yl-indol-1-yl)-acetamide
170. N-[2-(Cyclohexyl-methyl-amino)-ethyl]-2-(5-p-tolyl-indol-1-yl)-acetamide
171. N-[2-(Cyclohexyl-methyl-amino)-ethyl]-2-[5-(4-fluoro-phenyl)-indol-1-yl]-acetamide
172. N-[2-(Cyclohexyl-methyl-amino)-ethyl]-2-(4-p-tolyl-indol-1-yl)-acetamide
173. N-[2-(Octahydro-quinolin-1-yl)-ethyl]-2-(6-p-tolyl-indol-1-yl)-acetamide
174. N-[2-(Cyclohexyl-methyl-amino)-ethyl]-2-[6-(4-vinyl-phenyl)-indol-1-yl]-acetamide
175. N-[2-(Cyclohexyl-methyl-amino)-ethyl]-2-[6-(3,4-dimethyl-phenyl)-indol-1-yl]-acetamide
176. N-[2-(Cyclohexyl-methyl-amino)-ethyl]-2-[6-(2-fluoro-4-methyl-phenyl)-indol-1-yl]-acetamide TABLE 1-continued 177. N-[2-(Cyclohexyl-methyl-amino)-ethyl]-2-[6-(3-fluoro-4-methyl-phenyl)-indol-1-yl]-acetamide
178. N-[2-(Cyclohexyl-methyl-amino)-ethyl]-2-(6-p-tolyl-indazol-1-yl)-acetamide
179. 4-(1-{[2-(Cyclohexyl-methyl-amino)-ethylcarbamoyl]-methyl}-1H-indol-6-yl)-benzamide
180. N-[2-(Cyclopentyl-methyl-amino)-ethyl]-2-(6-p-tolyl-indol-1-yl)-acetamide
181. N-(2-Pyrrolidin-1-yl-ethyl)-2-(6-p-tolyl-indol-1-yl)-acetamide
182. N-[2-(2-Methyl-piperidin-1-yl)-ethyl]-2-(6-p-tolyl-indol-1-yl)-acetamide
183. N-(2-Azepan-1-yl-ethyl)-2-(6-p-tolyl-indol-1-yl)-acetamide
184. N-[2-(Cyclohexyl-ethyl-amino)-ethyl]-2-(6-p-tolyl-indol-1-yl)-acetamide
185. N-[2-(4-Methyl-piperidin-1-yl)-ethyl]-2-(6-p-tolyl-indol-1-yl)-acetamide
186. 2-[6-(4-Cyano-phenyl)-indol-1-yl]-N-[2-(cyclohexyl-methyl-amino)-ethyl]-acetamide
187. 1-{[2-(Cyclohexyl-methyl-amino)-ethylcarbamoyl]-methyl}-6-p-tolyl-1H-indole-2-carboxylic acid methyl ester
188. N-(1-Methyl-2-pyrrolidin-1-yl-ethyl)-2-(6-p-tolyl-indol-1-yl)-acetamide
189. N-[2-(Cyclohexyl-methyl-amino)-ethyl]-2-(6-p-tolyl-benzoimidazol-1-yl)-acetamide
190. N-(2-Pyrrolidin-1-yl-propyl)-2-(6-p-tolyl-indol-1-yl)-acetamide
191. N-[2-(Cyclohexyl-methyl-amino)-ethyl]-2-[6-(4-dimethylamino-phenyl)-indol-1-yl]-acetamide
192. N-[2-(3,3-Dimethyl-piperidin-1-yl)-ethyl]-2-(6-p-tolyl-indol-1-yl)-acetamide
193. N-[2-(3,5-Dimethyl-piperidin-1-yl)-ethyl]-2-(6-p-tolyl-indol-1-yl)-acetamide
194. N-[2-(Cyclohexyl-methyl-amino)-ethyl]-2-(4-oxo-5-p-tolyl-4,5-dihydro-imidazo[4,5-c]pyridin-3-yl)-acetamide Compounds of the invention can be prepared as shown in the synthetic procedures outlined in the Examples section of this document.

B. Compositions

In addition to the compounds provided above, compositions for modulating CXCR4 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

Additionally, the pharmaceutical compositions may be adapted for localized administration to the eye in the form of solutions, suspensions, ointments, creams or as a solid or semi-solid insert. Ophthalmic formulations of this compound may contain from 0.0001 to 10% of medicament. Higher dosages as, for example, up to about 20% or lower dosages can be employed provided the dose is therapeutically effective. For ophthalmic administration, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

In one embodiment, pharmaceutical compositions comprising compounds, pharmaceutically acceptable salts, hydrates or N-oxides thereof having formula I, as set forth in Table 1 (vide supra) are of particular interest for the present invention.

C. Methods of Use

The compounds and compositions of the invention can be used to modulate, preferably inhibit, the binding of SDF-1 to the CXCR4 receptor or the binding or SDF-1 or I-TAC to CCXCKR2. Therefore, the compounds and compositions of the invention can be used in the treatment or prevention of diseases or disorders in a mammal in which the inhibition of binding of SDF-1 to the CXCR4 receptor or binding of SDF-1 or I-TAC to CCXCKR2 would provide a therapeutic effect. Diseases and disorders that can be treated by the compounds or compositions of the present invention include cancer, inflammation, HIV infectivity, progenitor/stem cell disorders, among others. Moreover, radioisotopic variants of compounds of Formula I are also useful as radiopharmaceuticals.

Method of Treating Cancer

In one aspect of the invention, the compounds of the invention can be use to prevent the development or spread of cancer cells in a mammal, such as a human. Without wishing to be bound by theory, a compound of the invention that inhibits the binding of SDF-1 to the CXCR4 receptor can provide effective treatment of cancers that over express CXCR4 by decreasing the rate of proliferation (e.g., cellular division) of cancer cells, by causing cessation of proliferation of cancer cells (e.g., entry into G0 phase or senescence), or by causing death of cancer cells, e.g., by initiating apoptosis or through necrotic cell death. Thus, in preferred embodiments a compound of the invention that inhibits the binding of SDF-1 to the CXCR4 receptor can provide therapeutic treatment of cancers that over express the CXCR4 receptor by causing the death of the cancer cells. The CXCR4 inhibitor can cause cell death through initiation of an apoptotic program or through necrotic cell death. Accordingly, in one aspect, the present invention is directed to methods that are useful in the prevention and/or treatment of various cancers, particularly solid tumor cancers, more particularly breast cancer and glioblastoma. In one embodiment, the compounds of the invention are useful for treating breast cancer.

In one aspect, as determined by radiolabeled SDF-1 binding and I-TAC displacement, CCXCKR2 was preferentially expressed in human transformed cells. Included in Table 1B are those tissue types in which CCXCKR2 was expressed (CCXCKR2$^+$) as well as those tissue types in which CCX-CKR2 was not expressed (CCXCKR2$^-$).

TABLE 1B

| CCXCKR2$^+$ | CCXCKR2$^-$ |
|---|---|
| Human Cervical Adenocarcinoma | Normal Mouse Adult Progenitors (c-kit+ & CD34+ BM derived) |
| Human Adenocarcinoma, Mammary Gland | Human Acute Lymphoblastic Leukemia, T Cell |
| Human Burkitt's Lymphoma, B Lymphocyte | Normal Murine Bone Marrow |
| Human Glioblastoma Multiforme, Brain | Normal Murine Thymus |
| Human Carcinoma, Prostate | Normal Murine Lung |
| Murine Lymphoblastic Leukemia, B Lymphocyte | Normal Murine Spleen |
| Murine Mammary Gland Tumor | Normal Murine Liver |
| Normal Murine Fetal Liver | Normal Murine PBL |
| Normal Mouse Brain | Normal Human PBL |
| Normal Mouse Kidney | Normal Murine Heart |
| | Normal Murine Pancreas |

A preferred method of treating cancer, includes administering a therapeutically effective amount of one or more of the previously mentioned compounds (or salts thereof) to a cancer patient for a time sufficient to treat the cancer.

For treatment, the compositions of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In addition to humans, a variety of other mammals can be treated according to the method of the present invention. For instance, mammals consisting of other primates, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Standard in vivo assays demonstrating that the compositions of the present invention are useful for treating cancer include those described in Bertolini, F., et al., *Endostatin, an antiangiogenic drug, induces tumor stabilization after chemotherapy or anti-CD20 therapy in a NOD/SCID mouse model of human high-grade non-Hodgkin lymphoma*. Blood, No. 1, Vol. 96, pp. 282-87 (1 Jul. 2000); Pengnian, L., *Antiangiogenic gene therapy targeting the endothelium-specific receptor tyrosine kinase Tie2*. Proc. Natl. Acad. Sci. USA, Vol. 95, pp. 8829-34 (July 1998); and Pulaski, B. *Cooperativity of Staphylococcal aureus Enterotoxin B Superantigen, Major Histocompatibility Complex Class II, and CD80 for Immunotherapy of Advanced Spontaneous Metastases in a Clinically Relevant Postoperative Mouse Breast Cancer Model*. Cancer Research, Vol. 60, pp. 2710-15 (May 15, 2000).

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

The compounds and compositions of the present invention can be combined with other compounds and compositions having related utilities to prevent and treat cancer and diseases or conditions associated with CXCR4 signaling. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: cisplatin, paclitaxel, methotrexate, cyclophosphamide, ifosfamide, chlorambucil, carmustine, carboplatin, vincristine, vinblastine, thiotepa, lomustine, semustine, 5-fluorouracil and cytarabine. The weight ratio of the compound of the present invention to the second active ingredient may be varied and will depend upon the effective dose of each ingredient. Generally, an effective dose of each will be used. Thus, for example, when a compound of the present invention is combined with a second anticancer agent, the weight ratio of the compound of the present invention to the second agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Radio-Imaging

In addition to the growing efforts for targeting and inhibiting chemokine receptors (i.e., CXCR4 or CXCR7) in cancerous cells, the role that chemokine receptors overexpression plays in cancer development is gradually being unraveled. Consequently, there is interest in the use of chemokine receptor inhibitors as radiotracers for the molecular imaging of chemokine receptor overexpressing tumors via nuclear medicine modality, such as, for example, in Positron Emission Tomography (PET).

In another aspect, the present invention provides radioisotopes of compounds of formula I for use in radio-imaging and radiotherapy purposes. The use of radioactive nuclides for medicinal purposes is well known in the art. Biologically active compounds that bind to specific cell surface receptors or that otherwise modify cellular functions have received some consideration as radiopharmaceuticals, and therefore, when labeled with a radioactive nuclide, such compounds are used as biospecific agents in radioimaging and radiotherapy.

Positron Emission Tomography (PET), a nuclear medicine imagine technology which allows the three-dimensional, quantitative determination of the distribution of radioactivity within the human body, is becoming an increasingly important tool for the measurement of physiological, biochemical, and pharmacological function at a molecular level, both in healthy and pathological states. PET requires the administration to a subject of a molecule labeled with a positron-emitting nuclide (radiotracer) such as $^{15}O$, $^{13}N$, $^{11}C$, and $^{18}F$, which have half-lives of 2, 10, 20, and 110 minutes, respectively.

Single Photon Emission Computed Tomography (SPECT) is a form of chemical imaging in which emissions from radioactive compounds, labeled with gamma-emitting radionuclides, are used to create cross-sectional images of radioactivity distribution in vivo. SPECT requires the administration to a subject of a molecule labeled with a gamma-emitting nuclide such as $^{99m}Tc$, $^{67}Ga$, $^{111}In$ and $^{123}I$.

The use of nuclear medicine imaging techniques such as Single Photon Emission Compute Tomography (SPECT) and Positron Emission Tomography (PET), along with a suitable radiotracer that binds selectively (or non-selectively) to at least one chemokine receptor that is overexpressed in cancer cells, (i.e., CXCR4 or CCXCKR2 (CXCR7)), can provide for in vivo drug development and identification of a lead chemical structure to be used as a chemokine receptor biospecific agent for radiotherapy or as a labeled bioprobe for diagnosis by radioimaging. Nuclear imaging can be further used for in vivo mapping and quantification of the one or more chemokine receptors in cancer. Using a labeled CXCR4 or CXCR7 inhibitor would enable both the identification of patients having tumors overexpressing the CXCR4 or CXCR7 receptors and the study of changes in the levels of receptor expression during therapy. Such a diagnostic method can lead to a better patient management and differentiation in regards to therapeutic course of action.

Methods of Treating Inflammation

Still further, the compounds and compositions of the present invention are useful for the treatment of inflammation, and can be combined with other compounds and compositions having therapeutic utilities that may require treatment either before, after or simultaneously with the treatment of inflammation with the present compounds. Accordingly, combination methods and compositions are also a component of the present invention to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

As noted, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, CXCR7, CX$_3$CR1 and CXCR6; (m) lubricants or emollients such as petrolatum and lanolin, (n) keratolytic agents (e.g., tazarotene), (o) vitamin D$_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β1β, (Betaseron®), interferon (β-1α ((Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Method of Treating HIV Infectivity

Still further, the compounds and compositions of the present invention are useful for the (prophylactic, curative or palliative) treatment of HIV infectivity, and can be combined with other compounds and compositions having therapeutic utilities that may require treatment either before, after or simultaneously with the treatment of HIV infectivity with the present compounds.

In certain aspects, in the treatment of HIV infectivity, an appropriate dosage level will generally be about 0.001 to 100 mg per kg patient body weight per day which can be administered in single or multiple doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Included within the scope of the invention are embodiments comprising the co-administration of a compound of the invention with one or more additional therapeutic agents, and compositions containing a compound of the invention along with one or more additional therapeutic agents. Such a combination therapy is especially useful for the prevention and/or treatment of infection by HIV and related retroviruses which may evolve rapidly into strains resistant to any monotherapy. Alternatively, additional therapeutic agents may be desirable to treat diseases and conditions which result from or accompany the disease being treated with the compound of the invention. For example, in the treatment of an HIV or related retroviral infection, it may be desirable to additionally treat opportunistic infections, neoplasms and other conditions which occur as a result of the immuno-compromised state of the patient being treated.

Preferred combinations of the invention include simultaneous or sequential treatment with a compound of the invention and one or more: (a) reverse transcriptase inhibitors such as abacavir, adefovir, didanosine, lamivudine, stavudine, zalcitabine and zidovudine; (b) non-nucleoside reverse transcriptase inhibitors such as capavirine, delavirdine, efavirenz, and nevirapine; (c) HIV protease inhibitors such as indinivir, nelfinavir, ritonavir, and saquinavir; (d) CCR5 antagonists such as TAK-779 or UK-427,857; (e) CXCR4 antagonists such as AMD-3100; (f) integrase inhibitors, such as L-870, 810 or S-1360; (g) inhibitors of viral fusion such as T-20; (h) investigational drugs such as trizivir, KNI-272, amprenavir, GW-33908, FTC, PMPA, MKC-442, MSC-204, MSH-372, DMP450, PNU-140690, ABT-378, KNI-764, DPC-083, TMC-120 or TMC-125; (i) antifungal agents, such as fluconazole, itraconazole or voriconazole; or (j) antibacterial agents, such as azithromycin.

Method of Use in Progenitor/Stem Cell Related Treatments

Still further, the compounds and compositions of the present invention can be useful for the mobilization of progenitor/stem cells following the procedures and protocols described in WO05/000333 incorporated herein by reference in its entirety for all purposes. Typical conditions which may be ameliorated or otherwise benefited include hematopoietic disorders, such as aplastic anemia, leukemias, drug-induced anemias, and hematopoietic deficits from chemotherapy or radiation therapy. Still further, the compounds and compositions of the invention can be used in enhancing the success of transplantation during and following immunosuppressive treatments as well as in effecting more efficient wound healing and treatment of bacterial infections.

The compounds and compositions of the present invention can be useful in preventing progenitor/stem proliferation following the procedures and protocols as described in, US2003/0148940, incorporated herein by reference in its entirety for all purposes. For example, agents that prevent stem cell proliferation may be useful in therapies that use cytotoxic agents (e.g., chemotherapeutic, or radiation therapy) that can kill proliferating cells such as cancer cells and hematopoietic cells. Preventing the progenitor/stem cell proliferation during the use of therapies requiring cytotoxic agents can enhance recovery of mature blood cell counts, such as leukocytes, lymphocytes and red blood cells following cytotoxin treatment.

In the treatment of progenitor or stem cell mobilization disorders an appropriate dosage level will generally be about 0.001 to 100 mg per kg patient body weight per day which can be administered in single or multiple doses. The compounds may be administered as a single dose, a dose over time, as in i.v., or transdermal administration, or in multiple doses. The compounds of the invention can also be be used in ex vivo treatment protocols to prepare cell cultures which are then used to replenish the blood cells of the subject. Ex vivo treatment can be conducted on autologous cells harvested from the peripheral blood or bone marrow or from allografts from matched donors.

The present compounds can be combined with other compounds and compositions having therapeutic utilities that may require treatment either before, after or simultaneously with the treatment of the progenitor/stem cell disorder with the present compounds. For example, the compounds of the invention can be used in combination with other agent that increase white blood cells and progenitor cells in human and animal subjects. These agents include granulocyte-macrophage colony stimulating factor (GM-CSF), Interleukin-1 (IL-1), Interleukin-2 (IL-3), Interleukin-8 (IL-8), PIXy-321 (GM-CSF/IL-3 fusin protein), macrophage inflammatory protein, stem cell factor, thrombopoietin and growth related oncogene or chemotherapy and the like. (For a discussion of other agents that can increase progenitor cells, see Dale, D., et al. Am J. of Hematol. (1998) 57, 7-15; Rosenfeld, C. et al. Bone Marrow Transplantation (1997) 17, 179-183; Pruijt, J., et al. Cur. Op. in Hematol. (1999) 6, 152-158; Broxmeyer, H., et al. Exp. Hematol. (1995) 23, 335-340; Broxmeyer, et al., Blood, Cells, Molecules and Diseases (1998) 24, 14-30; Glaspy, J., et al., Cancer Chemother. Pharmacol. (1996) 38 suppl, S53-S57; Vadhan-Raj, S., et al. Ann. Intern. Med (1997) 126, 673-681; King, A., et al., Blood (2001) 97, 1534-1542; Glaspy, J., et al., Blood (1997) 90, 2939-2951) Accordingly, combination methods and compositions are also a component of the present invention to prevent and treat the condition or disease of interest.

Method of Use in Treating Ocular Disorders

In addition, the compounds and compositions disclosed in the present invention are useful for treating and/or preventing a variety of angiogenic, microvascular and macular disorders including primary indications for diabetic retinopathy, macular degeneration (such as wet or neovascular age-related macular degeneration (AMD) and dry or atrophic AMD), macular edema, and secondary indications for inhibiting tumor vascularization, and corneal and iris neovascularization.

Neovascular diseases of the eye, such as neovascular AMD and diabetic retinopathy, occur when the normally quiescent vessels in the retina or choroid are stimulated to proliferate within or beneath the retina. These newly formed vessels may also cause hemorrhages at the sites of neovascularization. Together, the vessel overgrowth and hemorrhaging lead to disruption of the retinal structure and vision loss.

The compounds and compositions of the present invention inhibit angiogenesis in an established animal model of ocular neovascularization. This model has been described previously by Kyoichi Takahashi et al., *Investigative Opthalmology and Visual Science,* 2003, 44: 406, and is incorporated herein by reference.

Macular edema is a swelling of the retina that occurs within the critically important central visual zone at the posterior pole of the eye (the macula). The capillaries within the retina are composed of endothelial cells and pericytes interconnected by tight junctions. These endothelial cell:pericyte connections contribute to the blood-retinal barrier. Newly formed vessels that contain endothelial cells but that have not yet acquired a pericyte coating are more permeable and can allow the leakage of fluid and proteins which can lead to macular edema. The anti-angiogenic activities of CXCR4 inhibitors will inhibit formation of these immature, leaky vessels and potentially reduce the risk of macular edema.

The compounds produced in the present invention are readily combined with suitable and known pharmaceutically acceptable excipients to produce compositions which may be administered to mammals, including humans, to treat or prevent macular disorders. The compounds may also be combined with other angiogenesis inhibitors including, but not limited to, KDR kinase inhibitors (U.S. Pat. No. 6,306,874, incorporated herein by reference in its entirety) or angiogenic steroids such as dexamethasone, anecortave acetate, fluocinolone and triamcinolone.

Use of the compounds of formula I for the manufacture of a medicament for treating, macular edema, macular degeneration, diabetic retinopathy, corneal and iris neovascularization or for a combination thereof is also included in this invention.

III. EXAMPLES

The following examples are offered to illustrate, but not to limit the claimed invention.

Reagents and solvents used below can be obtained from commercial sources such as Aldrich Chemical Co. (Milwaukee, Wis., USA). I H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system. Method A: Agilent Zorbax SB-C18, 2.1×50 mm, 5μ, 35° C., 1 ml/min flow rate, a 2.5 min gradient of 0% to 100% B with a 1.0 min wash at 100% B; A=0.1% formic acid/5% acetonitrile/94.9% water, B=0.08% formic acid/5% water/94.9% acetonitrile. Method B: Agilent Zorbax SB-C18, 2.1×50 mm, 5μ, 35° C., 1 ml/min flow rate, a 2.5 min gradient of 20% to 100% B with a 1.0 min wash at 100% B; A=0.1% formic acid/5% acetonitrile/94.9% water, B=0.08% formic acid/5% water/94.9% acetonitrile.

The following abbreviations are used in the Examples and throughout the description of the invention:

rt: room temperature
HPLC: high pressure liquic chromatography
TLC: Thin Layer Chromatography
EtOH: Ethanol
MeOH: Methanol
SiO2: Silicon dioxide gel
EtOAc: Ethyl Acetate
AcOH: Acetic Acid
HATU: 2-(7-Aza-1H-benzotriazole-1-yl)-1,1,3,3-tetramethyluronium hexafluorophosphate
DMF: Dimethylformamide
THF: Tetrahydrofuran
DMAP: Dimethylaminopyridine
TEA: Triethylamine
TMSCHN$_2$: (Trimethylsilyl)diazomethane [Cas No. 18107-18-1]

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Preparation of N-[2-(Cyclohexyl-methyl-amino)-ethyl]-2-indol-1-yl-acetamide (3a)

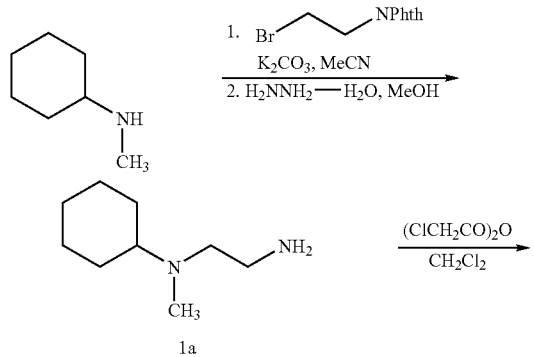

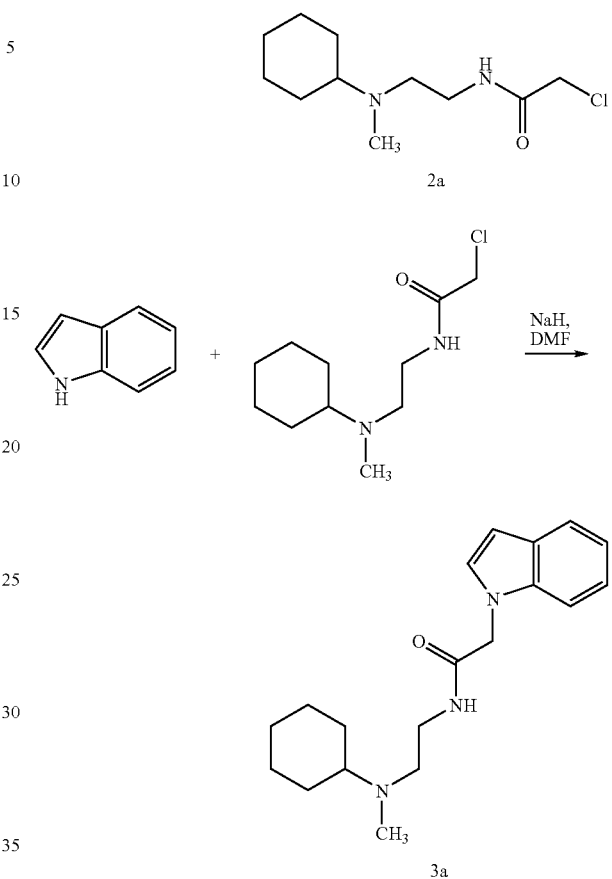

Preparation of N$^1$-Cyclohexyl-N$^1$-methyl-ethane-1,2-diamine (1a): To a solution of N-methylcyclohexylamine (10 g, 0.88 mol) in 100 mL of MeCN, was added K$_2$CO$_3$ (24 g, 0.17 mol) and (N-2-bromo-ethyl)-phthalimide (33 g, 0.13 mol). The reaction mixture was heated at reflux (90° C.) under nitrogen atmosphere for 2 days. The reaction mixture was cooled to room temperature and filtered through a pad of celite and concentrated in vacuo. The resultant residue was dissolved in a minimum amount of dichloromethane and further diluted with hexanes; the resultant solution was allowed to stand overnight. Excess (N-2-bromo-ethyl)-phthalimide precipitated out of solution and was removed by filtration. The filtrate was then concentrated and purified by column chromatography (SiO$_2$, EtOAc/hexanes 0.5:9.5) to obtain the alkylated product (18 g, 72%, 0.06 mol). The product was dissolved in MeOH (250 mL) and to it was added H$_2$NNH$_2$—H$_2$O (6.2 g, 0.12 mol) and the reaction mixture was stirred overnight at 65° C. The reaction mixture was then filtered over a pad of celite and the filtrate concentrated to provide the crude product which was purified by column chromatography (SiO$_2$, 8% MeOH in CHCl$_3$) to obtain 6 g, 61% yield of amine 1a.

Preparation of 2-Chloro-N-[2-(cyclohexyl-methyl-amino)-ethyl]-acetamide (2a): To a solution of amine 1a (250 mg, 1.6 mmol) in CH$_2$Cl$_2$ (1 mL) at 0° C. was added dropwise chloroacetic anhydride (287 mg, 1.7 mmol) in CH$_2$Cl$_2$ (1 mL). The reaction was warmed to room temperature and was then stirred for 30 minutes. The reaction was then concentrated to 1 mL and then diluted with Et$_2$O (4 mL). Saturated NaHCO$_3$ (aq) was then added and the organic was removed. The aqueous layer was extracted with Et$_2$O (4×). The organic layers were combined, dried over Na$_2$SO$_4$, and concentrated. The resulting chloride 2a was used immediately in the next reaction without purification.

Preparation of N-[2-(Cyclohexyl-methyl-amino)-ethyl]-2-indol-1-yl-acetamide (3a): Indole (20 mg, 0.17 mmol) was dissolved in DMF (400 μL) and NaH (60% dispersed in mineral oil, 9 mg, 0.22 mmol) was added and the resultant mixture was stirred at 60° C. for 30 minutes. The mixture was then cooled to room temperature to it was added crude chloride 2a (~50 mg; excess). The reaction solution was then heated to 60° C. for 2 hours. The reaction solution was cooled to room temperature and diluted in EtOAc and the organic solution was washed with H$_2$O (2×) and brine (1×). The organic layer was dried (MgSO$_4$) and concentrated to provide crude 3a which was purified by preparative TLC (2:1:0.4 EtOAc/hexanes/Et$_3$N) to give the desired product 3a (7 mg, 13% yield): LC-MS (Method B, retention time=0.448 min. MS calc'd for C$_{19}$H$_{28}$N$_3$O (MH$^+$): 314.2. Found 314.5.

Example 2

Preparation of N$^1$-Cyclohexyl-N$^1$-methyl-propane-1,3-diamine (1b)

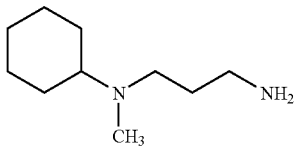

1b

Compound 1b was prepared similarly as following the general synthetic procedure outlined in step 1 of Example 1.

Example 3

Preparation of 2-(Octahydro-quinolin-1-yl)-ethylamine (1c)

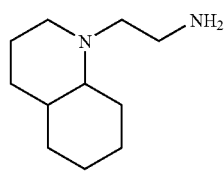

1c

Compound 1c was prepared similarly as following the general synthetic procedure outlined in step 1 of Example 1.

Example 4

The following compounds were synthesized the following the synthetic procedures outlined in Example 1.

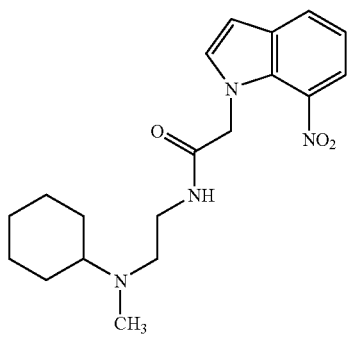

3b

N-[2-(Cyclohexyl-methyl-amino)-ethyl]-2-(7-nitro-indol-1-yl)-acetamide (3b): LC-MS (Method B, retention time=1.695 min. MS calc'd for C$_{19}$H$_{27}$N$_4$O$_3$ (MH$^+$): 359.2. Found 359.2.

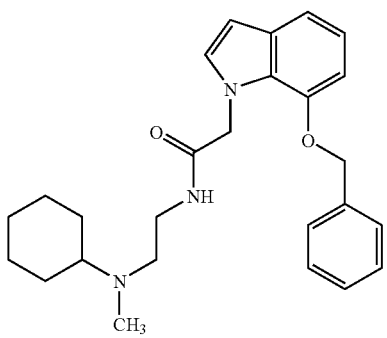

3c 2-(7-Benzyloxy-indol-1-yl)-N-[2-(cyclohexyl-methyl-amino)-ethyl]-acetamide (3c): LC-MS (Method B, retention time=2.082 min. MS calc'd for C$_{26}$H$_{34}$N$_3$O$_2$ (MH$^+$): 420.3. Found 420.2.

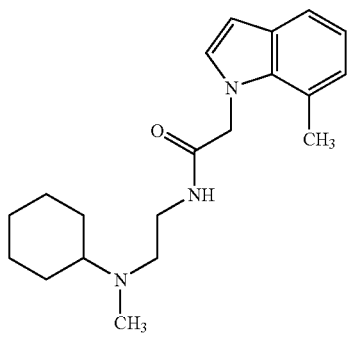

3d

N-[2-(Cyclohexyl-methyl-amino)-ethyl]-2-(7-methyl-indol-1-yl)-acetamide (3d): LC-MS (Method B, retention time=1.708 min. MS calc'd for C$_{20}$H$_{30}$N$_3$O (MH$^+$): 328.2. Found 328.2.

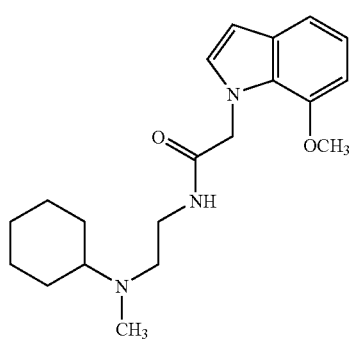

3e

N-[2-(Cyclohexyl-methyl-amino)-ethyl]-2-(7-methoxy-indol-1-yl)-acetamide (3e): LC-MS (Method B, retention time=1.673 min. MS calc'd for $C_{20}H_{30}N_3O_2$ (MH$^+$): 344.2. Found 344.2.

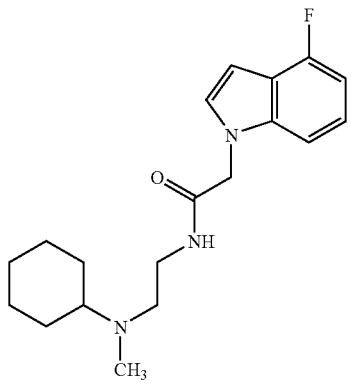

3h

N-[2-(Cyclohexyl-methyl-amino)-ethyl]-2-(4-fluoro-indol-1-yl)-acetamide (3h): LC-MS (Method B, retention time=1.727 min. MS calc'd for $C_{19}H_{27}FN_3O$ (MH$^+$): 332.2. Found 332.2.

3f

N-[2-(Cyclohexyl-methyl-amino)-ethyl]-2-[7-(4-fluorophenyl)-indol-1-yl]-acetamide (3f): LC-MS (Method B, retention time=2.113 min. MS calc'd for $C_{25}H_{31}FN_3O$ (MH$^+$): 408.3. Found 408.2.

3i 2-(7-Bromo-indol-1-yl)-N-[2-(cyclohexyl-methyl-amino)-ethyl]-acetamide (3l): LC-MS (Method B, retention time=1.848 min. MS calc'd for $C_{19}H_{27}BrN_3O$ (MH$^+$): 392.1. Found 392.1.

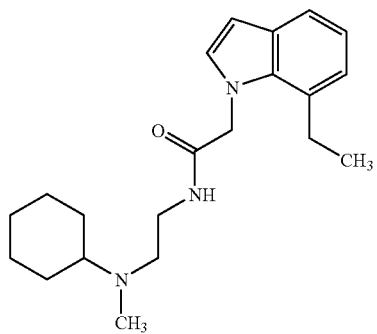

3g

N-[2-(Cyclohexyl-methyl-amino)-ethyl]-2-(7-ethyl-indol-1-yl)-acetamide (3g): LC-MS (Method B, retention time=1.816 min. MS calc'd for $C_{21}H_{32}N_3O$ (MH$^+$): 342.3. Found 342.2.

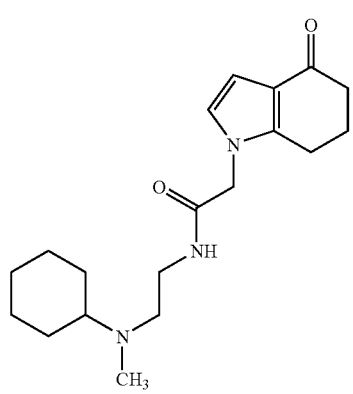

3j

N-[2-(Cyclohexyl-methyl-amino)-ethyl]-2-(4-oxo-4,5,6,7-tetrahydro-indol-1-yl)-acetamide (3j): LC-MS (Method B, retention time=0.285 min. MS calc'd for $C_{19}H_{30}N_3O_2$ (MH$^+$): 332.2. Found 332.2.

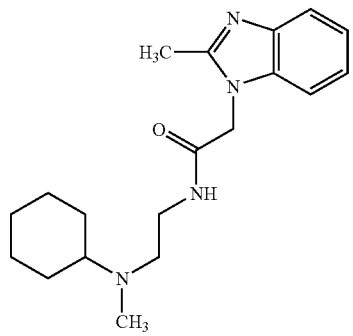

3k

N-[2-(Cyclohexyl-methyl-amino)-ethyl]-2-(2-methyl-benzoimidazol-1-yl)-acetamide (3k): LC-MS (Method B, retention time=0.250 min. MS calc'd for $C_{19}H_{29}N_4O$ (MH$^+$): 329.2. Found 329.6.

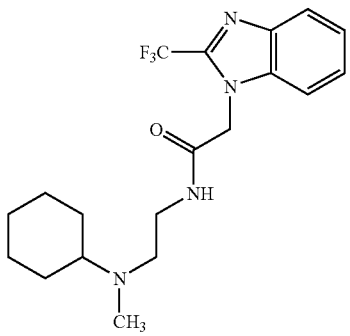

3n

N-[2-(Cyclohexyl-methyl-amino)-ethyl]-2-(2-trifluoromethyl-benzoimidazol-1-yl)-acetamide (3n): LC-MS (Method A, retention time=2.009 min. MS calc'd for $C_{19}H_{26}F_3N_4O$ (MH$^+$): 383.2. Found 383.5.

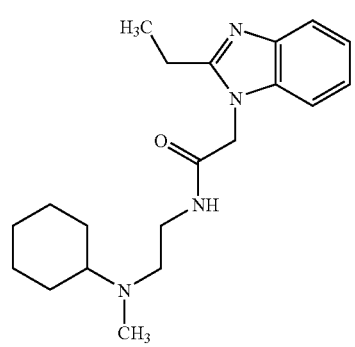

3l

N-[2-(Cyclohexyl-methyl-amino)-ethyl]-2-(2-ethyl-benzoimidazol-1-yl)-acetamide (3l): LC-MS (Method B, retention time=0.265 min. MS calc'd for $C_{20}H_{31}N_4O$ (MH$^+$): 343.3. Found 343.6.

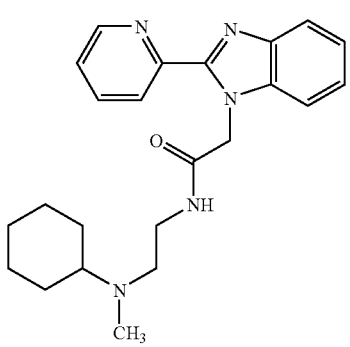

3o

N-[2-(Cyclohexyl-methyl-amino)-ethyl]-2-(2-pyridin-2-yl-benzoimidazol-1-yl)-acetamide (3o): LC-MS (Method A, retention time=1.882 min. MS calc'd for $C_{23}H_{30}N_5O$ (MH$^+$): 392.3. Found 392.6.

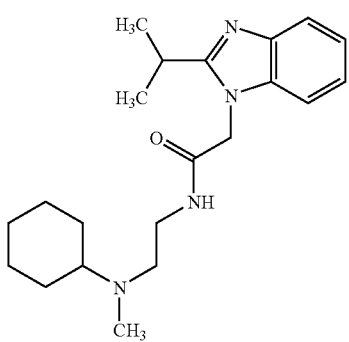

3m

N-[2-(Cyclohexyl-methyl-amino)-ethyl]-2-(2-isopropyl-benzoimidazol-1-yl)-acetamide (3m): LC-MS (Method B, retention time=0.246 min. MS calc'd for $C_{21}H_{33}N_4O$ (MH$^+$): 357.3. Found 357.5.

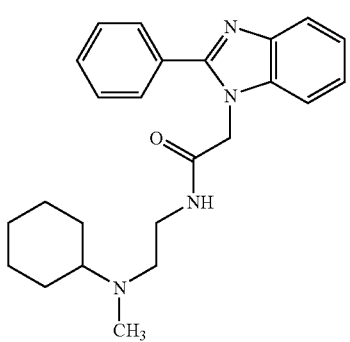

3p

N-[2-(Cyclohexyl-methyl-amino)-ethyl]-2-(2-phenyl-benzoimidazol-1-yl)-acetamide (3p): LC-MS (Method A, retention time=1.729 min. MS calc'd for $C_{24}H_{31}N_4O$ (MH$^+$): 391.3. Found 391.6.

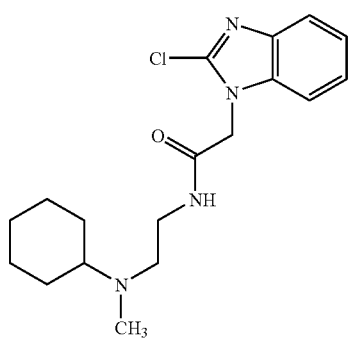

2-(2-Chloro-benzoimidazol-1-yl)-N-[2-(cyclohexyl-methyl-amino)-ethyl]-acetamide (3q): LC-MS (Method B, retention time=0.264 min. MS calc'd for $C_{18}H_{26}ClN_4O$ (MH$^+$): 349.2. Found 349.5.

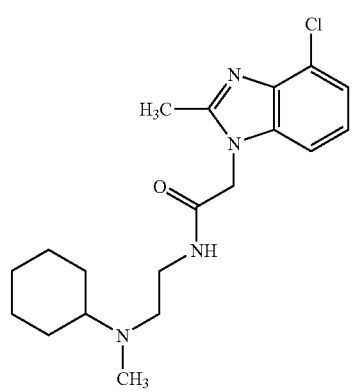

2-(4-Chloro-2-methyl-benzoimidazol-1-yl)-N-[2-(cyclohexyl-methyl-amino)-ethyl]-acetamide (3r): LC-MS (Method A, retention time=1.642 min. MS calc'd for $C_{19}H_{28}ClN_4O$ (MH$^+$): 363.2. Found 363.5.

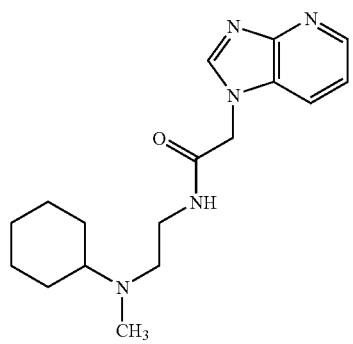

N-[2-(Cyclohexyl-methyl-amino)-ethyl]-2-imidazo[4,5-b]pyridin-1-yl-acetamide (3s): LC-MS (Method A, retention time=0.246 min. MS calc'd for $C_{17}H_{26}N_5O$ (MH$^+$): 316.2. Found 316.5.

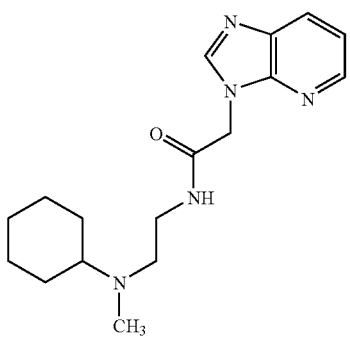

N-[2-(Cyclohexyl-methyl-amino)-ethyl]-2-imidazo[4,5-b]pyridin-3-yl-acetamide (3t): LC-MS (Method A, retention time=0.247 min. MS calc'd for $C_{17}H_{26}N_5O$ (MH$^+$): 316.2. Found 316.5.

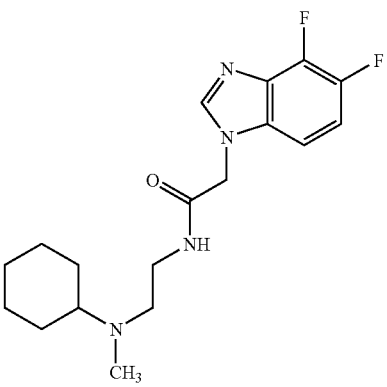

N-[2-(Cyclohexyl-methyl-amino)-ethyl]-2-(4,5-difluoro-benzoimidazol-1-yl)-acetamide (3u$^1$)/N-[2-(Cyclohexyl-methyl-amino)-ethyl]-2-(6,7-difluoro-benzoimidazol-1-yl)-acetamide (3u$^2$) (ratio of 3:1): LC-MS (Method A, retention time=1.800 min. MS calc'd for $C_{18}H_{25}F_2N_4O$ (MH$^+$): 351.2. Found 351.5.

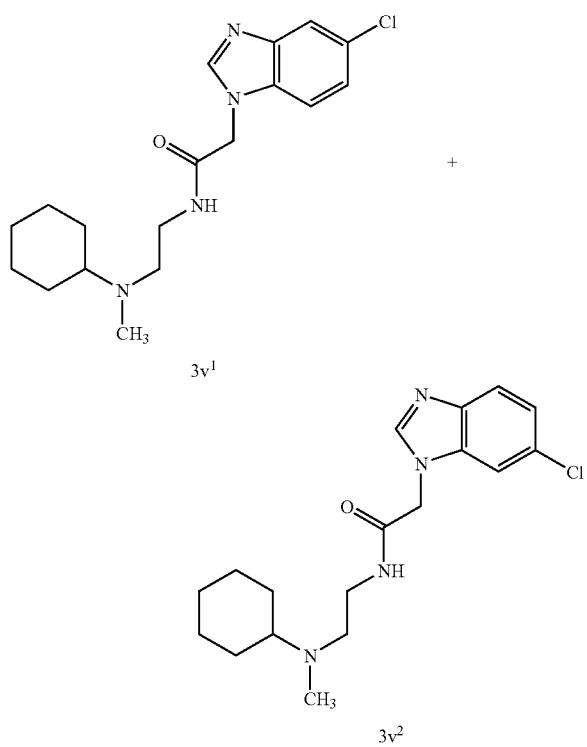

3v¹

3v²

2-(5-Chloro-benzoimidazol-1-yl)-N-[2-(cyclohexyl-methyl-amino)-ethyl]-acetamide (3v¹)/2-(6-Chloro-benzoimidazol-1-yl)-N-[2-(cyclohexyl-methyl-amino)-ethyl]-acetamide (3v²) (ratio 1:1): LC-MS (Method A, retention time=1.782 min. MS calc'd for $C_{18}H_{26}ClN_4O$ (MH⁺): 349.2. Found 349.5.

3w¹

3w²

N-[2-(Cyclohexyl-methyl-amino)-ethyl]-2-(5-methyl-benzoimidazol-1-yl)-acetamide (3w¹)/N-[2-(Cyclohexyl-methyl-amino)-ethyl]-2-(6-methyl-benzoimidazol-1-yl)-acetamide (3w²) (ratio 1:1): LC-MS (Method B, retention time=0.245 min. MS calc'd for $C_{19}H_{29}N_4O$ (MH⁺): 329.2. Found 329.5.

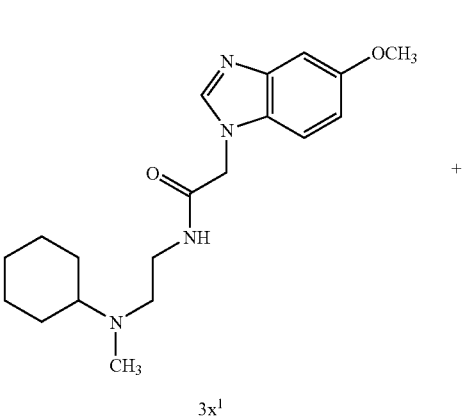

3x¹

3x²

N-[2-(Cyclohexyl-methyl-amino)-ethyl]-2-(5-methoxy-benzoimidazol-1-yl)-acetamide (3x¹)/N-[2-(Cyclohexyl-methyl-amino)-ethyl]-2-(6-methoxy-benzoimidazol-1-yl)-acetamide (3x²) (ratio 1:1): LC-MS (Method A, retention time=1.478 min. MS calc'd for $C_{19}H_{29}N_4O_2$ (MH⁺): 345.2. Found 345.5.

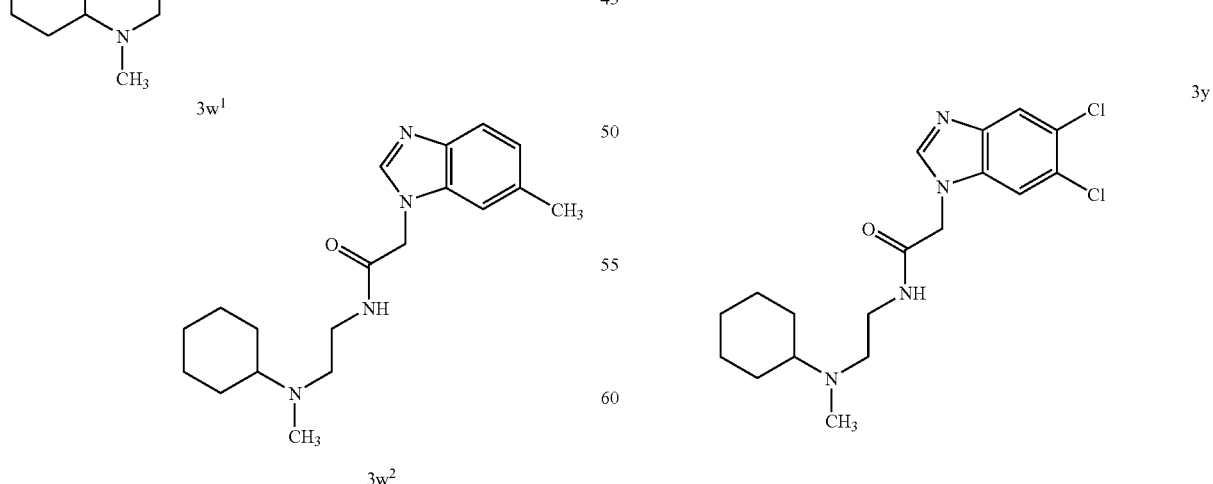

3y

N-[2-(Cyclohexyl-methyl-amino)-ethyl]-2-(5,6-dichloro-benzoimidazol-1-yl)-acetamide (3y): LC-MS (Method B, retention time=1.402 min. MS calc'd for $C_{18}H_{25}Cl_2N_4O$ (MH⁺): 383.1. Found 383.5.

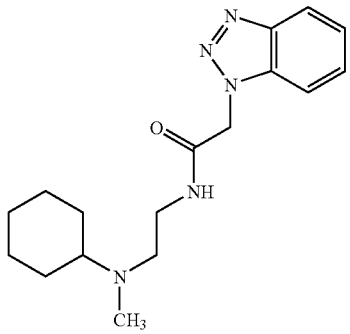

2-Benzotriazol-1-yl-N-[2-(cyclohexyl-methyl-amino)-ethyl]-acetamide (3z): LC-MS (Method B, retention time=0.345 min. MS calc'd for $C_{17}H_{26}N_5O$ (MH+): 316.2. Found 316.5.

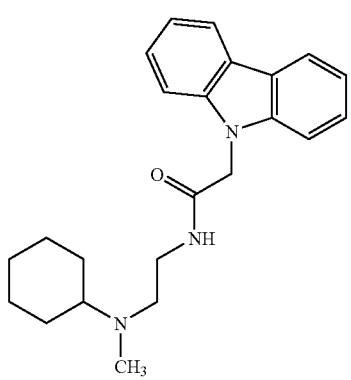

2-Carbazol-9-yl-N-[2-(cyclohexyl-methyl-amino)-ethyl]-acetamide (3aa): LC-MS (Method B, retention time=0.768 min. MS calc'd for $C_{23}H_{30}N_3O$ (MH+): 364.2. Found 364.6.

Example 5

Preparation of N-[2-(Cyclohexyl-methyl-amino)-ethyl]-2-(7-phenyl-indol-1-yl)-acetamide (4a)

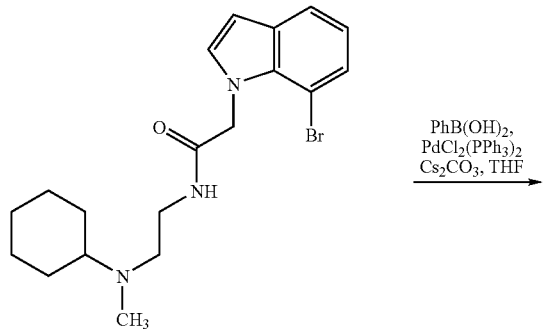

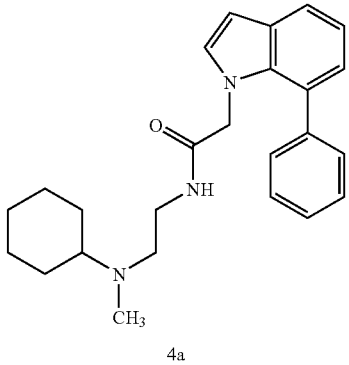

Bromoindole 3i (10 mg, 0.025 mmol) was dissolved in THF (400 μL). $Cs_2CO_3$ (14 mg, 0.043 mmol), phenylboronic acid (5 mg, 0.038 mmol), and a catalytic amount of $PdCl_2(PPh_3)_2$ were added and the reaction was heated in a sealed vessel at 80° C. for 12 h under a nitrogen atmosphere. The solvent was removed under reduced pressure and the resulting mixture was purified by preparative TLC (1:1:0.25 EtOAc/hexanes/Et₃N) to provide indole 4a (4 mg, 41% yield): LC-MS (Method B, retention time=1.922 min. MS calc'd for $C_{25}H_{32}N_3O$ (MH+): 390.3. Found 390.6.

Example 6

Preparation of N-[2-(Cyclohexyl-methyl-amino)-ethyl]-2-[7-(4-methoxy-phenyl)-indol-1-yl]-acetamide (4b)

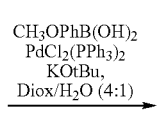

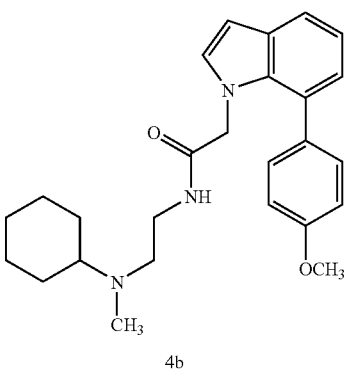

The bromoindole 3i (20 mg, 0.063 mmol) was combined with 4-methoxyphenyl boronic acid (15 mg, 0.082 mmol), $PdCl_2(PPh_3)_2$ (catalytic amount) and dissolved in 1 mL of Dioxanes/$H_2O$ (4:1). 1M KOtBu in THF (100 μL) was then added and the resultant reaction mixture was stirred at 80° C. under a nitrogen atmosphere in a sealed vial for 12 hours. The solvent was then evaporated under reduced pressure and the crude product was purified by preparative TLC (1:1:0.25 EtOAc/hexanes/Et$_3$N) to provide indole 4b (15.8 mg, 60% yield): LC-MS (Method B, retention time=1.823 min. MS calc'd for C$_{26}$H$_{34}$N$_3$O$_2$ (MH$^+$): 420.3. Found 420.6.

Example 7

The following compounds were synthesized the following the synthetic procedures outlined in Examples 5 and 6.

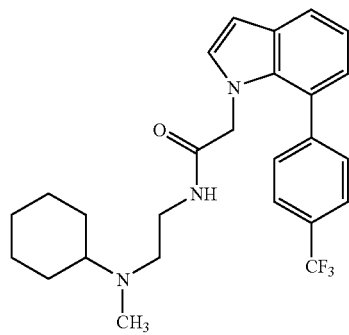

4c

N-[2-(Cyclohexyl-methyl-amino)-ethyl]-2-[7-(4-trifluoromethyl-phenyl)-indol-1-yl]-acetamide (4c): LC-MS (Method B, retention time=2.105 min. MS calc'd for C$_{26}$H$_{31}$F$_3$N$_3$O (MH$^+$): 458.2. Found 458.6.

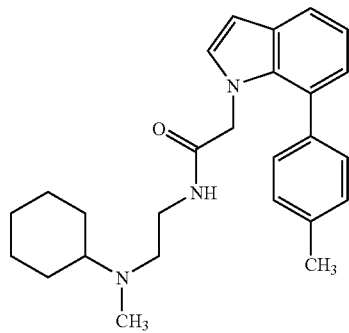

4d

N-[2-(Cyclohexyl-methyl-amino)-ethyl]-2-(7-p-tolyl-indol-1-yl)-acetamide (4d): LC-MS (Method B, retention time=1.973 min. MS calc'd for C$_{26}$H$_{34}$N$_3$O (MH$^+$): 404.3. Found 404.6.

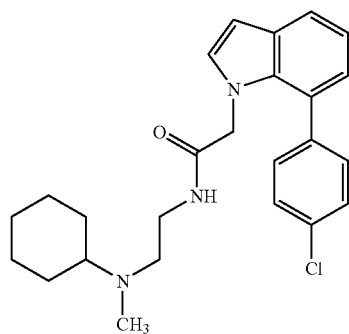

4e

2-[7-(4-Chloro-phenyl)-indol-1-yl]-N-[2-(cyclohexyl-methyl-amino)-ethyl]-acetamide (4e): LC-MS (Method B, retention time=1.959 min. MS calc'd for C$_{25}$H$_{31}$ClN$_3$O (MH$^+$): 424.2. Found 424.6.

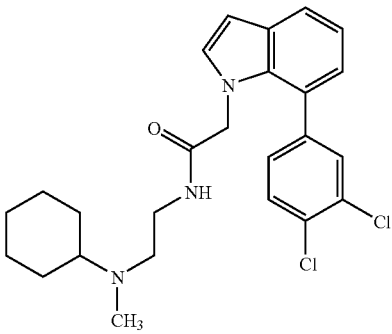

4f

N-[2-(Cyclohexyl-methyl-amino)-ethyl]-2-[7-(3,4-dichloro-phenyl)-indol-1-yl]-acetamide (4f): LC-MS (Method B, retention time=2.258 min. MS calc'd for C$_{25}$H$_{30}$Cl$_2$N$_3$O (MH$^+$): 458.2. Found 458.5.

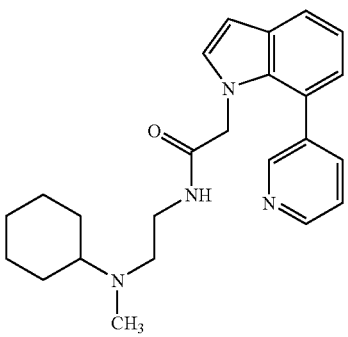

4g

N-[2-(Cyclohexyl-methyl-amino)-ethyl]-2-(7-pyridin-3-yl-indol-1-yl)-acetamide (4g): LC-MS (Method B, retention time=0.454 min. MS calc'd for C$_{24}$H$_{31}$N$_4$O (MH$^+$): 391.3. Found 391.6.

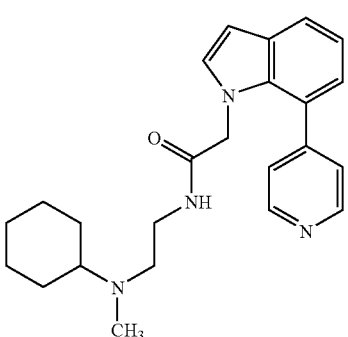

4h

N-[2-(Cyclohexyl-methyl-amino)-ethyl]-2-(7-pyridin-4-yl-indol-1-yl)-acetamide (4h): LC-MS (Method B, retention time=0.335 min. MS calc'd for C$_{24}$H$_{31}$N$_4$O (MH$^+$): 391.3. Found 391.6.

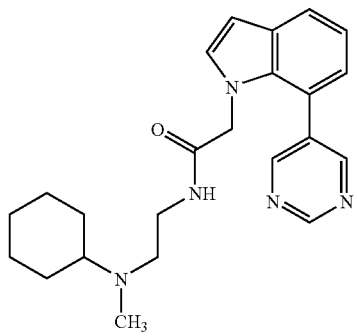

4i

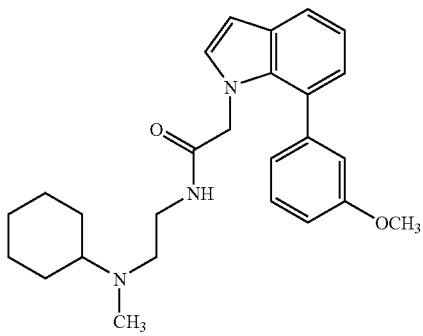

4l

N-[2-(Cyclohexyl-methyl-amino)-ethyl]-2-(7-pyrimidin-5-yl-indol-1-yl)-acetamide (4i): LC-MS (Method B, retention time=0.741 min. MS calc'd for $C_{23}H_{30}N_5O$ (MH$^+$): 392.3. Found 392.6.

N-[2-(Cyclohexyl-methyl-amino)-ethyl]-2-[7-(3-methoxy-phenyl)-indol-1-yl]-acetamide (4l): LC-MS (Method B, retention time=1.904 min. MS calc'd for $C_{26}H_{34}N_3O_2$ (MH$^+$): 420.3. Found 420.6.

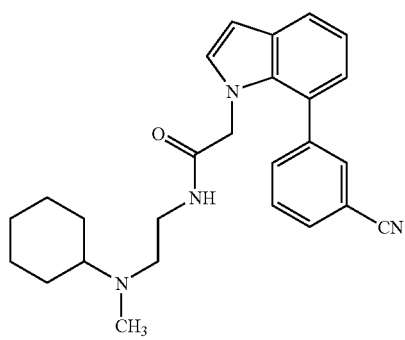

4j

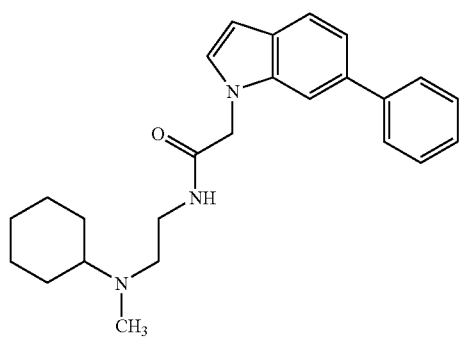

4m

2-[7-(3-Cyano-phenyl)-indol-1-yl]-N-[2-(cyclohexyl-methyl-amino)-ethyl]-acetamide (4j): LC-MS (Method B, retention time=1.888 min. MS calc'd for $C_{26}H_{31}N_4O$ (MH$^+$): 415.3. Found 415.6.

N-[2-(Cyclohexyl-methyl-amino)-ethyl]-2-(6-phenyl-indol-1-yl)-acetamide (4m): LC-MS (Method B, retention time=2.059 min. MS calc'd for $C_{25}H_{32}N_3O$ (MH$^+$): 390.3. Found 390.6.

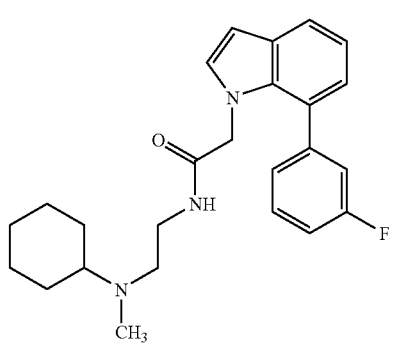

4k

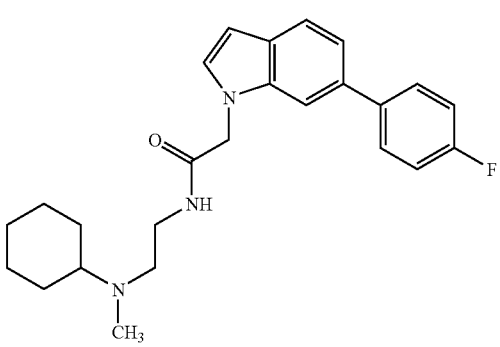

4n

N-[2-(Cyclohexyl-methyl-amino)-ethyl]-2-[7-(3-fluoro-phenyl)-indol-1-yl]-acetamide (4k): LC-MS (Method B, retention time=2.006 min. MS calc'd for $C_{25}H_{31}FN_3O$ (MH$^+$): 408.3. Found 408.2.

N-[2-(Cyclohexyl-methyl-amino)-ethyl]-2-[6-(4-fluoro-phenyl)-indol-1-yl]-acetamide (4n): LC-MS (Method B, retention time=1.880 min. MS calc'd for $C_{25}H_{31}FN_3O$ (MH$^+$): 408.3. Found 408.6.

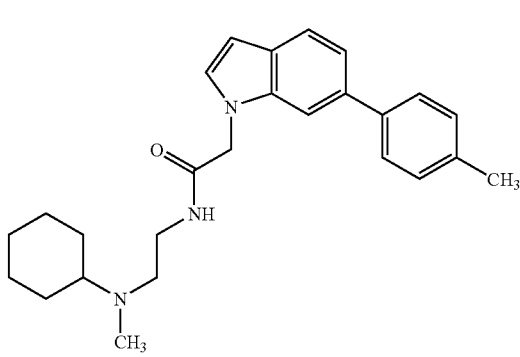

4o

N-[2-(Cyclohexyl-methyl-amino)-ethyl]-2-(6-p-tolyl-indol-1-yl)-acetamide (4o): LC-MS (Method B, retention time=2.187 min. MS calc'd for $C_{26}H_{34}N_3O$ (MH$^+$): 404.3. Found 404.6.

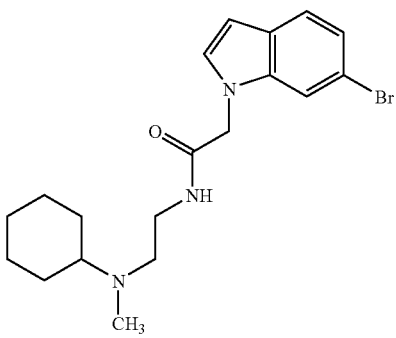

4r 2-(6-Bromo-indol-1-yl)-N-[2-(cyclohexyl-methyl-amino)-ethyl]-acetamide (4r): LC-MS (Method B, retention time=1.868 min. MS calc'd for $C_{19}H_{27}BrN_3O$ (MH$^+$): 392.1. Found 392.5.

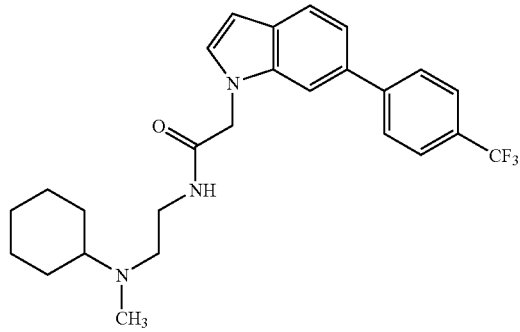

4p

N-[2-(Cyclohexyl-methyl-amino)-ethyl]-2-[6-(4-trifluoromethyl-phenyl)-indol-1-yl]-acetamide (4p): LC-MS (Method B, retention time=2.318 min. MS calc'd for $C_{26}H_{31}F_3N_3O$ (MH$^+$): 458.2. Found 458.6.

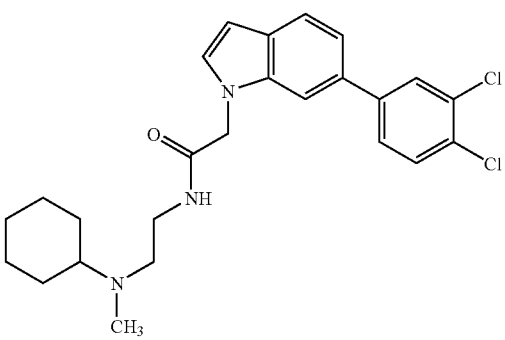

4t

N-[2-(Cyclohexyl-methyl-amino)-ethyl]-2-[6-(3,4-dichloro-phenyl)-indol-1-yl]-acetamide (4t): LC-MS (Method B, retention time=2.238 min. MS calc'd for $C_{25}H_{30}Cl_2N_3O$ (MH$^+$): 458.2. Found 458.5.

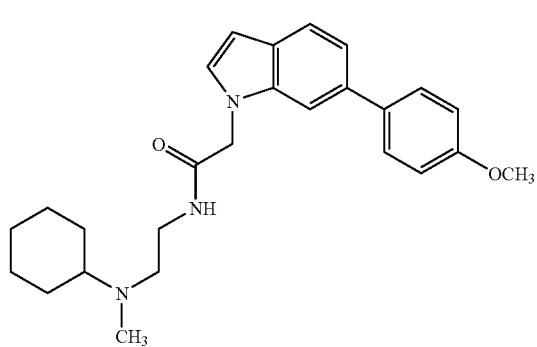

4q

N-[2-(Cyclohexyl-methyl-amino)-ethyl]-2-[6-(4-methoxy-phenyl)-indol-1-y]-acetamide (4q): LC-MS (Method B, retention time=2.035 min. MS calc'd for $C_{26}H_{34}N_3O_2$ (MH$^+$): 420.3. Found 420.6.

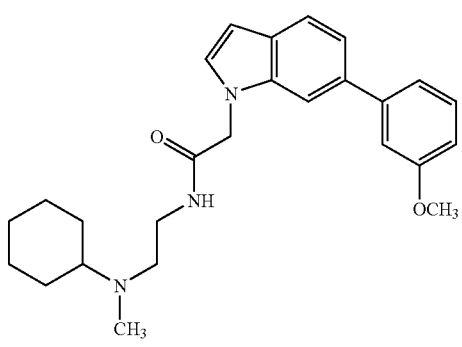

4u

N-[2-(Cyclohexyl-methyl-amino)-ethyl]-2-[6-(3-methoxy-phenyl)-indol-1-yl]-acetamide (4u): LC-MS (Method B, retention time=1.921 min. MS calc'd for $C_{26}H_{34}N_3O_2$ (MH$^+$): 420.3. Found 420.6.

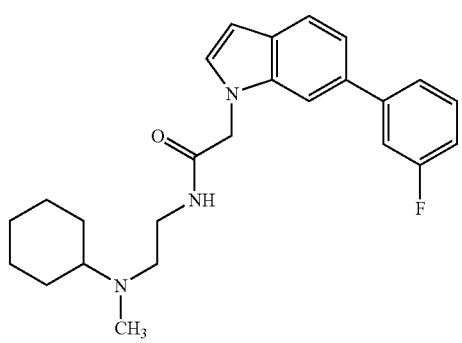

N-[2-(Cyclohexyl-methyl-amino)-ethyl]-2-[6-(3-fluoro-phenyl)-indol-1-yl]-acetamide (4v): LC-MS (Method B, retention time=1.938 min. MS calc'd for $C_{25}H_{31}FN_3O$ (MH+): 408.3. Found 408.6.

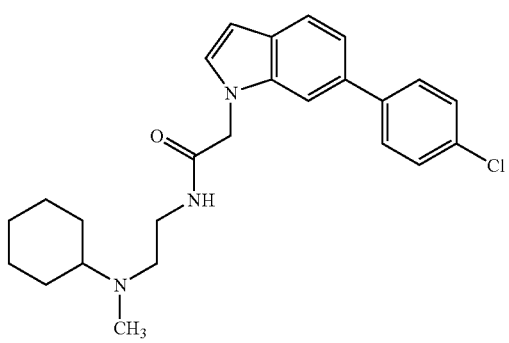

2-[6-(4-Chloro-phenyl)-indol-1-yl]-N-[2-(cyclohexyl-methyl-amino)-ethyl]-acetamide (4y): LC-MS (Method B, retention time=2.076 min. MS calc'd for $C_{25}H_{31}ClN_3O$ (MH+): 424.2. Found 424.6.

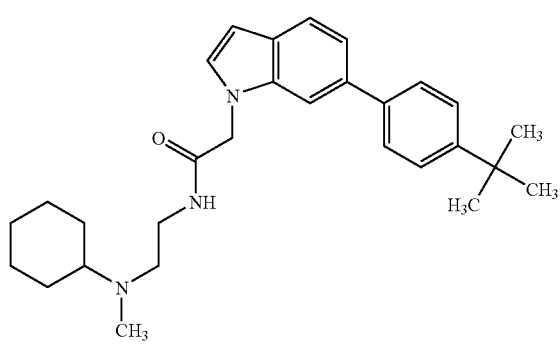

2-[6-(4-tert-Butyl-phenyl)-indol-1-yl]-N-[2-(cyclohexyl-methyl-amino)-ethyl]-acetamide (4w): LC-MS (Method B, retention time=2.365 min. MS calc'd for $C_{29}H_{40}N_3O$ (MH+): 446.3. Found 446.7.

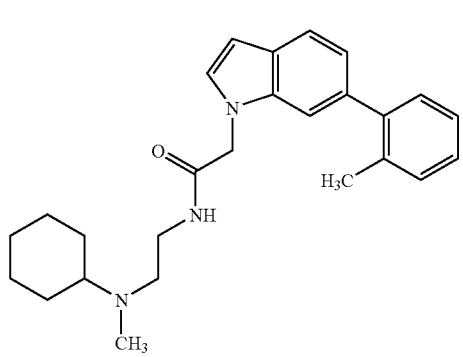

N-[2-(Cyclohexyl-methyl-amino)-ethyl]-2-(6-o-tolyl-indol-1-yl)-acetamide (4z): LC-MS (Method B, retention time=2.036 min. MS calc'd for $C_{26}H_{34}N_3O$ (MH+): 404.3. Found 404.6.

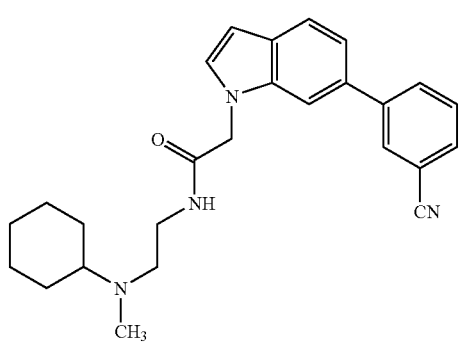

2-[6-(3-Cyano-phenyl)-indol-1-yl]-N-[2-(cyclohexyl-methyl-amino)-ethyl]-acetamide (4x): LC-MS (Method B, retention time=1.859 min. MS calc'd for $C_{26}H_{31}N_4O$ (MH+): 415.3. Found 415.6.

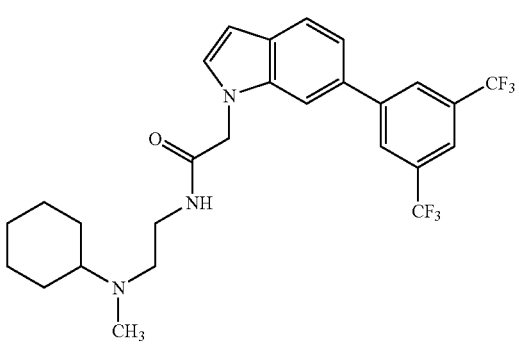

2-[6-(3,5-Bis-trifluoromethyl-phenyl)-indol-1-yl]-N-[2-(cyclohexyl-methyl-amino)-ethyl]-acetamide (4aa): LC-MS (Method B, retention time=2.446 min. MS calc'd for $C_{27}H_{30}F_6N_3O$ (MH+): 526.2. Found 526.6.

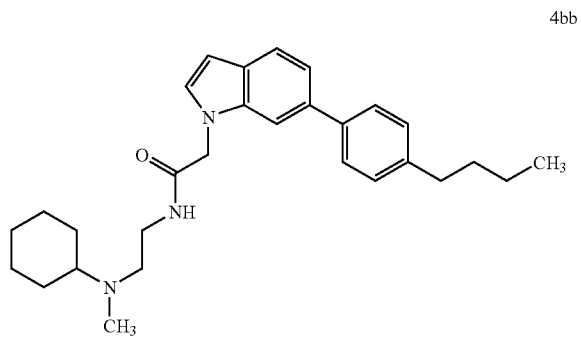

4bb

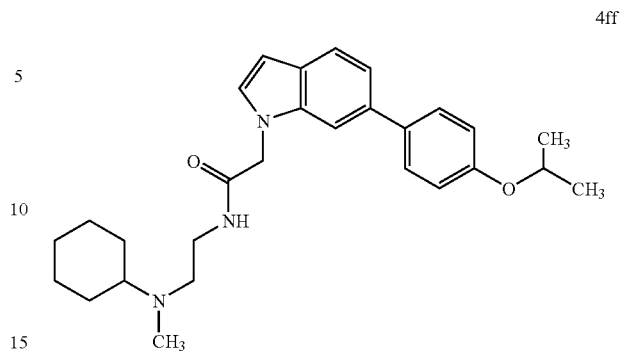

4ff

2-[6-(4-Butyl-phenyl)-indol-1-yl]-N-[2-(cyclohexyl-methyl-amino)-ethyl]-acetamide (4bb): LC-MS (Method B, retention time=2.456 min. MS calc'd for $C_{29}H_{40}N_3O$ (MH$^+$): 446.3. Found 446.7.

N-[2-(Cyclohexyl-methyl-amino)-ethyl]-2-[6-(4-isopropoxy-phenyl)-indol-1-yl]-acetamide (4ff): LC-MS (Method B, retention time=2.192 min. MS calc'd for $C_{28}H_{38}N_3O_2$ (MH$^+$): 448.3. Found 448.7.

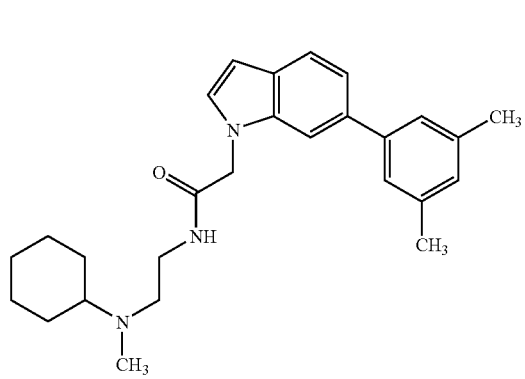

4cc

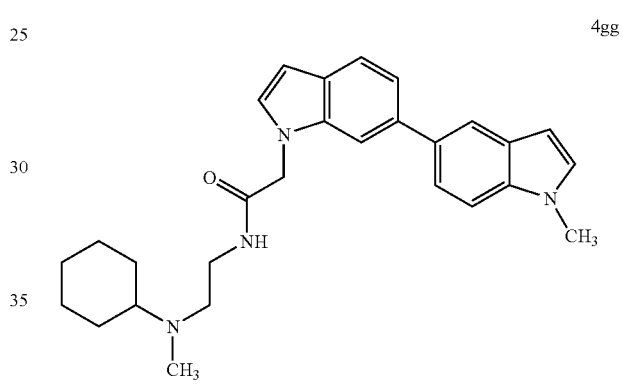

4gg

N-[2-(Cyclohexyl-methyl-amino)-ethyl]-2-[6-(3,5-dimethyl-phenyl)-indol-1-yl]-acetamide (4cc): LC-MS (Method B, retention time=2.211 min. MS calc'd for $C_{27}H_{36}N_3O$ (MH$^+$): 418.3. Found 418.6.

N-[2-(Cyclohexyl-methyl-amino)-ethyl]-2-(1-methyl-1H-[5,6']biindolyl-1'-yl)-acetamide (4gg): LC-MS (Method B, retention time=2.039 min. MS calc'd for $C_{28}H_{35}N_4O$ (MH$^+$): 443.3. Found 443.6.

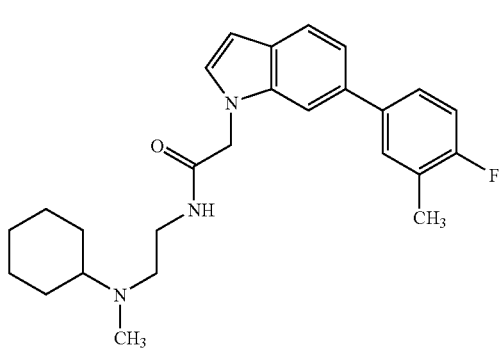

4dd

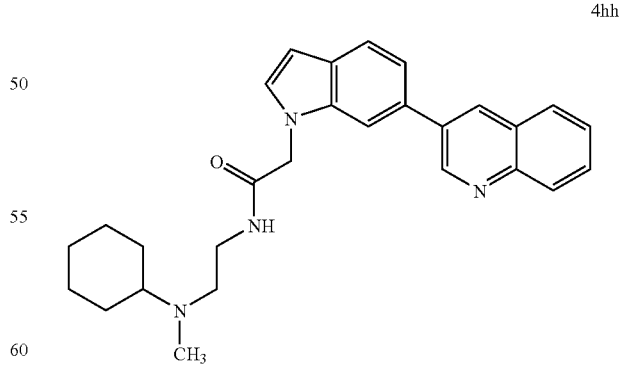

4hh

N-[2-(Cyclohexyl-methyl-amino)-ethyl]-2-[6-(4-fluoro-3-methyl-phenyl)-indol-1-yl]-acetamide (4dd): LC-MS (Method B, retention time=2.090 min. MS calc'd for $C_{26}H_{33}FN_3O$ (MH$^+$): 422.3. Found 422.6.

N-[2-(Cyclohexyl-methyl-amino)-ethyl]-2-(6-quinolin-3-yl-indol-1-yl)-acetamide (4hh): LC-MS (Method B, retention time=0.730 min. MS calc'd for $C_{28}H_{33}N_4O$ (MH$^+$): 441.3. Found 441.6.

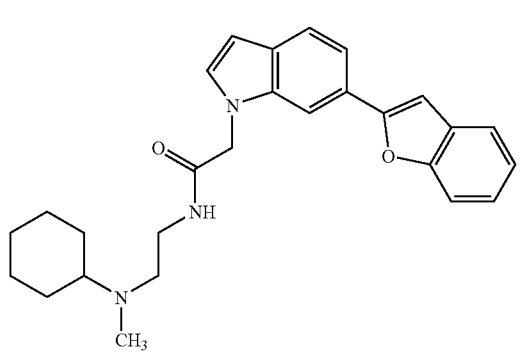

2-(6-Benzofuran-2-yl-indol-1-yl)-N-[2-(cyclohexyl-methyl-amino)-ethyl]-acetamide (4ii): LC-MS (Method B, retention time=2.115 min. MS calc'd for $C_{27}H_{32}N_3O_2$ (MH$^+$): 430.3. Found 430.6.

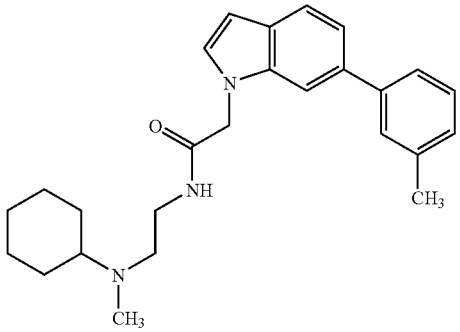

N-[2-(Cyclohexyl-methyl-amino)-ethyl]-2-(6-m-tolyl-indol-1-yl)-acetamide (4ll): LC-MS (Method B, retention time=2.083 min. MS calc'd for $C_{26}H_{34}N_3O$ (MH$^+$): 404.3. Found 404.6.

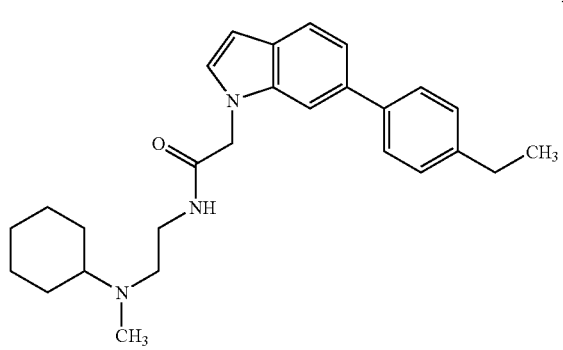

N-[2-(Cyclohexyl-methyl-amino)-ethyl]-2-[6-(4-ethyl-phenyl)-indol-1-yl]-acetamide (4jj): LC-MS (Method B, retention time=2.274 min. MS calc'd for $C_{27}H_{36}N_3O$ (MH$^+$): 418.3. Found 418.6.

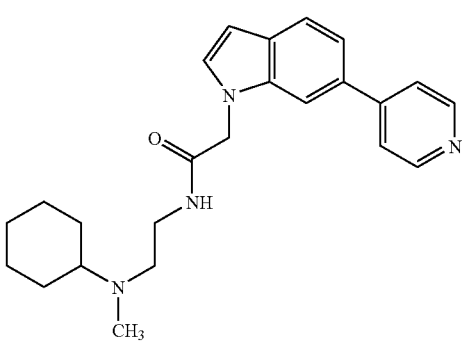

N-[2-(Cyclohexyl-methyl-amino)-ethyl]-2-(6-pyridin-4-yl-indol-1-yl)-acetamide (4 mm): LC-MS (Method B, retention time=0.264 min. MS calc'd for $C_{24}H_{31}N_4O$ (MH$^+$): 391.3. Found 391.6.

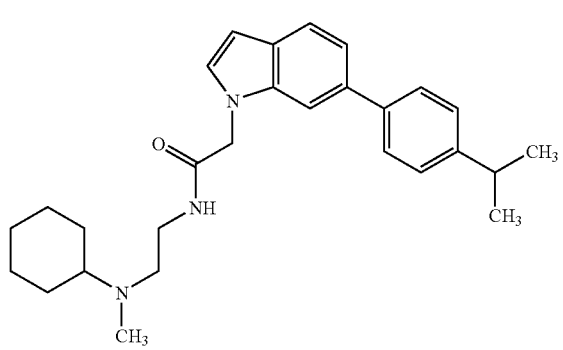

N-[2-(Cyclohexyl-methyl-amino)-ethyl]-2-[6-(4-isopropyl-phenyl)-indol-1-yl]-acetamide (4kk): LC-MS (Method B, retention time=2.353 min. MS calc'd for $C_{28}H_{38}N_3O$ (MH$^+$): 432.3. Found 432.7.

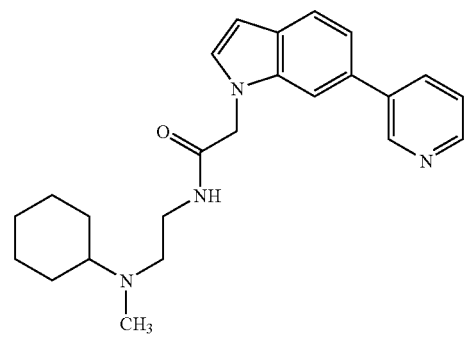

N-[2-(Cyclohexyl-methyl-amino)-ethyl]-2-(6-pyridin-3-yl-indol-1-yl)-acetamide (4nn): LC-MS (Method B, retention time=0.332 min. MS calc'd for $C_{24}H_{31}N_4O$ (MH$^+$): 391.3. Found 391.6.

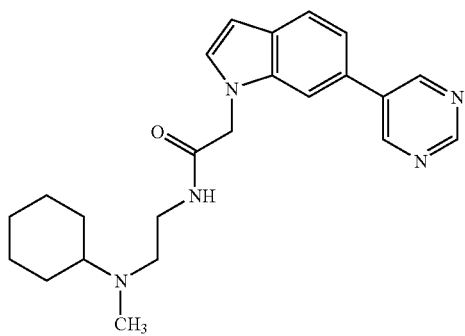

N-[2-(Cyclohexyl-methyl-amino)-ethyl]-2-(6-pyrimidin-5-yl-indol-1-yl)-acetamide (4oo): LC-MS (Method B, retention time=0.346 min. MS calc'd for $C_{23}H_{30}N_5O$ (MH$^+$): 392.3. Found 392.6.

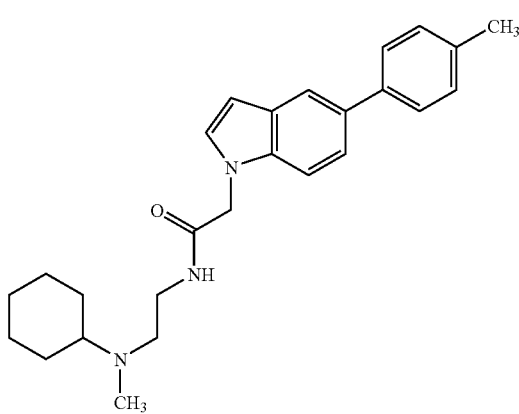

N-[2-(Cyclohexyl-methyl-amino)-ethyl]-2-(5-p-tolyl-indol-1-yl)-acetamide (4 pp): LC-MS (Method B, retention time=2.110 min. MS calc'd for $C_{26}H_{34}N_3O$ (MH$^+$): 404.3. Found 404.6.

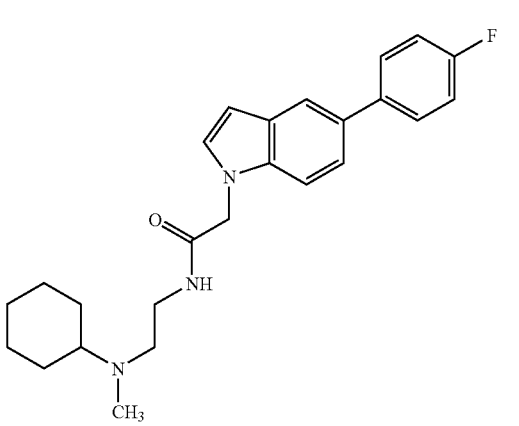

N-[2-(Cyclohexyl-methyl-amino)-ethyl]-2-[5-(4-fluorophenyl)-indol-1-yl]-acetamide (4qq): LC-MS (Method B, retention time=2.023 min. MS calc'd for $C_{25}H_{31}FN_3O$ (MH$^+$): 408.3. Found 408.6.

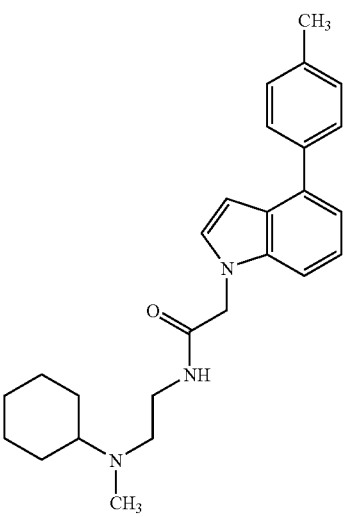

N-[2-(Cyclohexyl-methyl-amino)-ethyl]-2-(4-p-tolyl-indol-1-yl)-acetamide (4rr): LC-MS (Method B, retention time=2.065 min. MS calc'd for $C_{26}H_{34}N_3O$ (MH$^+$): 404.3. Found 404.6.

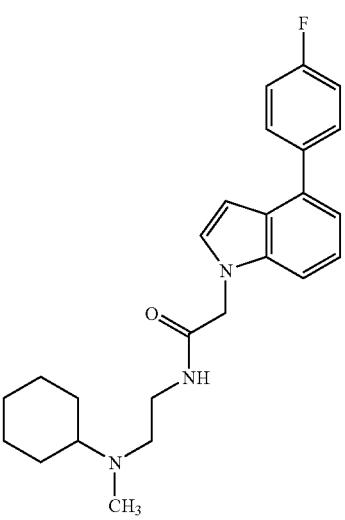

N-[2-(Cyclohexyl-methyl-amino)-ethyl]-2-[4-(4-fluorophenyl)-indol-1-yl]-acetamide (4ss): LC-MS (Method B, retention time=1.981 min. MS calc'd for $C_{25}H_{31}FN_3O$ (MH$^+$): 408.3. Found 408.6.

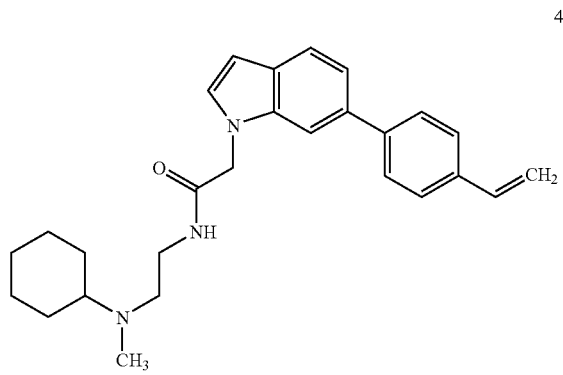

4tt

N-[2-(Cyclohexyl-methyl-amino)-ethyl]-2-[6-(4-vinyl-phenyl)-indol-1-yl]-acetamide (4tt): LC-MS (Method B, retention time=2.232 min. MS calc'd for $C_{27}H_{34}N_3O$ (MH+): 416.3. Found 416.6.

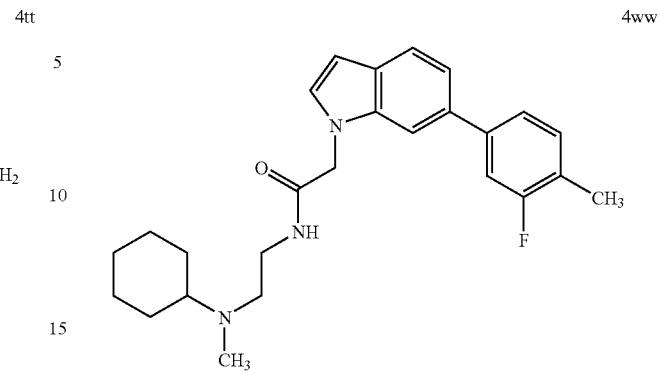

4ww

N-[2-(Cyclohexyl-methyl-amino)-ethyl]-2-[6-(3-fluoro-4-methyl-phenyl)-indol-1-yl]-acetamide (4ww): LC-MS (Method B, retention time=2.153 min. MS calc'd for $C_{26}H_{33}FN_3O$ (MH+): 422.3. Found 422.6.

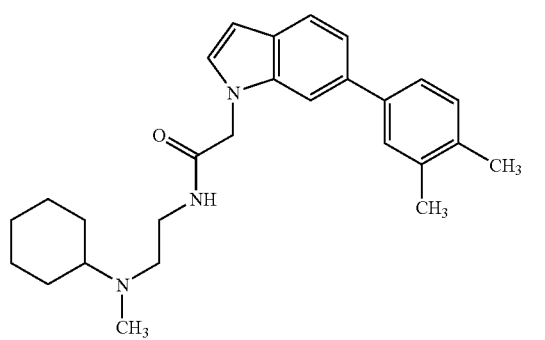

4uu

N-[2-(Cyclohexyl-methyl-amino)-ethyl]-2-[6-(3,4-dimethyl-phenyl)-indol-1-yl]-acetamide (4uu): LC-MS (Method B, retention time=2.218 min. MS calc'd for $C_{27}H_{36}N_3O$ (MH+): 418.3. Found 418.6.

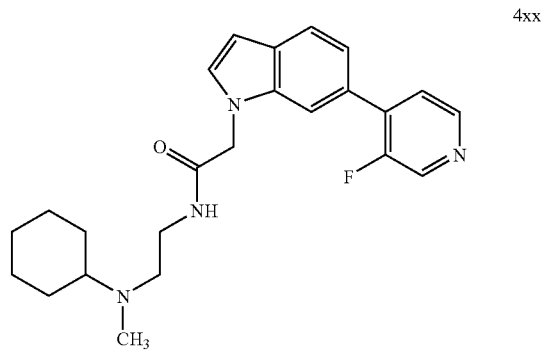

4xx

N-[2-(Cyclohexyl-methyl-amino)-ethyl]-2-[6-(3-fluoro-pyridin-4-yl)-indol-1-yl]-acetamide (4xx): LC-MS (Method B, retention time=0.489 min. MS calc'd for $C_{24}H_{30}FN_4O$ (MH+): 409.2. Found 409.6.

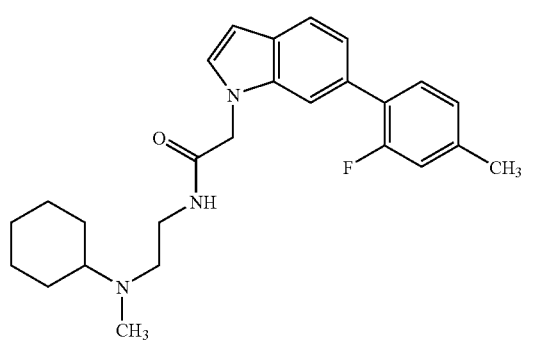

4vv

N-[2-(Cyclohexyl-methyl-amino)-ethyl]-2-[6-(2-fluoro-4-methyl-phenyl)-indol-1-yl]-acetamide (4vv): LC-MS (Method B, retention time=2.153 min. MS calc'd for $C_{26}H_{33}FN_3O$ (MH+): 422.3. Found 422.6.

4yy

N-[2-(Cyclohexyl-methyl-amino)-ethyl]-2-[6-(3-methoxy-pyridin-4-yl)-indol-1-yl]-acetamide (4yy): LC-MS (Method B, retention time=0.253 min. MS calc'd for $C_{25}H_{33}N_4O_2$ (MH+): 421.3. Found 421.6.

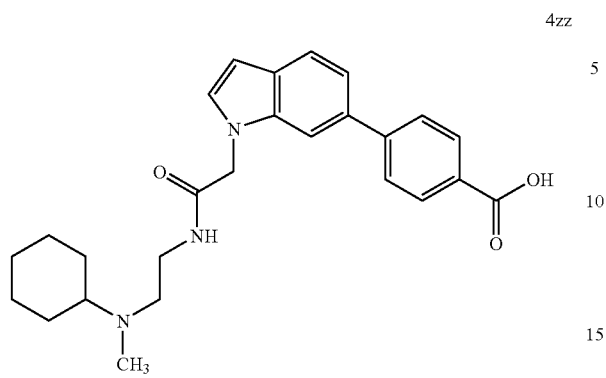

4zz

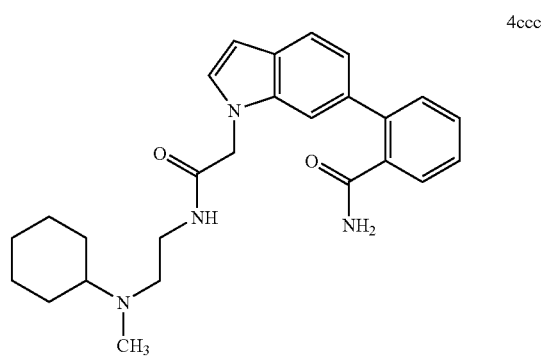

4ccc 4-(1-{[2-(Cyclohexyl-methyl-amino)-ethylcarbamoyl]-methyl}-1H-indol-6-yl)-benzoic acid (4zz): LC-MS (Method B, retention time=1.505 min. MS calc'd for $C_{26}H_{32}N_3O_3$ (MH$^+$): 434.2. Found 434.6.

2-(1-{[2-(Cyclohexyl-methyl-amino)-ethylcarbamoyl]-methyl}-1H-indol-6-yl)-benzamide (4 ccc): LC-MS (Method B, retention time=1.999 min. MS calc'd for $C_{26}H_{33}N_4O_2$ (MH$^+$): 433.3. Found 433.6.

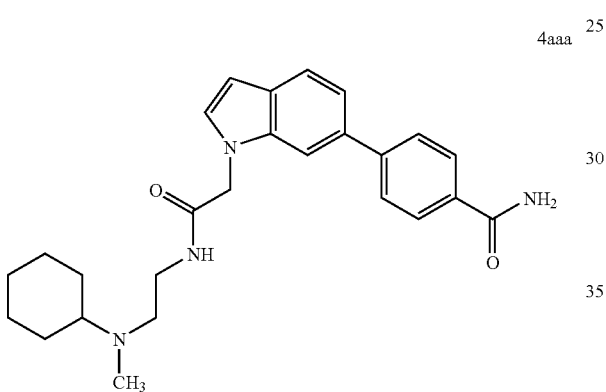

4aaa

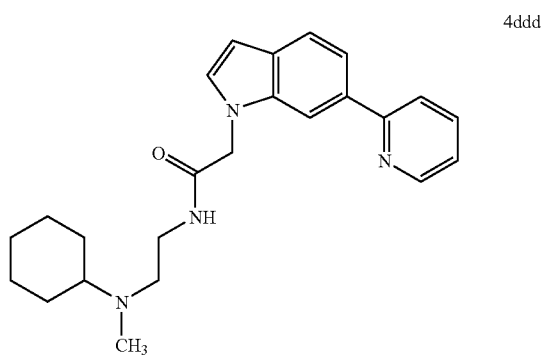

4ddd 4-(1-{[2-(Cyclohexyl-methyl-amino)-ethylcarbamoyl]-methyl}-1H-indol-6-yl)-benzamide (4aaa): LC-MS (Method B, retention time=0.640 min. MS calc'd for $C_{26}H_{33}N_4O_2$ (MH$^+$): 433.3. Found 433.6.

N-[2-(Cyclohexyl-methyl-amino)-ethyl]-2-(6-pyridin-2-yl-indol-1-yl)-acetamide (4ddd): LC-MS (Method B, retention time=0.336 min. MS calc'd for $C_{24}H_{31}N_4O$ (MH$^+$): 391.3. Found 391.3.

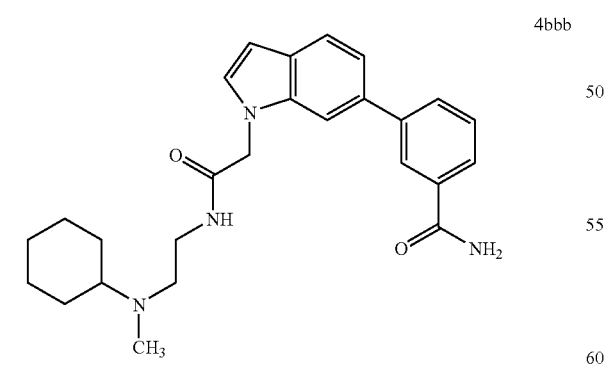

4bbb

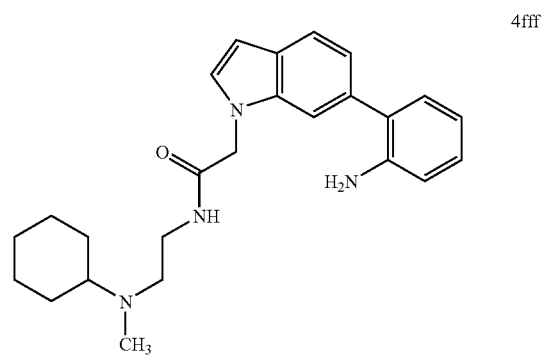

4fff 3-(1-{[2-(Cyclohexyl-methyl-amino)-ethylcarbamoyl]-methyl}-1H-indol-6-yl)-benzamide (4bbb): LC-MS (Method B, retention time=2.025 min. MS calc'd for $C_{26}H_{33}N_4O_2$ (MH$^+$): 433.3. Found 433.6.

2-[6-(2-Amino-phenyl)-indol-1-yl]-N-[2-(cyclohexyl-methyl-amino)-ethyl]-acetamide (4fff): LC-MS (Method B, retention time=2.072 min. MS calc'd for $C_{25}H_{33}N_4O$ (MH$^+$): 405.3. Found 405.5.

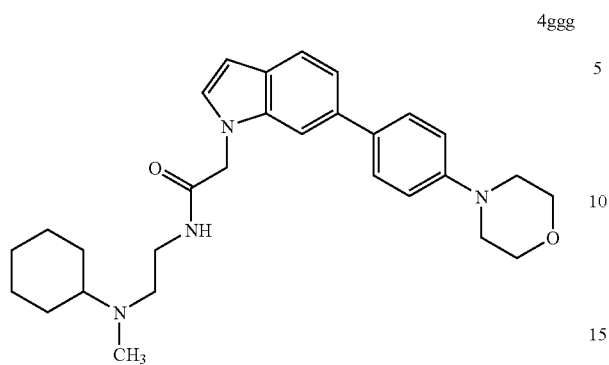

4ggg

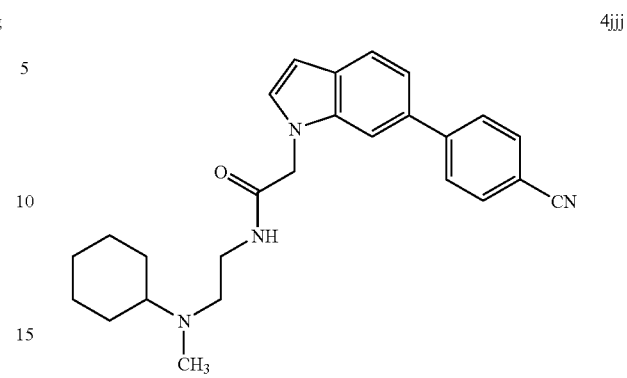

4jjj

N-[2-(Cyclohexyl-methyl-amino)-ethyl]-2-[6-(4-morpholin-4-yl-phenyl)-indol-1-yl]-acetamide (4ggg): LC-MS (Method B, retention time=2.287 min. MS calc'd for $C_{29}H_{39}N_4O_2$ (MH$^+$): 475.3. Found 475.5.

2-[6-(4-Cyano-phenyl)-indol-1-yl]-N-[2-(cyclohexyl-methyl-amino)-ethyl]-acetamide (4jjj): LC-MS (Method B, retention time=2.325 min. MS calc'd for $C_{26}H_{31}N_4O$ (MH$^+$): 415.3. Found 415.4.

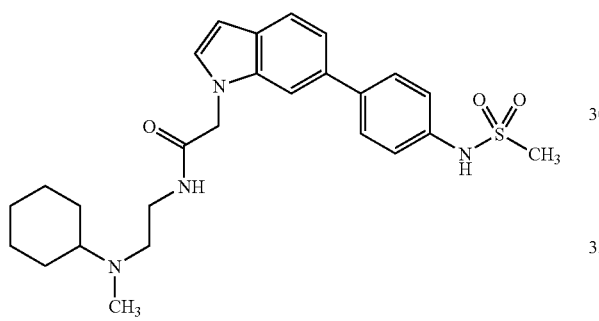

4hhh

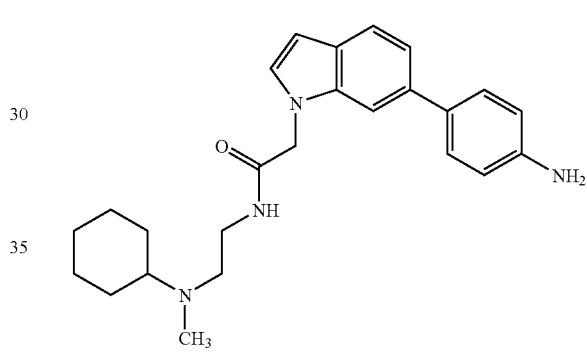

4kkk

N-[2-(Cyclohexyl-methyl-amino)-ethyl]-2-[6-(4-methanesulfonylamino-phenyl)-indol-1-yl]-acetamide (4hhh): LC-MS (Method B, retention time=2.200 min. MS calc'd for $C_{26}H_{35}N_4O_3S$ (MH$^+$): 483.2. Found 483.4.

2-[6-(4-Amino-phenyl)-indol-1-yl]-N-[2-(cyclohexyl-methyl-amino)-ethyl]-acetamide (4kkk): LC-MS (Method B, retention time=0.337 min. MS calc'd for $C_{25}H_{33}N_4O$ (MH$^+$): 405.3. Found 405.5.

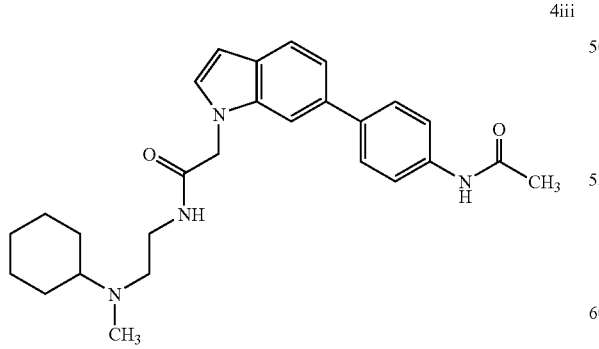

4iii

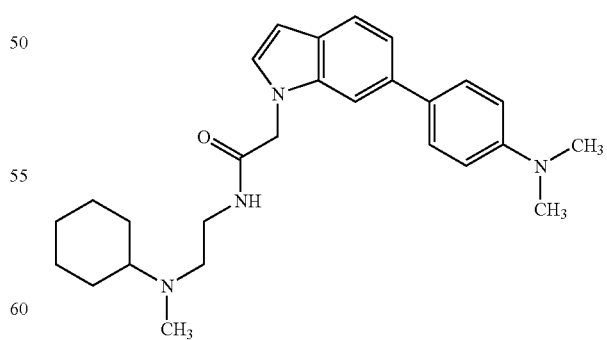

4lll

2-[6-(4-Acetylamino-phenyl)-indol-1-yl]-N-[2-(cyclohexyl-methyl-amino)-ethyl]-acetamide (4iii): LC-MS (Method B, retention time=2.110 min. MS calc'd for $C_{27}H_{35}N_4O_2$ (MH$^+$): 447.3. Found 447.5.

N-[2-(Cyclohexyl-methyl-amino)-ethyl]-2-[6-(4-dimethylamino-phenyl)-indol-1-yl]-acetamide (4lll): LC-MS (Method B, retention time=0.658 min. MS calc'd for $C_{27}H_{37}N_4O$ (MH$^+$): 433.3. Found 433.5.

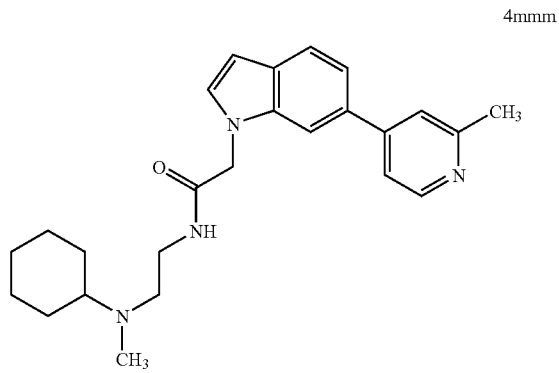

4mmm

N-[2-(Cyclohexyl-methyl-amino)-ethyl]-2-[6-(2-methyl-pyridin-4-yl)-indol-1-yl]-acetamide (4 mmm): LC-MS (Method A, retention time=1.881 min. MS calc'd for $C_{25}H_{33}N_4O$ (MH+): 405.3. Found 405.3.

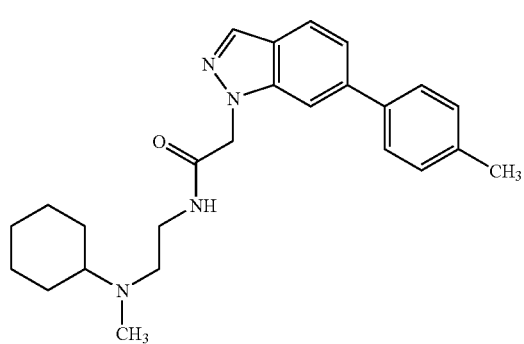

4nnn

N-[2-(Cyclohexyl-methyl-amino)-ethyl]-2-(6-p-tolyl-indazol-1-yl)-acetamide (4nnn): Compound 4nnn was prepared using 2-(6-Bromo-indazol-1-yl)-N-[2-(cyclohexyl-methyl-amino)-ethyl]-acetamide as a starting material: LC-MS (Method B, retention time=1.885 min. MS calc'd for $C_{25}H_{33}N_4O$ (MH+): 405.3. Found 405.6.

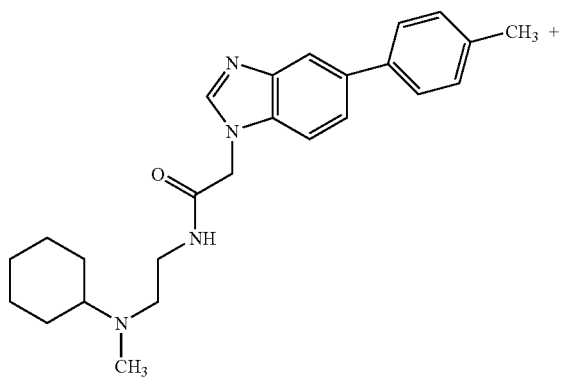

4ooo$^1$

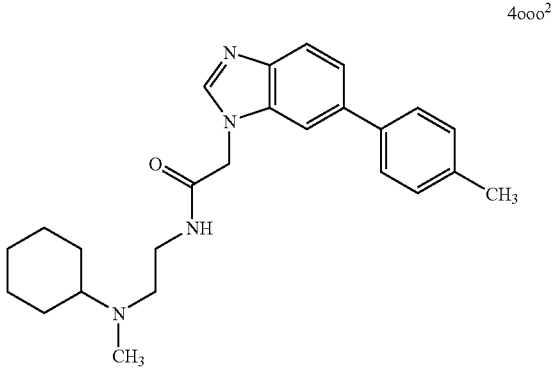

4ooo$^2$

N-[2-(Cyclohexyl-methyl-amino)-ethyl]-2-(5-p-tolyl-benzoimidazol-1-yl)-acetamide (4-ooo$^1$)/N-[2-(Cyclohexyl-methyl-amino)-ethyl]-2-(6-p-tolyl-benzoimidazol-1-yl)-acetamide (4ooo$^2$) (ratio 1:1): Compounds 4ooo$^1$ and 4ooo$^2$ were prepared using 2-(6-2-(5-Bromo-benzoimidazol-1-yl)-N-[2-(cyclohexyl-methyl-amino)-ethyl]-acetamide and Bromo-benzoimidazol-1-yl)-N-[2-(cyclohexyl-methyl-amino)-ethyl]-acetamide as the as the starting materials: LC-MS (Method B, retention time=0.552 min. MS calc'd for $C_{25}H_{33}N_4O$ (MH+): 405.3. Found 405.2.

4ppp 2-(6-Benzoyl-indol-1-yl)-N-[2-(cyclohexyl-methyl-amino)-ethyl]-acetamide (4ppp): Compound 4ppp was prepared following the synthetic procedure outlined in Examples 5 and 7 with the exception that CO atmosphere instead of $N_2$ atmosphere was used during the reaction: LC-MS (Method B, retention time=1.791 min. MS calc'd for $C_{26}H_{32}N_3O_2$ (MH+): 418.3. Found 418.6.

Example 8

Preparation of N-[3-(Cyclohexyl-methyl-amino)-propyl]-2-[7-(4-fluoro-phenyl)-indol-1-yl]-acetamide (6a)

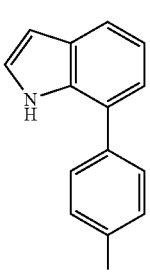

5a

1. ClCH$_2$CO$_2$Et, NaH
2. 1M LiOH(aq)/THF (1:2)
3. 2a, HATU, TEA, DMF
→

-continued

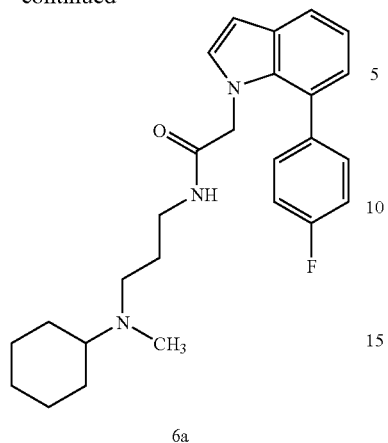

6a

The indole 5a (100 mg, 0.47 mmol) was dissolved in DMF (500 μL) and NaH (60% dispersed in mineral oil (27 mg, 0.7 mmol) was added. The mixture was heated to 65° C. and stirred for 30 minutes followed by the addition of ethyl chloroacetate (62 μL, 0.6 mmol). The reaction mixture was continued for 2 hours then cooled to room temperature and diluted in EtOAc. The organic solution was washed with water (2×) and brine (1×) and then dried over MgSO₄ and concentrated. The product was purified by column chromatography (1:8 EtOAc/hexanes). The resulting oil was diluted in THF (2 mL) and to it was added 1M LiOH(aq) (1 mL). The resultant solution was stirred for 6 hours then neutralized with 1N HCl and the concentrated in vacuo. The resulting yellowish powder was then combined with HATU (33 mg, 0.09 mmol), the amine (0.07 mmol) and dissolved in DMF (250 μL). To the reaction solution was added triethylamine (50 μL, 0.2 mmol) and the solution was stirred for 2 hours. The reaction mixture was diluted with sat'd NaHCO₃(aq) and the crude product was isolated by extraction with EtOAc (3×). The organic layers were dried over MgSO4 and concentrated to provide the crude product 6a which was purified by preparative TLC (1:1:0.25 EtOAc/hexanes/Et₃N) to give the indole product 6a (2.4 mg, 1.2% yield over 3 steps): LC-MS (Method B, retention time=2.219 min. MS calc'd for $C_{26}H_{33}FN_3O$ (MH⁺): 422.3. Found 422.2.

Example 9

The following compounds were made in similar yield using the same procedure with the appropriate amine as described in Example 8.

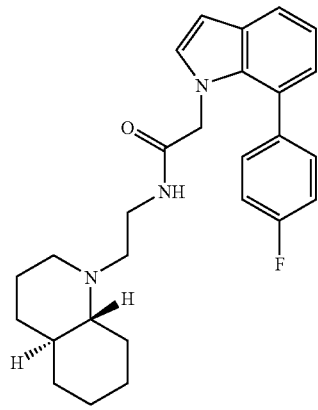

6b

2-[7-(4-Fluoro-phenyl)-indol-1-yl]-N-[2-(trans-octahydro-quinolin-1-yl)-ethyl]-acetamide (6b): LC-MS (Method B, retention time=2.409 min. MS calc'd for $C_{27}H_{33}FN_3O$ (MH⁺): 434.3. Found 434.6.

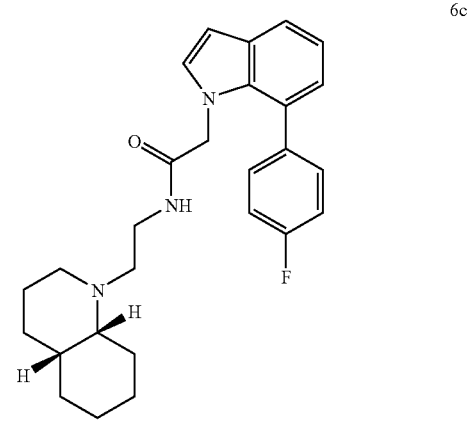

6c

2-[7-(4-Fluoro-phenyl)-indol-1-yl]-N-[2-(cis-octahydro-quinolin-1-yl)-ethyl]-acetamide (6c): LC-MS (Method B, retention time=2.387 min. MS calc'd for $C_{27}H_{33}FN_3O$ (MH⁺): 434.3. Found 434.6.

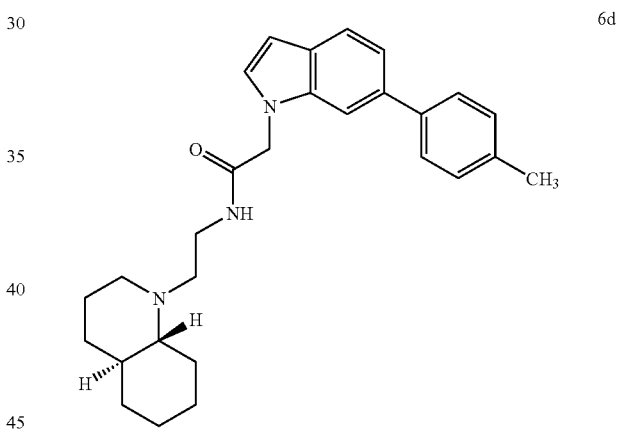

6d

N-[2-(trans-Octahydro-quinolin-1-yl)-ethyl]-2-(6-p-tolyl-indol-1-yl)-acetamide (6d): LC-MS (Method B, retention time=2.285 min. MS calc'd for $C_{28}H_{36}N_3O$ (MH⁺): 430.3. Found 430.6.

Example 10

Preparation of 2-Piperidin-1-yl-N-[2-(6-p-tolyl-indol-1-yl)-ethyl]-acetamide (10a)

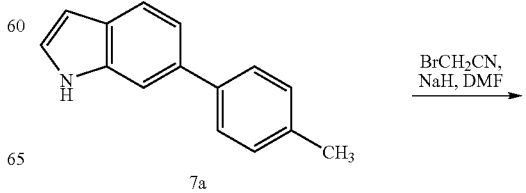

7a

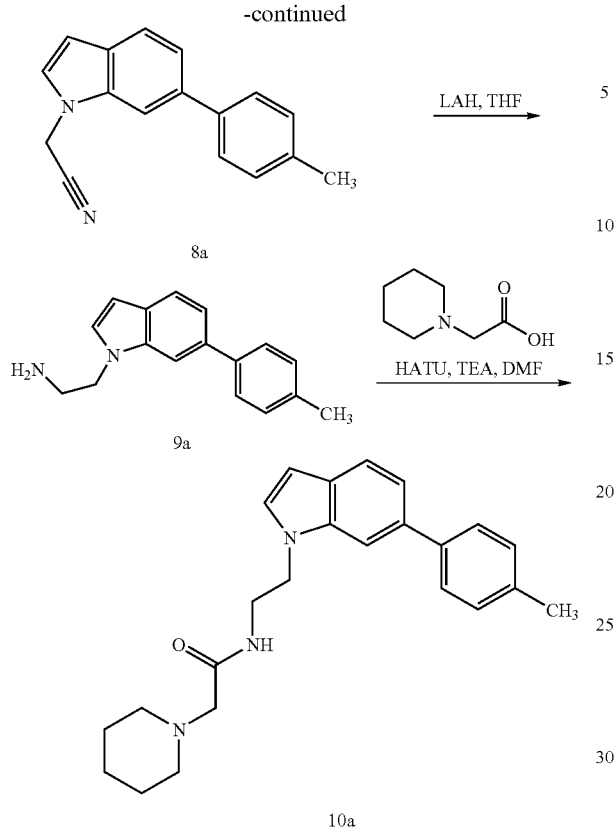

2-Piperidin-1-yl-N-[2-(6-p-tolyl-indol-1-yl)-ethyl]-acetamide (10a): (Indole 7a was prepared through the Suzuki described in Example 5. Indole 7a (100 mg, 0.48 mmol) was dissolved in DMF (1 mL) and NaH (60% dispersed in mineral oil, 29 mg, 0.72 mmol) was added at room temperature. The reaction mixture was stirred for 30 minutes then cooled to 0° C. To the cooled reaction solution was added dropwise bromoacetonitrile (50 μL, 0.72 mmol). The reaction solution was warmed to room temperature and stir for 12 hours. The reaction solution was diluted with $H_2O$ and extracted with EtOAc (3×). The organic layer was dried over $MgSO_4$, and concentrated to provide the desired product 8a which was used without further purification. The crude residue 8a (55 mg, 0.223 mmol) was dissolved in THF (6 mL) and cooled to 0° C. Lithium aluminum hydride (10 mg, 0.246 mmol) was then added and the reaction solution was stirred at 0° C. for 1 hour. The reaction solution was then quenched with 1N HCl (1 mL) at 0° C. and was extracted with $CH_2Cl_2$ (3×). The combined organic layer was dried over $MgSO_4$ and concentrated to provide 9a which was used without further purification. The crude residue 9a (16 mg, 0.06 mmol) was dissolved in DMF (500 μL) and the carboxylic acid (14 mg, 0.078 mmol) and HATU (29 mg, 0.078 mmol) were added followed by TEA (40 μL, 0.18 mmol). The reaction was allowed to stir at room temperature for 2 hours then diluted with $H_2O$, extracted with EtOAc (3×) dried over ($MgSO_4$) and concentrated to provide 10a. Crude 10a was purified by preparative TLC (1:1:0.25 EtOAc/hexanes/TEA) to provide 4.2 mg of indole 10a (2.3% yield over 3 steps): LC-MS (Method B, retention time=2.039 min. MS calc'd for $C_{24}H_{30}N_3O$ ($MH^+$): 376.2. Found 376.4.

Example 11

Preparation of N-[2-(Cyclohexyl-methyl-amino)-ethyl]-2-(1H-indol-3-yl)-acetamide (11a)

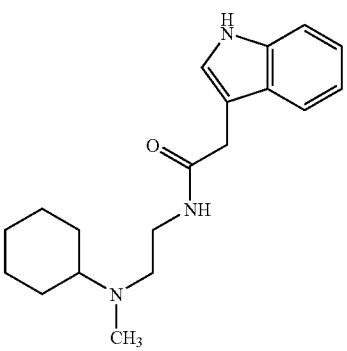

N-[2-(Cyclohexyl-methyl-amino)-ethyl]-2-(1H-indol-3-yl)-acetamide (11a): Compound 11a was prepared using the amino acid coupling procedure described in Example 10 using (1H-indol-3-yl)-acetic acid and $N^1$-Cyclohexyl-$N^1$-methyl-ethane-1,2-diamine as the starting materials: LC-MS (Method B, retention time=0.516 min. MS calc'd for $C_{19}H_{28}N_3O$ ($MH^+$): 314.2. Found 314.5.

Example 12

Preparation of N-[2-(Cyclohexyl-methyl-amino)-ethyl]-3-(1H-indol-3-yl)-propionamide (12a)

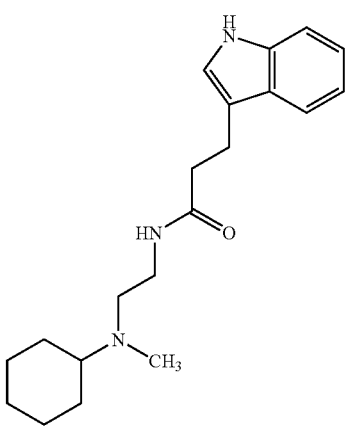

N-[2-(Cyclohexyl-methyl-amino)-ethyl]-3-(1H-indol-3-yl)-propionamide (12a): Compound 12a was prepared using the amino acid coupling procedure described in Example 10 using 3-(1H-Indol-3-yl)-propionic acid and $N^1$-Cyclohexyl-$N^1$-methyl-ethane-1,2-diamine as the starting materials: LC-MS (Method B, retention time=0.427 min. MS calc'd for $C_{20}H_{30}N_3O$ ($MH^+$): 328.2. Found 328.2.

Example 13

Preparation of 1-{[2-(Cyclohexyl-methyl-amino)-ethylcarbamoyl]-methyl}-6-p-tolyl-1H-indole-2-carboxylic acid methyl ester (15a)

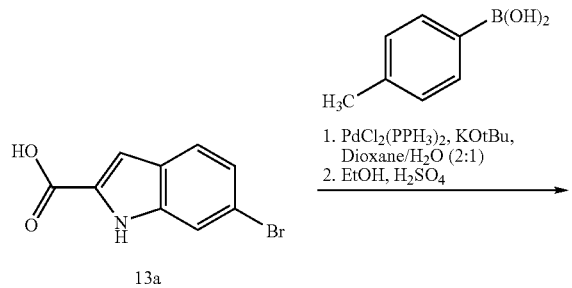

13a

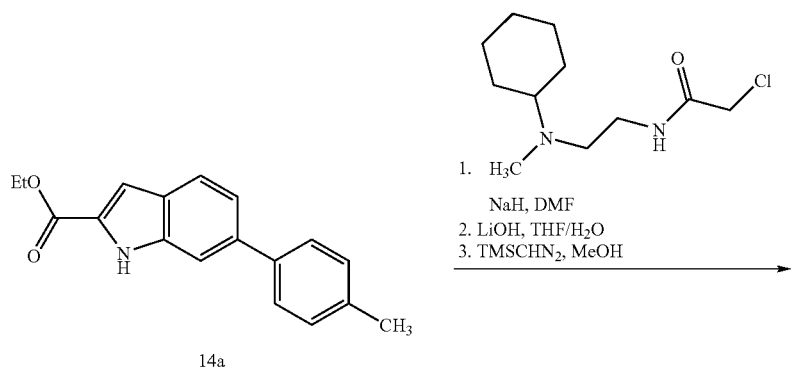

14a

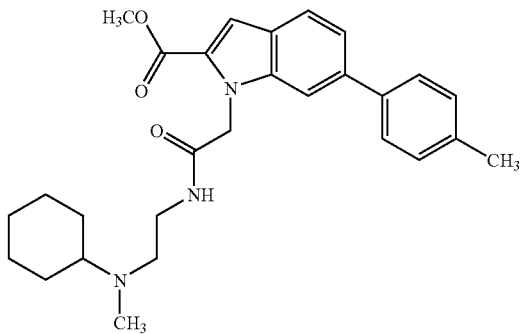

15a

Indole 13a (500 mg, 2.08 mmol) was combined with p-tolylboronic acid (368 mg, 2.7 mmol) and $PdCl_2(PPh_3)_2$ (catalytic amount) in a sealed vial and the reagents were dissolved with 4 mL of Dioxane/$H_2O$ (4:1). To the resultant solution was added 1M KOtBu in THF (3.3 mL) and the reaction mixture was heated to 80° C. under nitrogen atmosphere for 12 hours. The solvent was removed under reduced pressure and the crude product purified by column chromatography (100% EtOAc). The product was then dissolved in a solution of EtOH which contained a catalytic amount of $H_2SO_4$. The resultant solution was stirred at rt, then concentrated to provide the ethyl ester product 14a. Compound 14a was used in the alkylation reaction as described in step 3 of Example 1. The resultant alkylated material was treated under the reaction conditions of LiOH in THF/water to provide the saponified carboxylic acid product. The isolated carboxylic acid product (70 mg, 0.156 mmol) was dissolved in MeOH (2 mL) and to the resultant solution was added $TMSCHN_2$ (2M in $Et_2O$) (170 μL) and stirred for 1 hour. The solvent was removed under reduced pressure to provide crude product 15a which was purified by column chromatography (1:2:0.25 (EtOAc/hexanes/TEA) to provide 1.5 mg of indole 15a: LC-MS (Method B, retention time=2.378 min. MS calc'd for $C_{28}H_{36}N_3O_3$ $(MH^+)$: 462.3. Found 462.4.

Example 14

Preparation of 1-{[2-(Cyclohexyl-methyl-amino)-ethylcarbamoyl]-methyl}-6-p-tolyl-1H-indole-2-carboxylic acid (16a)

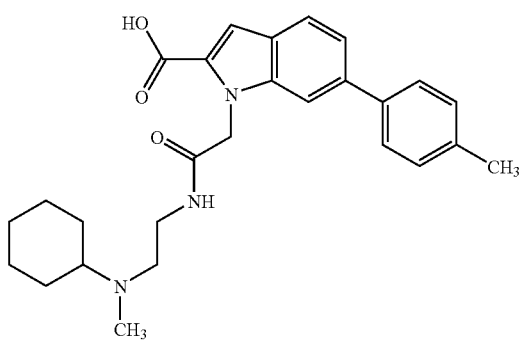

The methyl ester (15a) obtained above (2.7 mg, 0.006 mmol) was dissolved in THF (600 µL) and to the resultant solution was added 300 µL of a 3M NaOH(aq) and the reaction solution was stirred at rt. The crude product 16a was purified by HPLC (MeCN/H2O/0.1% TFA) to give 1.5 mg (16a): LC-MS (Method B, retention time=2.172 min. MS calc'd for $C_{27}H_{34}N_3O_3$ (MH$^+$): 448.3. Found 448.5.

Example 15

Preparation of 4-p-Tolyl-1H-indole-2-carboxylic acid [2-(cyclohexyl-methyl-amino)-ethyl]-amide (22a)

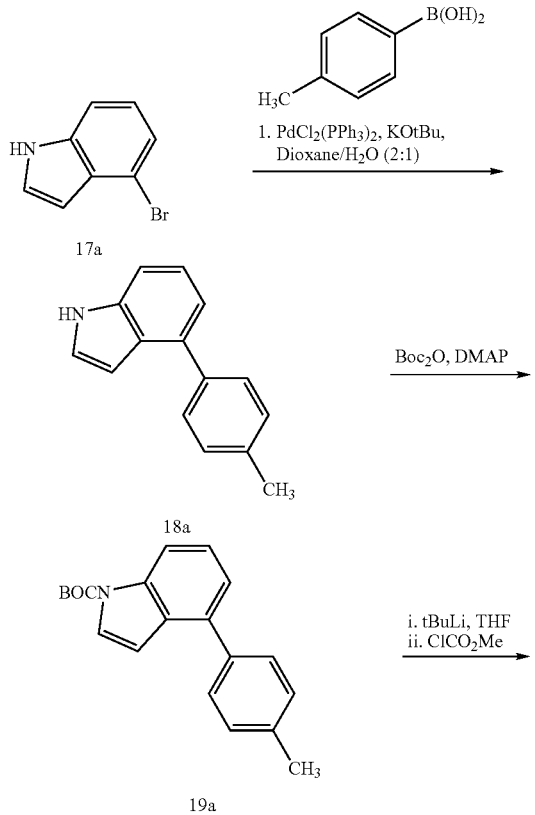

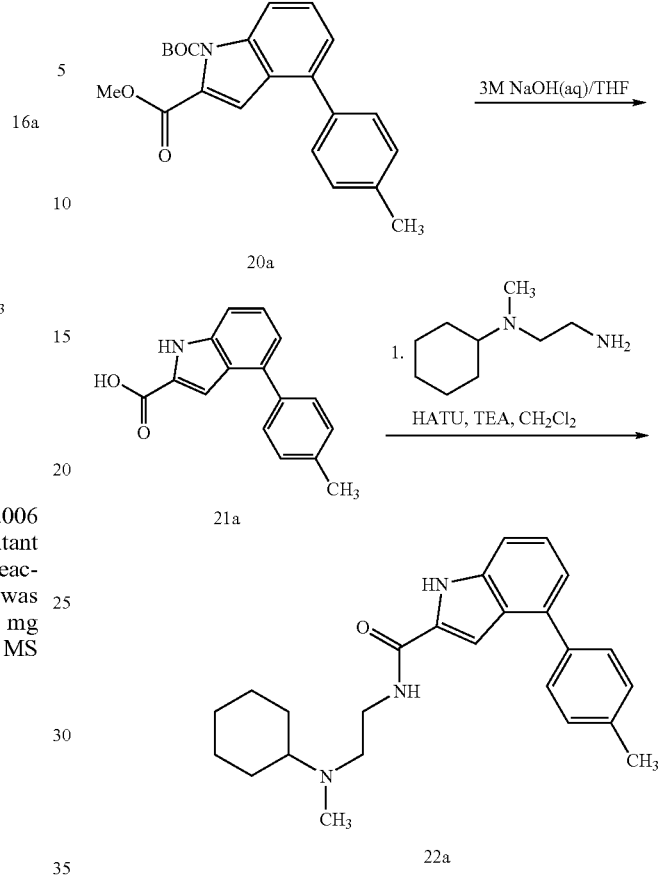

Tolyl boronic acid (630 mg) was reacted with indole bromide 17a (700 mg) using the Suzuki conditions as described in Example 13 to provide compound 18a. Compound 18a (100 mg, 0.483 mmol) was dissolved in $CH_2Cl_2$ (2 mL) and to the reaction solution was added DMAP (catalytic amount) followed by Boc$_2$O (120 mg, 0.531). The resultant solution was stirred for 5 hours at rt. The reaction mixture was then washed with brine (2×), dried over MgSO$_4$, concentrated and purified by column chromatography (1:6 EtOAc/hexanes) to provide indole 19a. Compound 19a (26 mg, 0.085 mmol) was then dissolved in THF (500 µL) and cooled to −78° C. under nitrogen atmosphere. To the cooled solution was added dropwise t-Butyl Lithium (1.7M in pentane, 230 µL, 0.39 mmol) and the reaction mixture was stirred for 1 hour. Then to the solution was added dropwise methyl chloroformate (30 µL, 0.39 mmol) and the resultant mixture was stirred at −78 C for 10 minutes and warmed room temperature over 1 hour. The reaction solution was quenched with H$_2$O and extracted with Et$_2$O (2×), dried over MgSO$_4$, and concentrated to provide compound 20a. Compound 20a was dissolved in a solution of THF and 3M NaOH(aq) and stirred at rt to produced the provide compound 21a. The isolated carboxylic acid 21a (11 mg, 0.044 mmol) was combined with the N$^1$-Cyclohexyl-N$^1$-methyl-ethane-1,2-diamine (8.2 mg, 0.057 mmol) and HATU (20 mg, 0.057 mmol) and dissolved in DMF (100 µL). To the resultant solution was added TEA (20 µL, 0.1 mmol) and the reaction solution was stirred at room temperature for 1 hour. The reaction mixture was then diluted with H$_2$O and the crude product 22a was extracted with EtOAc (3×). Crude 22a was then purified by HPLC (MeCN/H$_2$O/0.1% TFA) followed by preparative TLC (1:1:0.25 EtOAc/hexanes/TEA) to give 1.6 mg of indole 22a: LC-MS (Method B, retention time=2.528 min. MS calc'd for $C_{25}H_{32}N_3O$ (MH$^+$): 390.3. Found 390.4.

Example 16

Preparation of N-[2-(Cyclohexyl-methyl-amino)-ethyl]-2-(7-trifluoromethyl-indazol-1-yl)-acetamide (27a)

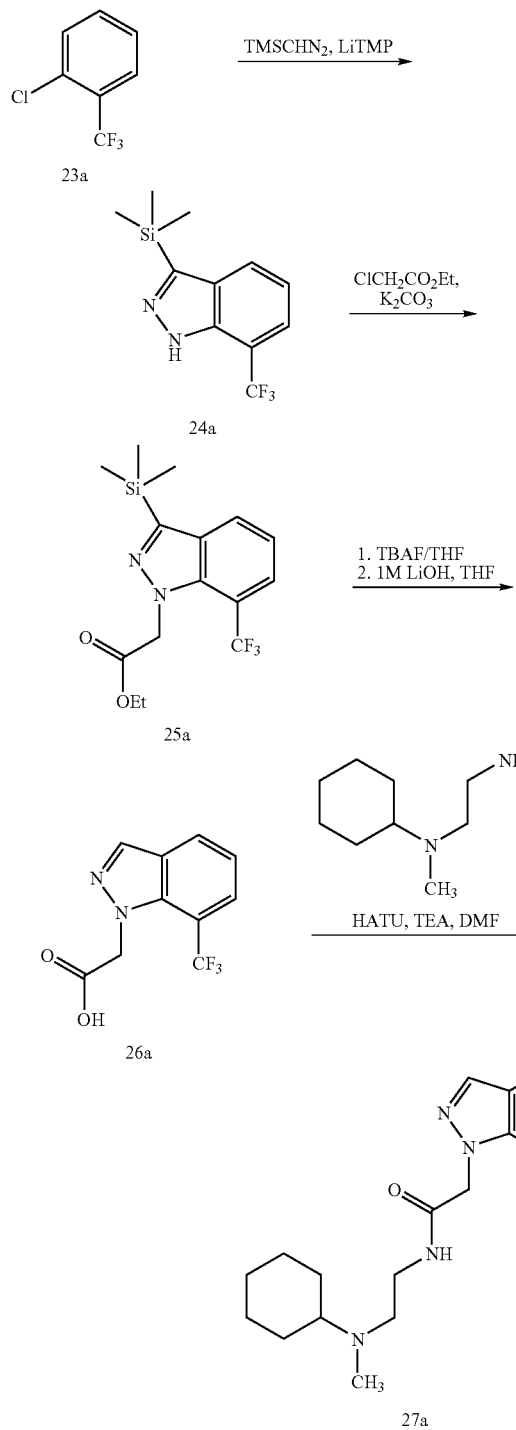

and the resultant solution was cooled to −78° C. and to it was added dropwise a solution of TMSCHN₂ (2.0M in THF) (1.13 mL, 2.26 mmol). The mixture was stirred for 15 minutes. To the cooled solution was added dropwise aryl chloride 23a (202 mg, 1.12 mmol) in THF (1.12 mL) and the reaction mixture was heated to 45° C. for 2 hours. The reaction was quenched with ice, diluted with EtOAc, and washed with sat'd NaHCO3(aq) and brine. The organic layer was dried over MgSO₄, concentrated under reduced pressure to provide pyrazole 24a which was purified by preparative TLC (1:6 EtOAc/hexanes). The isolated product 24a (59 mg, 0.23 mmol) was dissolved in DMF (500 μL) and to the resultant solution was added K₂CO₃ (70 mg, 0.51 mmol) and ethyl chloroacetate (30 μL, 0.28 mmol). The reaction solution was stirred at 70° C. for 12 hours. The reaction mixture was cooled to rt and the solvent was removed under reduced pressure. The crude product 25a was purified by column chromatography (1:7 EtOAc/hexanes). The purified product 25a was dissolved in a solution of tetrabutylammonium fluoride (TBAF)/THF and stirred at rt which results in the removal of the trimethyl silyl group on compound 25a; and the isolated desired product from this reaction was then dissolved in a solution of 1M LiOH (aq.)/THF and stirred at rt. The solution was neutralized with 1N HCl and the solvents removed to produce compound 26a. The resulting carboxylic acid 26a was coupled to $N^1$-Cyclohexyl-$N^1$-methyl-ethane-1,2-diamine (5.3 mg) in the presence of HATU (16.3 mg) and TEA (33 μL) in DMF (200 μL) as described in Example 15. The crude product 27a was purified by column chromatography (1:2:0.25 EtOAc/hexanes/TEA), to provide 5 mg of indazole 27a were obtained: LC-MS (Method B, retention time=1.402 min. MS calc'd for $C_{19}H_{26}F_3N_4O$ (MH⁺): 383.2. Found 383.5.

Example 17

Preparation of N-[2-(Cyclohexyl-methyl-amino)-ethyl]-2-(3-phenyl-6-p-tolyl-indazol-1-yl)-acetamide (35a)

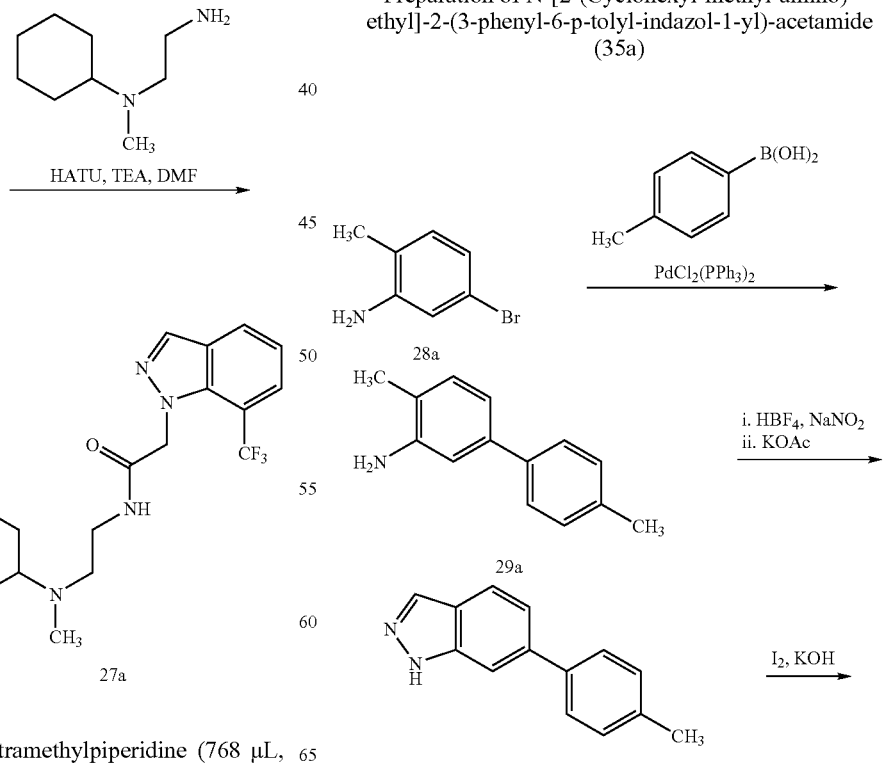

To a solution of 2,2,6,6-tetramethylpiperidine (768 μL, 4.52 mmol) in THF (3.4 mL) was added butyl lithium (2.5 M) (1.80 mL) to generate lithium 2,2,6,6-tetramethylpiperidide;

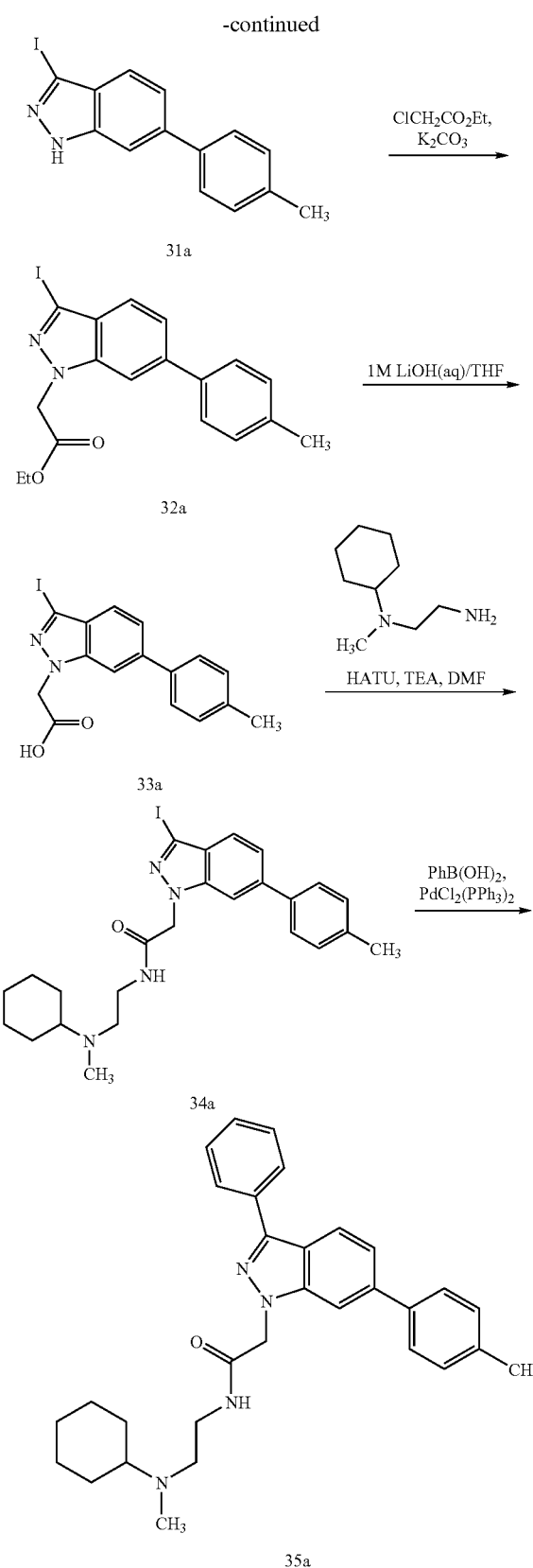

was added and the reaction was stirred at 80° C. for 12 hours. The solvent was removed under reduced pressure and the product was purified by column chromatography (1:2 EtOAc/hexanes) to provide compound 29a. Compound 29a (100 mg, 0.51 mmol) was mixed with $HBF_4$ (48% wt in $H_2O$) and EtOH (5 mL). The resultant solution was cooled to 0° C. and $NaNO_2$ (70 mg, 1.0 mmol) in $H_2O$ (300 μL) was added dropwise to the solution and the reaction mixture was stirred for 30 minutes. Then $Et_2O$ (15 mL) was added to the reaction mixture and the reaction solution was stirred for 30 minutes resulting in the precipitation of a yellow-brown solid which was filtered, washed with cold $H_2O$ and $Et_2O$ and dried. The isolated solid was dissolved in $CHCl_3$ (3.4 mL) and to it was added KOAc (70 mg, 0.68 mmol) and dibenzo 18Cr6 (Cas No. 14187-32-7) (6 mg, 0.017 mmol) were added and the reaction was allowed to stir for 2 hours. The reaction mixture was diluted with $Et_2O$ and the product 30a was isolated by filtration. Compound 30a (1.114 g, 5.3 mmol) was dissolved in DMF (10 mL) and to the resultant solution was added KOH (1.2 g, 10.7 mmol) and 1 (2.8 g, 5.6 mmol). The reaction solution was heated to 60° C. for 3 hours, then cooled to room temperature and diluted with sat'd $Na_2SSO_3$(aq). The crude product was extracted with EtOAc (3×), and the combined organic layer was dried and concentrated to provide 31a. Compound 31a was converted to compound 34a following similar procedures as were described in Example 16. The product obtained from this sequence, i.e. compound 34a (14 mg, 0.025 mmol), was combined with phenylboronic acid (5 mg, 0.034 mmol) and $PdCl_2(PPh3)_2$ (catalytic amount), and dissolved in 500 μL of Dioxane/$H_2O$ (4:1). To the resultant solution was added 1M KOtBu in THF (100 μL) and the reaction solution was stirred at 80° C. for 12 hours. The reaction solution was then removed under reduced pressure and the product 35a was purified by preparative TLC (1:3: 0.25 EtOAc/hexanes/TEA) to 9.0 mg of indazole 35a: LC-MS (Method B, retention time=2.304 min. MS calc'd for $C_{31}H_{37}N_4O$ (MH+): 481.3. Found 481.5.

Example 18

The synthetic procedure described for Example 17 was used to prepare the compounds below.

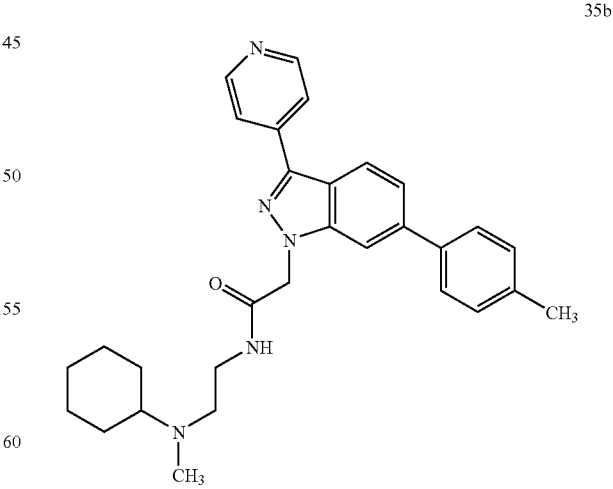

35b

Aniline 28a (5g) was combined with p-tolylboronic acid (4.7 g) and $PdCl_2(PPh_3)_2$ (catalytic amount) and dissolved in 50 mL of Dioxane/$H_2O$ (4:1). 1M KOtBu in THF (40 mL)

N-[2-(Cyclohexyl-methyl-amino)-ethyl]-2-(3-pyridin-4-yl-6-p-tolyl-indazol-1-yl)-acetamide (35b): LC-MS (Method A, retention time=2.085 min. MS calc'd for $C_{30}H_{36}N_5O$ (MH+): 482.3. Found 482.4.

35c

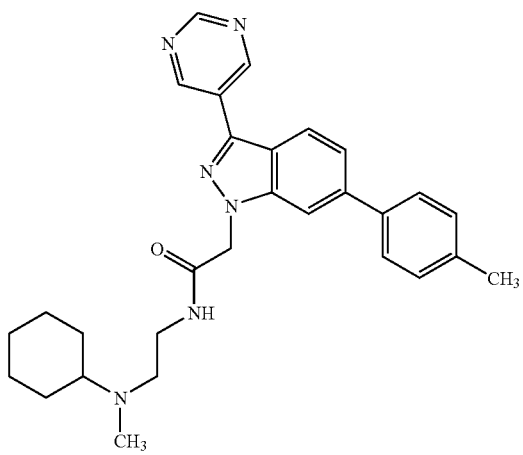

N-[2-(Cyclohexyl-methyl-amino)-ethyl]-2-(3-pyrimidin-5-yl-6-p-tolyl-indazol-1-yl)-acetamide (35c): LC-MS (Method A, retention time=2.414 min. MS calc'd for $C_{29}H_{35}N_6O$ (MH$^+$): 483.3. Found 483.5.

Example 19

Preparation of N-[2-(Cyclohexyl-methyl-amino)-ethyl]-2-(2-oxo-5-p-tolyl-benzooxazol-3-yl)-acetamide (36a)

36a

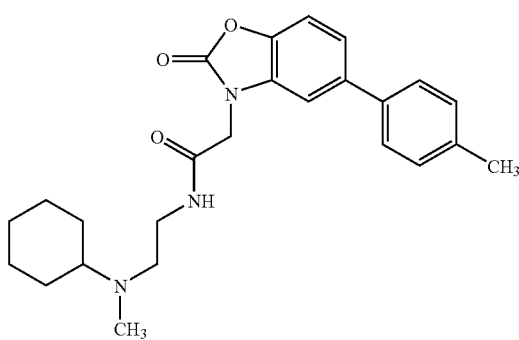

Compound 36a was prepared using 6-bromooxazolinone as the starting material (instead of aniline 28a and following the synthetic procedure outlined in Example 17: LC-MS (Method B, retention time=2.426 min. MS calc'd for $C_{25}H_{32}N_3O_3$ (MH$^+$): 422.2. Found 422.6.

Example 20

Preparation of 2-(4-Chloro-pyrazolo[4,3-c]pyridin-1-yl)-N-[2-(cyclohexyl-methyl-amino)-ethyl]-acetamide (40a)

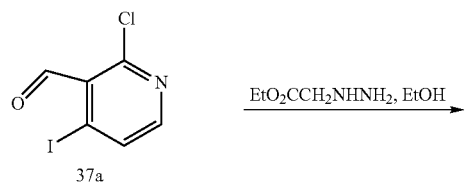

-continued

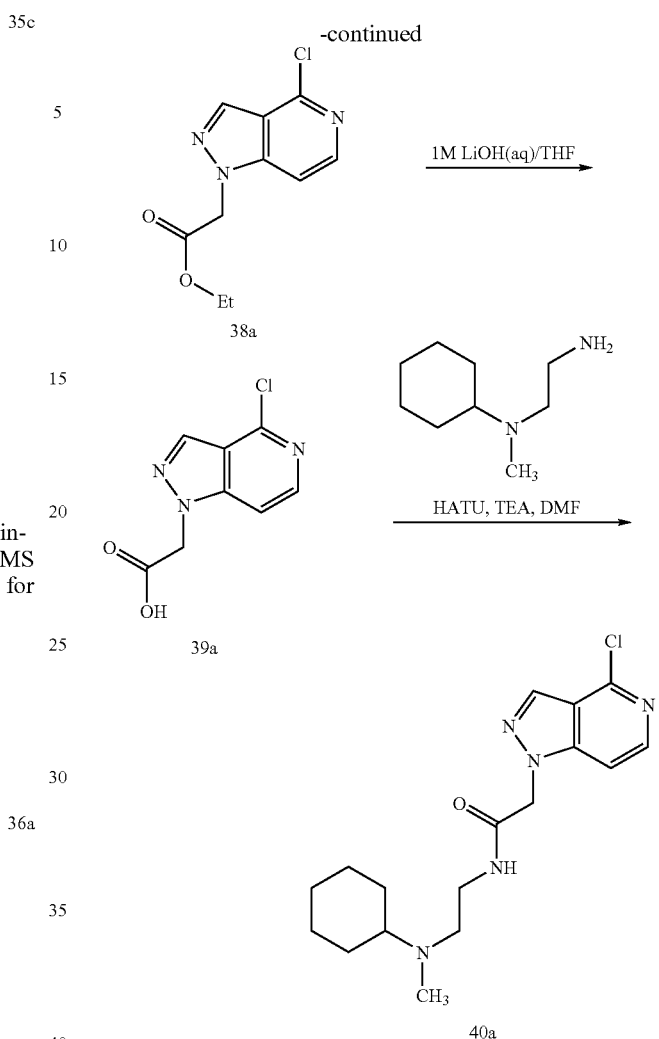

Aldehyde 37a (500 mg, 1.87 mmol) was dissolved in EtOH (3 mL) and Hydrazino-acetic acid ethyl ester (290 mg, 1.87 mmol) was added to the reaction solution. The resultant solution was heated to reflux for 6 hours. The solvent was then removed under reduced pressure and the product was purified by column chromatography (1:5 EtOAc/hexanes) to product compound 38a. Compound 38a was converted to product 40a following they synthetic procedures as outlined in Example 17 to obtain 3.8 mg of product 40a: LC-MS (Method B, retention time=0.439 min. MS calc'd for $C_{17}H_{25}ClN_5O$ (MH$^+$): 350.2. Found 350.5.

Example 21

Preparation of N-[2-(Cyclohexyl-methyl-amino)-ethyl]-2-(5-methyl-4-oxo-4,5-dihydro-pyrazolo[4,3-c]pyridin-1-yl)-acetamide (45a)

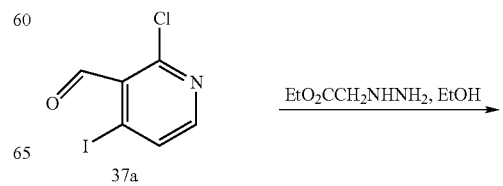

-continued

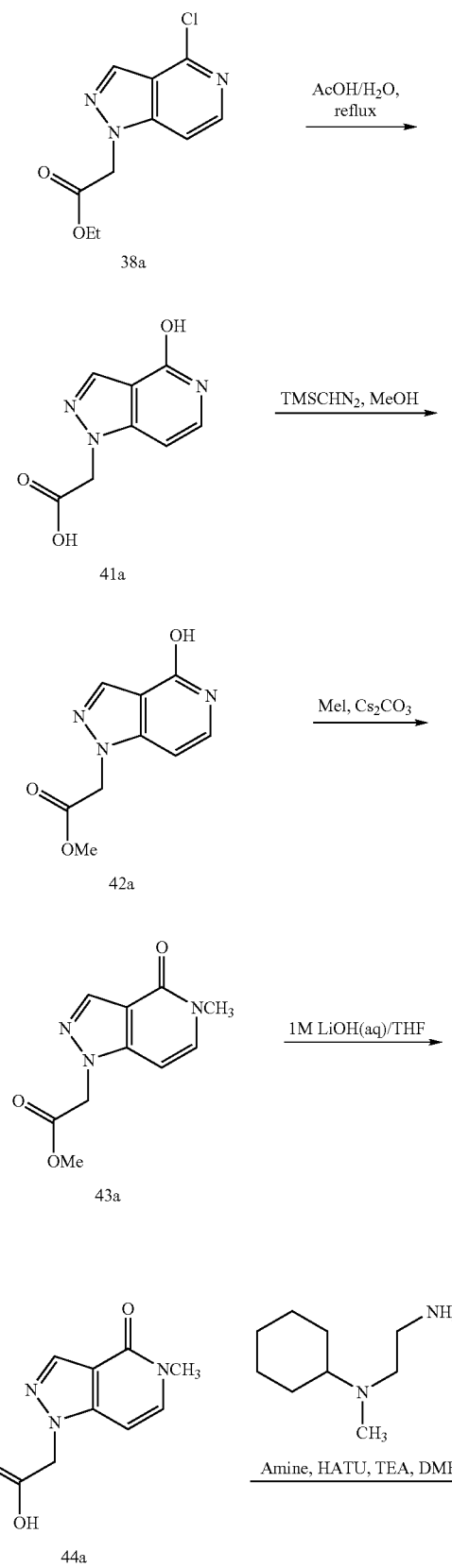

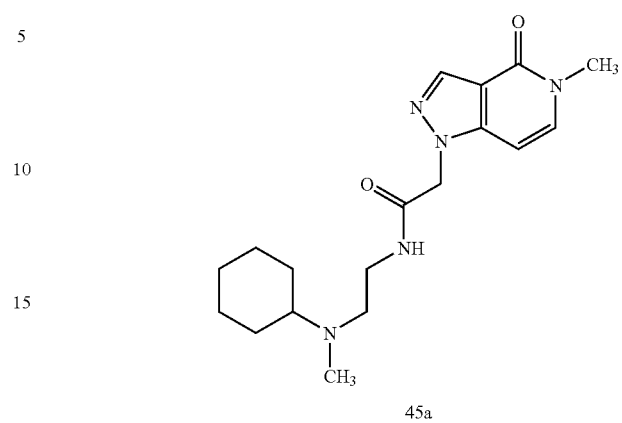

Aldehyde 37a (500 mg, 1.87 mmol) was dissolved in EtOH (3 mL) and Hydrazino-acetic acid ethyl ester (290 mg, 1.87 mmol) was added to the solution. The reaction solution was heated to reflux for 6 hours. The solvent was then removed under reduced pressure and the product 38a was purified by column chromatography (1:5 EtOAc/hexanes). The isolated product 38a (113 mg, 0.47 mmol) was dissolved in H$_2$O (463 μL) and AcOH (1.85 mL) and heated at 95° C. in a sealed vial for 4 days to produce compound 41a. The crude compound 41a was dissolved in MeOH (4 mL) and to the reaction solution was added TMSCHN$_2$ (2M in Et$_2$O) (500 μL, 1 mmol). The resultant mixture was stirred for 1 hour at room temperature. Then, the solvent was removed and to provide the crude product 42a. Compound 42a (21 mg, 0.10 mmol) was dissolved in DMF (300 μL) and to it was added MeI (7 μL, 0.1 mmol) and Cs$_2$CO$_3$ (65 mg, 0.20 mmol) and reaction mixture was stirred for 2 hours at room temperature. The reaction solution was diluted with H$_2$O and extracted with EtOAc (3×). The combined organic layer was removed under reduced pressure to provide compound 43a. Compound 43a was converted to compound 45a following the synthetic procedures described in Example 17 to give 14.8 mg of product 45a: LC-MS (Method B, retention time=0.271 min. MS calc'd for C$_{18}$H$_{28}$N$_5$O$_2$ (MH$^+$): 346.2. Found 346.5.

Example 22

Preparation of N-[2-(Cyclohexyl-methyl-amino)-ethyl]-2-(4-oxo-5-p-tolyl-4,5-dihydro-imidazo[4,5-c]pyridin-3-yl)-acetamide (50a)

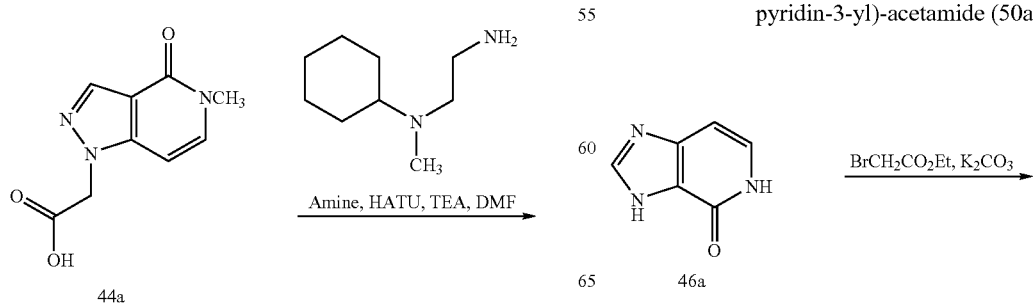

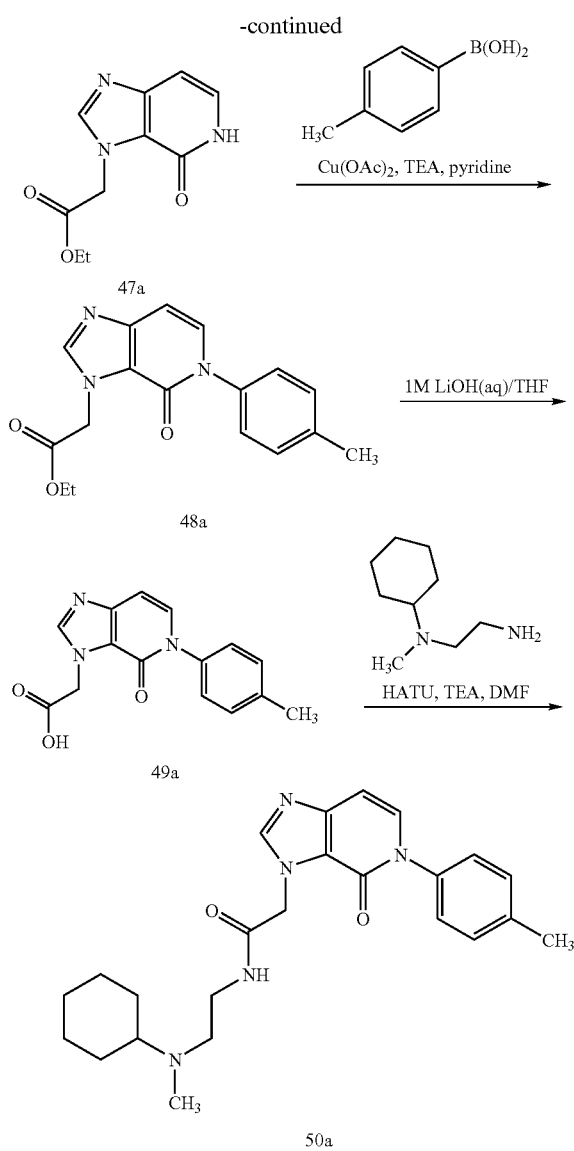

3-deazahypoxanthine 46a was prepared following a literature procedure (see, *J. Am. Chem. Soc.* 2004, 126, 9532-9533). 3-deazahypoxanthine 46a (372 mg, 2.75 mmol) was dissolved in DMF (5 mL) and to it was added Ethyl bromoacetate (340 µL, 3.03 mmol) and $K_2CO_3$ (420 mg, 3.03 mmol) and the resultant solution was heated to 65° C. for 4 hours. The reaction solution was concentrated and crude 47a purified by column chromatography (5% $MeOH/CH_2Cl_2$). The pure product 47a (100 mg, 0.45 mmol), p-tolylboronic acid (130 mg, 0.90 mmol), and $Cu(OAc)_2$ (170 mg, 0.090 mmol) were combined in $CH_2Cl_2$ (2.5 mL). To the resultant solution was added pyridine (40 µL) and TEA (70 µL) and the reaction mixture was stirred at room temperature for 3 days. The reaction solution was then filtered through Celite, washed with $CH_2Cl_2$. The organic layer was concentrated under reduced pressure and purified by column chromatography (4:1 EtOAc/hexanes) to provide compound 48a. Compound 48a was converted to compound 50a following the synthetic procedures described in Example 17 to provide 2.6 mg of compound 50a: LC-MS (Method B, retention time=2.024 min. MS calc'd for $C_{24}H_{32}N_5O_2$ ($MH^+$): 422.3. Found 422.4.

Example 23

Materials and Methods

A. Cells

1. CXCR4 Receptor Expressing Cells a) Cell Lines

CEM-Nkr, CCRF-CEM (ATCC #CCL-119), Jurkat (ATCC #TIB-152), Molt-4 (ATCC# CRL-1582), cell lines, all endogenously expressing CXCR4, were used in compound screening and subsequent assays. These cell lines were cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, and 10% FBS. Cells were grown under 5% $CO_2$/95% air, 100% humidity at 37° C. and subcultured twice weekly at 1:6 (cells were cultured at a density range of $1\times10^5$ to $2\times10^6$ cells/mL) and harvested at $1\times10^6$ cells/mL.

b) Isolated Human IL-2 Stimulated Lymphocytes

Il-2 stimulated lymphocytes were isolated from fresh human blood using density separation and centrifigation. Briefly, whole blood is incubated with equal parts 3% dextran and allowed to separate for 45 minutes. After separation, the top layer is then layered on top of 15 mls of Ficoll (15 mls of Ficoll for every 30 mls of blood suspension) and centrifuged for 30 minutes at 400×g with no brake. The pellet at the bottom of the tube is then isolated and resuspended into PharmLyse RBC Lysis Buffer (BD Biosciences, San Jose, Calif.) after which the sample is again centrifuged for 10 minutes at 400×g with brake. The remaining cell pellet is resuspended as appropriate and stimulated with PHA for 2 days, followed by culturing in the presence of human IL-2 cytokine.

B. Assays

1. Inhibition of SDF-1α Ligand Binding

Cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $4\times10^6$ cells/mL for cell lines. Binding assays were set up as follows. 0.15 mL of cells ($6\times10^5$ cells/well) was added to the assay plates containing the compounds, giving a final concentration of ~2-10 µM each compound for screening (or part of a dose response for compound $IC_{50}$ determinations). Then 0.1 mL of $^{125}$I labeled SDF-1α (obtained from Perkin Elmer Life Sciences, Boston, Mass.) diluted in assay buffer to a final concentration of ~50 pM, yielding ~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 µl; Microscint 20, Packard Instruments) was added to each well, the plates were sealed and radioactivity measured in a Topcount scintillation counter (Packard Instruments). Control wells containing either diluent only (for total counts) or excess SDF1 a (1 µg/mL, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of radiolabeled SDF-1α to the receptor by 50%. (For further descriptions of ligand binding and other functional assays, see Dairaghi, et al., *J. Biol. Chem.* 274:21569-21574 (1999), Penfold, et al., *Proc. Natl. Acad. Sci. USA.* 96:9839-9844 (1999), and Dairaghi, et al., *J. Biol. Chem.* 272:28206-28209 (1997)).

2. Calcium Mobilization

To detect the release of intracellular stores of calcium, cells (both cell lines and primary IL-2 lymphocytes) were incubated with 3 µM of INDO-1 AM dye (Molecular Probes; Eugene, Oreg.) in cell media for 45 minutes at room temperature and washed with phosphate buffered saline (PBS). After INDO-1 AM loading, the cells were resuspended in flux buffer (Hank's balanced salt solution (HBSS) and 1% FBS). Calcium mobilization was measured using a Photon Technology International spectrophotometer (Photon Technology International; N.J.) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 mL of flux buffer. The chemokine ligands may be used over a range from 1 to 100 nM. The emission ratio was plotted over time (typically 2-3 minutes). Candidate ligand blocking compounds (up to 10 µM) were added at 10 seconds, followed by chemokines at 60 seconds (i.e., TECK; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 µm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CXCR4 ligand (i.e., SDF1a, R&D Systems; Minneapolis, Minn.) are use to evaluate compound mediated inhibition of CXCR4 mediated migration. Other chemokines (i.e., TECK; R&D Systems; Minneapolis, Minn.) are used as specificity controls. The lower chamber was loaded with 29 µl of chemokine (i.e., 0.1 nM SDF1a); the top chamber contained 50,000 Jurkat cells or IL-2 lymphocytes in 20 µl. The chambers were incubated 2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

C. Identification of Inhibitors of CXCR4

1. Assay

To evaluate small organic molecules that prevent the CXCR4 from binding ligand, an assay was employed that detected radioactive ligand (i.e, SDF-1) binding to cells expressing CXCR4 on the cell surface (for example, CEM-Nkr cells). For compounds that inhibited binding, whether competitive or not, fewer radioactive counts are observed when compared to uninhibited controls.

Equal numbers of cells were added to each well in the plate. The cells were then incubated with radiolabeled CXCR4. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

2. Dose Response Curves

To ascertain a candidate compound's affinity for CXCR4 as well as confirm its ability to inhibit ligand binding, inhibitory activity was titered over a $1 \times 10^{-10}$ to $1 \times 10^{-4}$ M range of compound concentrations. In the assay, the amount of compound was varied; while cell number and ligand concentration were held constant.

3. CXCR4 Functional Assays

CXCR4 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CXCR4 inhibitory compounds were able to also block aspects of CXCR4 signaling. Candidate compounds able to inhibit ligand binding and signaling with an enhanced specificity over other chemokine and non-chemokine receptors were desired.

Calcium ion release in response to CXCR4 chemokine ligand (i.e., SDF-1α) was measured using the calcium indicator INDO-1. Molt-4 cells were loaded with INDO-1/AM and assayed for calcium release in response to CXCR4 ligand (i.e., SDF-1α) addition. To control for specificity, non-CXCR4 ligands, specifically TECK, are added, which also signals via a seven transmembrane receptor. Without compound, a pulse of fluorescent signal will be seen upon SDF1a addition. If a compound specifically inhibits CXCR4—SDF-1α signaling, then little or no signal pulse will be seen upon SDF-1α addition, but a pulse will be observed upon TECK addition. However, if a compound non-specifically inhibits signaling, then no pulse will be seen upon both SDF1a and TECK addition.

One of the primary functions of chemoattractant proteins, such a SDF-1α, is their ability to mediate the migration of chemoattractant receptor-expressing cells, such as white blood cells. To confirm that a candidate compound modulated not only CXCR4 specific binding and signaling (at least as determined by calcium mobilization assays), but also CXCR4 mediated migration, a chemotaxis assay was employed. Jurkat, Molt-4, as wells as Il-2 stimulated lymphocytes, are used as targets for chemoattraction by CXCR4 ligands (i.e., SDF-1α). Cells are place in the top compartment of a microwell chemotaxis chamber with increasing concentrations of a candidate compound, while a fixed amount of SDF1a (0.05-0.1 nM) is loaded in the lower chamber. In the absence of compound modulator, cells proceed to move chemotactically into the lower chamber in response to the chemoattractant; if a compound modulates CXCR4 function, then the majority of cells will remain in the upper chamber. To ascertain the affinity of a candidate compound for CXCR4 as well as to confirm its ability to inhibit CXCR4 mediated cell migration, inhibitory activity was titered over a $1 \times 10^{-10}$ to $1 \times 10^{-4}$ M range of compound concentrations in this chemotaxis assay. In this assay, the amount of compound was varied; while cell number and chemotractic agonist concentrations were held constant. After the chemotaxis chambers were incubated 2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.)

$$\% \text{ inhibition} = (1 - [(\text{sample } cpm) - (\text{nonspecific } cpm)] / [(\text{total } cpm) - (\text{nonspecific } cpm)]) \times 100.$$

was used to calculate $IC_{50}$ values. $IC_{50}$ values are those compound concentrations required to inhibit the number of cells responding to a CXCR4 agonist by 50%.

D. In Vitro and In Vivo Efficacy Models

The compounds of interest can be evaluated for potential efficacy in treating a CXCR4 mediated conditions by determining the efficacy of the compound in an animal model.

1. Tumor Models

To study the effects of candidate compounds on inhibiting tumor growth, a tumor implantation model is used. This method can be used to study the efficacy of candidate compounds against both murine derived tumors (syngenic) or human derived tumors (xenograft) by employing immune competent (C57B16, Balb/C) or incompetent mice (SCID, Nude), respectively. Tumor cells, grown in vitro, are washed and implanted into mice by a number of different means (sc, iv, ip). Compound dosing is employed over the course of the study and animal weights and tumor measurements are taken at various time points.

In the lung carcinoma xenograft study, A549 tumor fragments (30-40 mg) are implanted into the sub cutaneous space in nude mice. Tumors are permitted to grow until approximately 150 mg in size (between 100 and 200 mg) at which point mice are enrolled in the study and treatment begins. Mice are treated with the CXCR4 ligand competitor (25 mpk; sc administration, Q1D) or the vehicle control. Melphalan may be included as the positive control (9 mpk/dose, ip administration, Q4D×3). Tumors are measured twice weekly with a caliper in two dimensions and converted to tumor mass using the formula for a prolate ellipsoid ($a \times b^2/2$), where a is the longer dimension and b is the shorter dimension, and assuming unit density (1 $mm^3$=1 mg). Body weights are also measured twice weekly to assess any adverse effects of compound dosing. Antitumor activity is assessed by the delay in tumor growth of the treated group in comparison to the vehicle-treated control group.

The mice receiving the competitor or positive control may be expected to exhibit reduced tumor load compared to the vehicle treated group.

a) Rabbit Model of Destructive Joint Inflammation

To study the effects of compounds of interest on inhibiting the inflammatory response of rabbits to an intra-articular injection of the bacterial membrane component lipopolysaccharide (LPS), a rabbit model of destructive joint inflammation may be used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J. Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of a compound of interest (dose 1=50 µM or dose 2=100 µM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1—minimal, 2—mild, 3—moderate, 4—moderate-marked.

b) Evaluation of a Compound of Interest in a Rat Model of Collagen Induced Arthritis A 17 day developing type II collagen arthritis study is conducted to evaluate the effects of a compound of interest on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A compound of interest is dosed daily in a sub-cutaneous manner from day 0 till day 17 at a efficacious dose. Caliper measurements of the ankle joint diameter is taken, and reducing joint swelling was taken as a measure of efficacy.

c) Evaluation of a Compound of Interest in a Stem Cell Mobilization Model

To assess the ability of compounds to mobilize stem and progenitors cells into the peripheral blood, mice are dosed (sc) with test compound or vehicle and blood is harvested at various times over the course of 24 hours via eyebleed. Cell counts are normalized and an equivalent number of cells are plated in MethoCult for 7-10 days to allow stem/progenitor cells to grow into colonies. Final counts of colony forming units are recorded from test compound dosed animals and compared with vehicle dosed animals. Elevation of colony forming units in compound dosed animals confirmed mobilization. Detailed protocols can be found in for instance Broxmeyer et al. J Exp Med. 2005 Apr. 18; 201(8):1307-18.

d) Evaluation of a Compound of Interest in Anti-HIV Infectivity Assay

To test the ability of compounds to inhibit HIV entry into cells, stable cell lines expressing CXCR4 and CD4 are plated and infected with an HIV virus expressing a marker, for instance the lacZ gene, in the presence or absence of compound. Resulting infection correlates with lacZ activity on the beta-galactosidase substrate which is read colormetrically. A decrease in lacZ expression in cells indicates inhibition of HIV infection by compound.

Example 24

To demonstrate that the compounds in the present invention are useful modulators for chemokine binding to CCX-CKR2, the compounds were screened in vitro to determine their ability to displace SDF-1 from the CCXCKR2 receptor at multiple concentrations. The compounds were combined with mammary gland cells expressing the CCXCKR2 receptor in the presence of the $^{125}$I-labeled chemokine as detailed in *Determination of $IC_{50}$ values, Reagents and Cells* (see below). The ability of the compounds to displace the labeled chemokine from the CCXCKR2 receptor sites at multiple concentrations was then determined with the screening process.

Determination of $IC_{50}$ Values for CCXCKR2 (CXCR7):

Reagents and Cells. $^{125}$I-labeled SDF-1 was purchased from Perkin-Elmer Life Sciences, Inc. (Boston, Mass.). The MCF-7 (adenocarcinoma; mammary gland) cell line was obtained from the American Type Culture Collection (Manassas, Va.) or and was cultured in DMEM (Mediatech, Herndon, Va.) supplemented with 10% fetal bovine serum (FBS) (HyClone Logan, Utah) and bovine insulin (0.01 mg/mL) (Sigma, St. Louis, Mo.) at 37° C. in a humidified incubator at a 5% $CO_2$/air mixture. CCXCKR2 transfected MDA-MB-435S were produced as described below. MDA-MB-435S human breast cancer line, was purchased from ATCC, and cultured in DMEM/10% FBS medium. The complete coding sequence of the gene encoding CCXCKR2 (a.k.a. CXCR7, hRDC1), was isolated from MCF-7 cells using μMACs mRNA isolation kit (Miltenyi Biotec, Auburn, Calif.). DNA contamination was removed by DNase digestion via RNeasy columns (Qiagen, Inc., Valencia, Calif.) and cDNA was generated using GeneAmp RNA PCR Core Kit (Applied Biosystems, Foster City, Calif.). PCR of cDNA samples was performed using Taq PCR Master Mix kit (Qiagen, Inc.) and hRDC1 primers harboring 5' and 3' NotI sites (hRDC1F 5' GAATGCGGCCGCTATGGATCTGCATCTCTTCGACT-3' (SEQ ID NO:11, hRDC1R 5'-GAATGCGGCCGCT-CATTTGGTGCTCTGCTCCAAG-3') Not I digested PCR product was ligated into Not I digested pcDNA3.1 (+)(Invitrogen, Carlsbad, Calif.) and screened for orientation and sequence confirmed. Plasmid DNA was then isolated from overnight bacterial cultures by Maxiprep (Qiagen, Inc.). Plasmid DNA (10 μg) was added to MDA-MB-435s cells and cells were electroporated (0.22 kV, 960 uF) via Gene Pulser (Biorad laboratories, Hercules, Calif.). 48 hr post-electroporation, cells were transferred to selection medium (1000 ug/ml G418).

Binding Analysis. Target compounds were tested to determine their ability to bind with CCXCKR2 sites on MCF-7 and/or MDA-MB-435S cells. Efficiency-maximized radioligand binding using filtration protocols as described in Dairaghi D J, et al., *HHV8-encoded vMIP-I selectively engages chemokine receptor CCR5. Agonist and antagonist profiles of viral chemokines.*, J. Biol. Chem. 1999 Jul. 30; 274(31): 21569-74 and Gosling J, et al., *Cutting edge: identification of a novel chemokine receptor that binds dendritic cell-and T cell-active chemokines including ELC, SLC, and TECK.*, J. Immunol. 2000 Mar. 15; 164(6):2851-6 was used.

In these assays, MCF-7 and/or MDA-MB-435S cells were interrogated with the target compounds and the ability of these compounds to displace $^{125}I$ radiolabeled SDF-1 was assessed using the protocol described in *Dairaghi and Gosling*. The target compounds were added to the plate to the indicated concentration and were then incubated with cells followed by the addition of radiolabeled chemokine ($^{125}I$ SDF-1) for 3 hr at 4° C. in the following binding medium (25 mM HEPES, 140 mM NaCl, 1 mM $CaCl_2$, 5 mM $MgCl_2$ and 0.2% bovine serum albumin, adjusted to pH 7.1). All assays were then incubated for 3 hrs at 4° C. with gentle agitation. Following incubation in all binding assays, reactions were aspirated onto PEI-treated GF/B glass filters (Packard) using a cell harvester (Packard) and washed twice (25 mM HEPES, 500 mM NaCl, 1 mM $CaCl_2$, 5 mM $MgCl_2$, adjusted to pH 7.1). Scintillant (MicroScint 10, Packard) was added to the wells, and the filters were counted in a Packard Topcount scintillation counter. Data were analyzed and plotted using Prism (GraphPad Prism version 3.0a for Macintosh, GraphPad Software, www.graphpad.com).

Example 25

In the table below, structures and activity are provided for representative compounds described herein. Activity is provided as follows for either the chemotaxis assay or binding assays as described above for either CXCR4 or CXCR7. If only one activity is listed, the activity is for CXCR4. If two activities are listed, the second value pertains to CXCR7: +, $IC_{50}$>10 uM; ++, 1 uM<$IC_{50}$<10 uM; +++, and +++, $IC_{50}$<1000 nM.

TABLE 2

| No | Structure | CXCR4/CXCR7 |
|---|---|---|
| 1 | 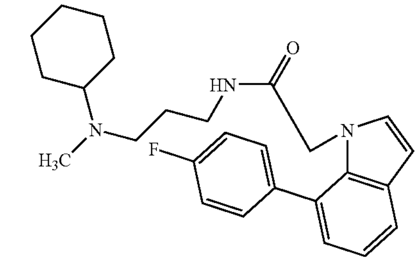 | +++ |
| 2 | 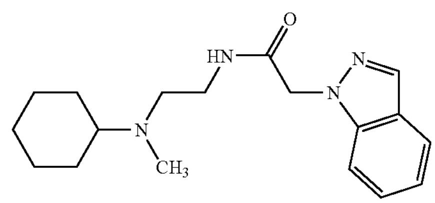 | + |
| 3 | 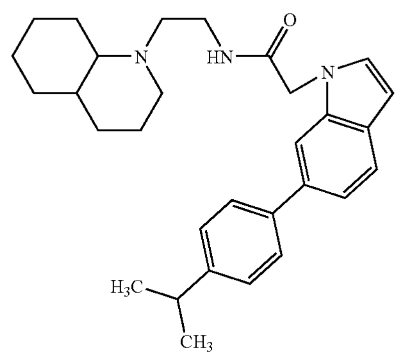 | +++ |
| 4 | 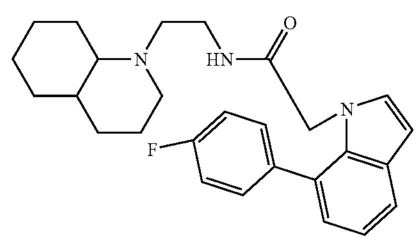 | +++ |
| 5 | 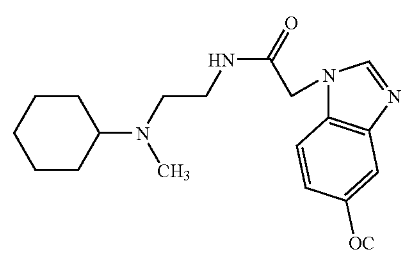 | +++ |

TABLE 2-continued
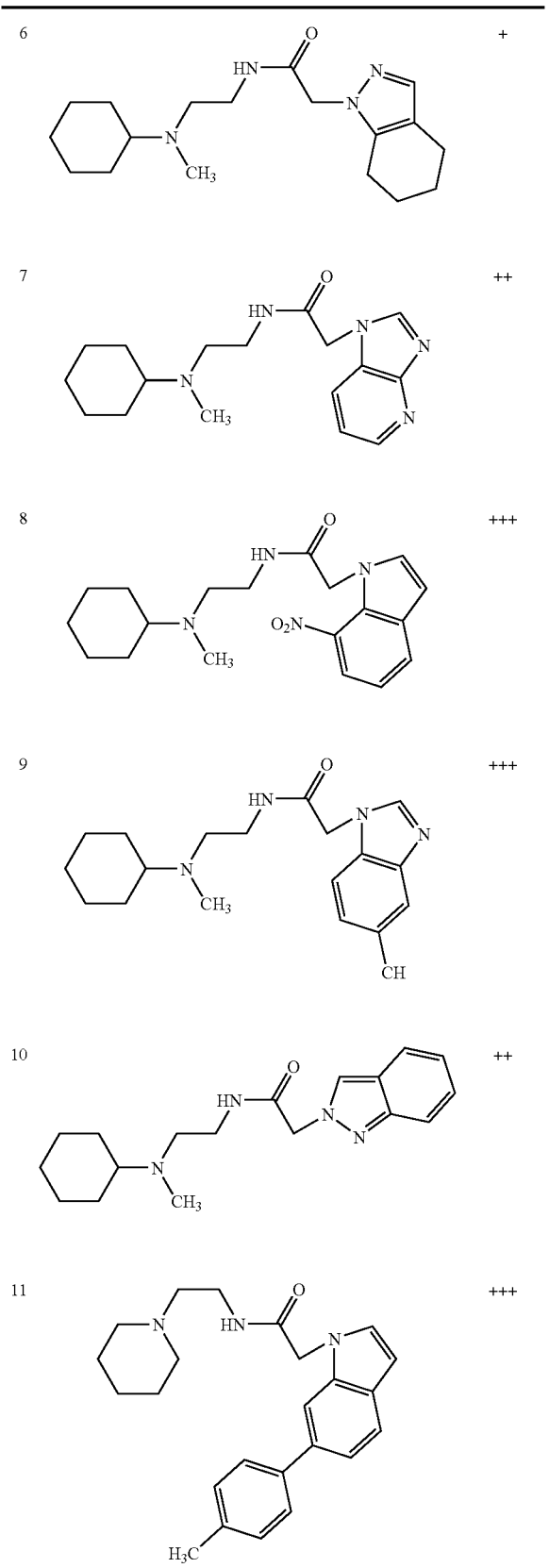
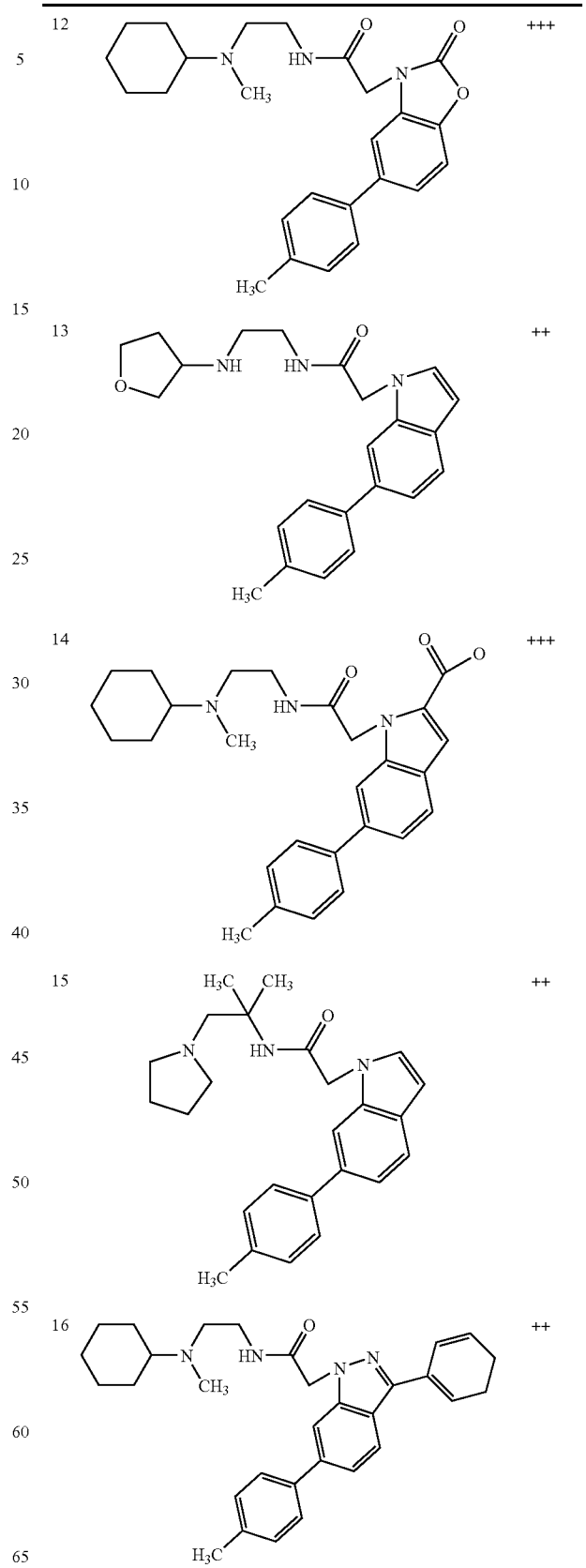

TABLE 2-continued

| # | Structure | Activity |
|---|---|---|
| 17 | (cyclohexyl-N(CH3)-CH2CH2-NH-C(O)-CH2-indole with 4-OCH3 and 6-(4-methylphenyl)) | +++ |
| 18 | (cyclohexyl-N(CH3)-CH2CH2-NH-C(O)-CH2-benzimidazole with 4,5-diF) | +++ |
| 19 | (cyclohexyl-N(CH3)-CH2CH2-NH-C(O)-CH2-pyrano-imidazole) | + |
| 20 | (cyclohexyl-N(CH3)-CH2CH2-NH-C(O)-CH2-indol-3-yl) | ++ |
| 21 | (cyclohexyl-N(CH3)-CH2CH2-NH-C(O)-CH2-N-(3-chloroindazole)) | ++ |
| 22 | (6-phenyl-indol-1-yl-CH2-C(O)-NH-CH2CH2-N(CH3)-cyclohexyl) | +++ |
| 23 | (6-(4-fluorophenyl)-indol-1-yl-CH2-C(O)-NH-CH2CH2-N(CH3)-cyclohexyl) | +++/+++ |
| 24 | (6-(4-methylphenyl)-indol-1-yl-CH2-C(O)-NH-CH2CH2-N(CH3)-cyclohexyl) | +++/++ |
| 25 | (6-(4-trifluoromethylphenyl)-indol-1-yl-CH2-C(O)-NH-CH2CH2-N(CH3)-cyclohexyl) | +++ |
| 26 | (6-(4-methoxyphenyl)-indol-1-yl-CH2-C(O)-NH-CH2CH2-N(CH3)-cyclohexyl) | +++/++ |

TABLE 2-continued
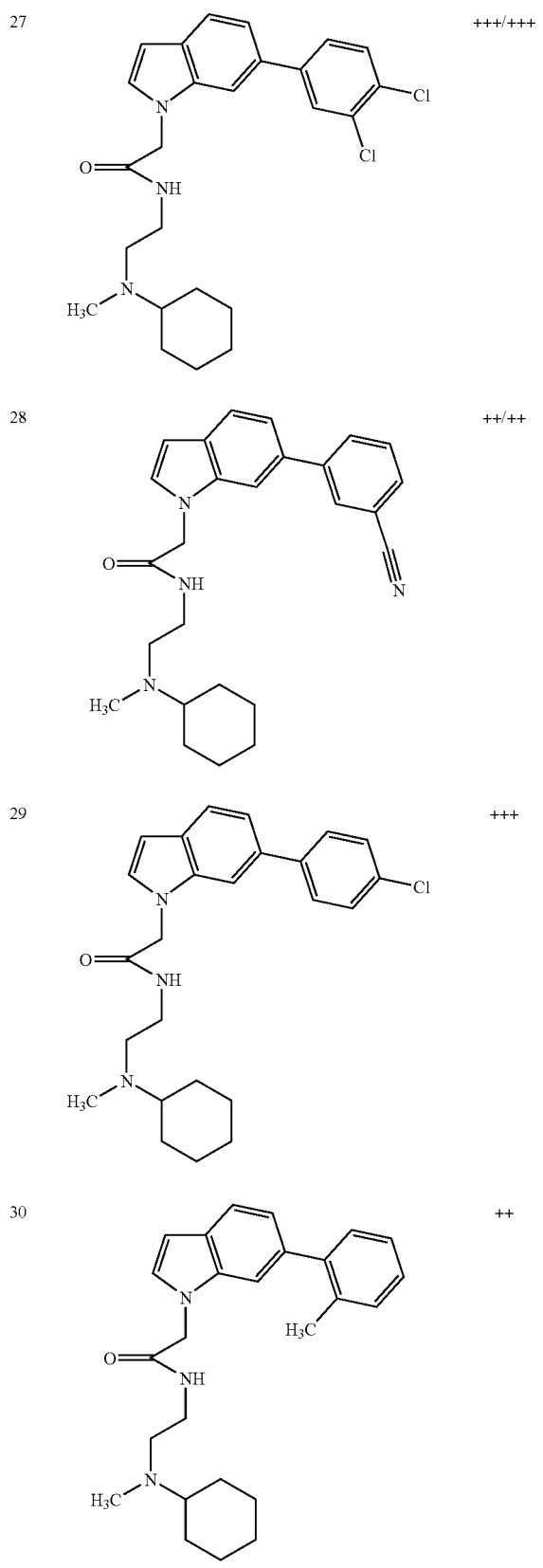
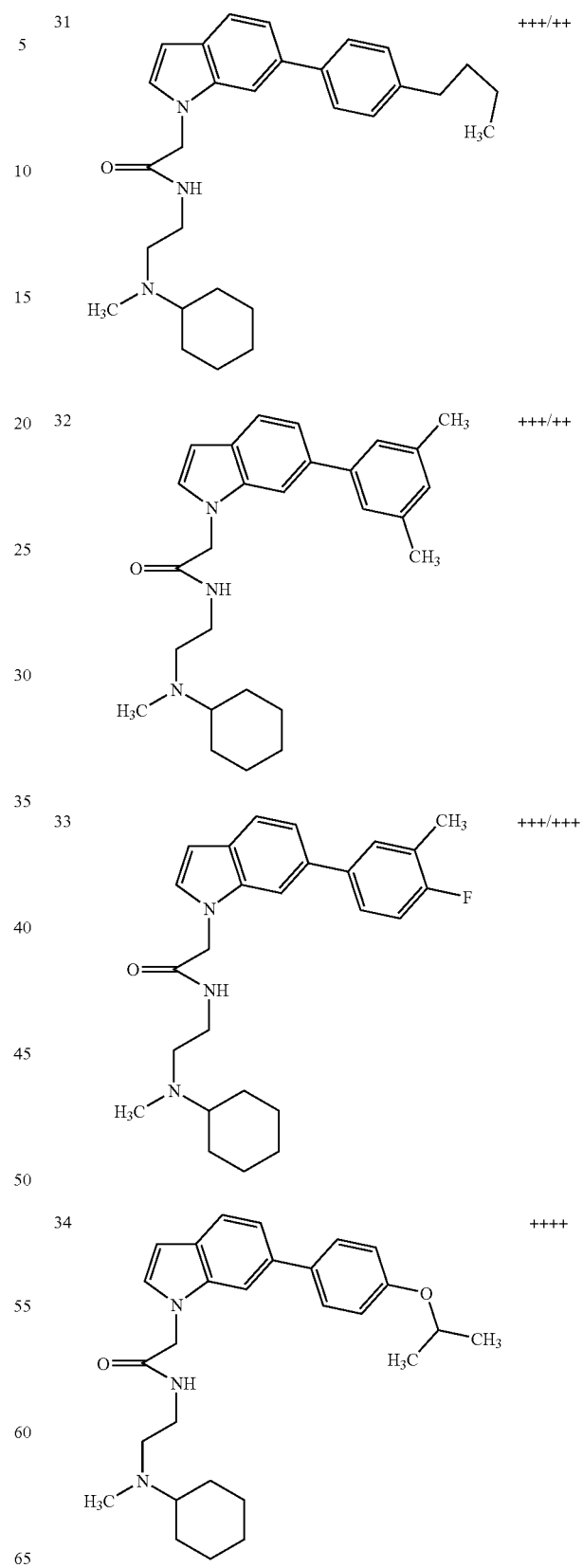

TABLE 2-continued

| No | Structure | Activity |
|----|-----------|----------|
| 35 | | +++/++ |
| 36 | | +++ |
| 37 | | +++ |
| 38 | | +++ |
| 39 | | +++ |
| 40 | | +++ |
| 41 | | +++ |

TABLE 2-continued
| 42 | 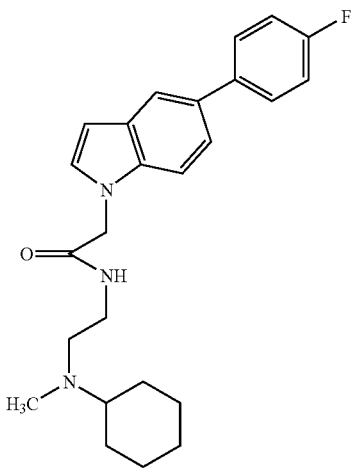 | +++ |
| 43 | 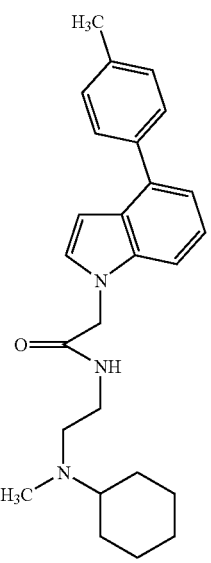 | +++ |
| 44 | 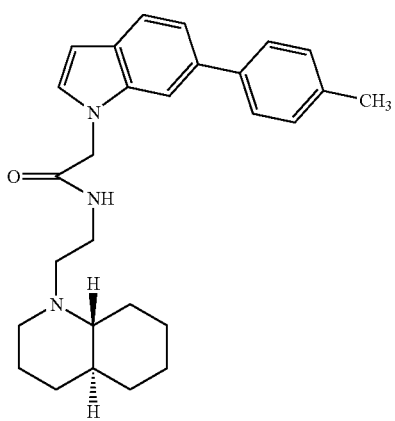 | +++ |
TABLE 2-continued
| 45 | 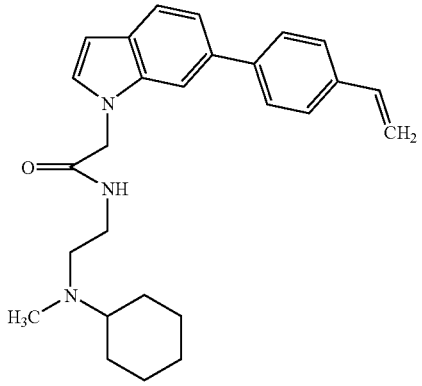 | +++ |
| 46 | 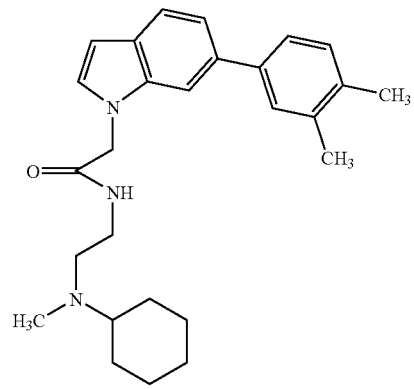 | +++ |
| 47 | 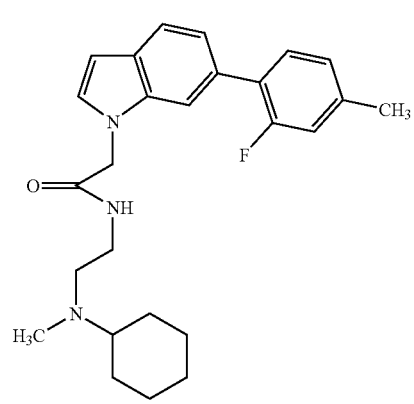 | +++ |
| 48 | 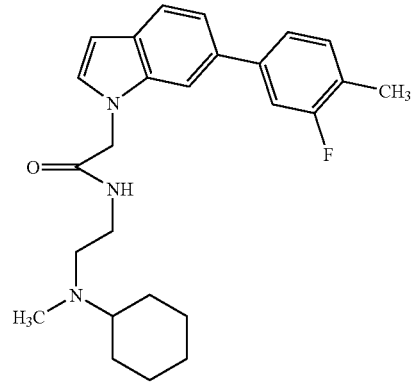 | +++ |

TABLE 2-continued
| 49 | 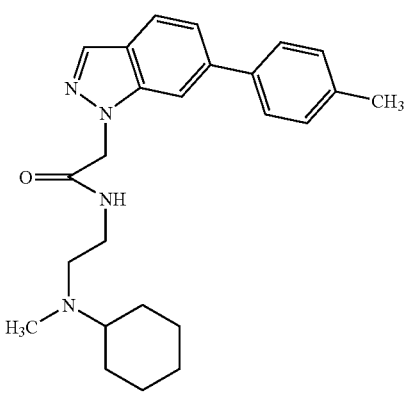 | +++ |
| 50 | 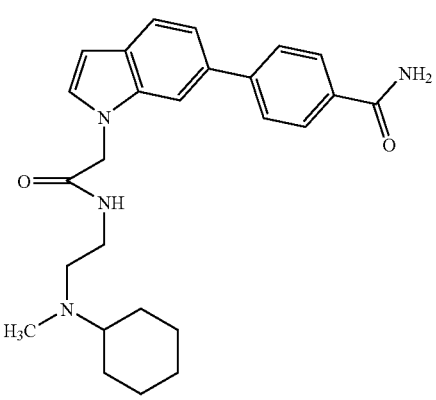 | +++ |
| 51 | 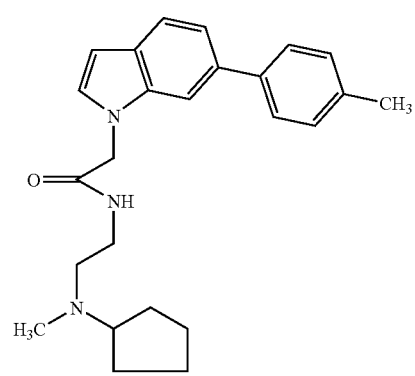 | +++ |
| 52 | 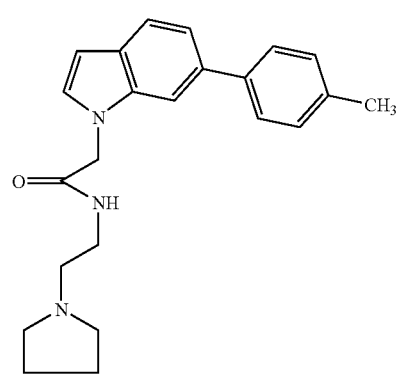 | +++ |
TABLE 2-continued
| 53 | 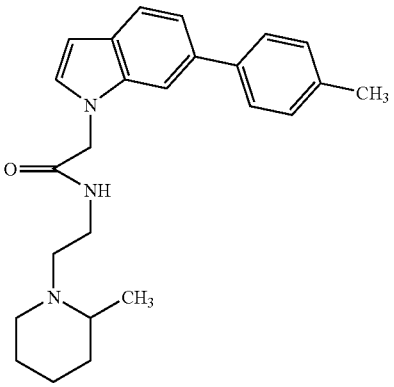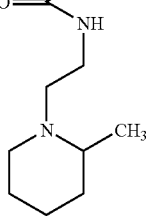 | +++ |
| 54 | 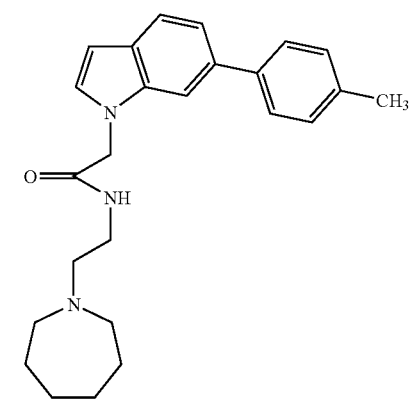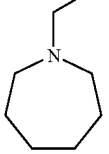 | +++ |
| 55 | 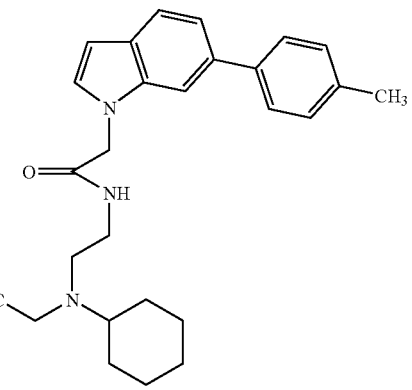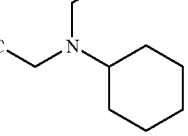 | +++ |
| 56 | 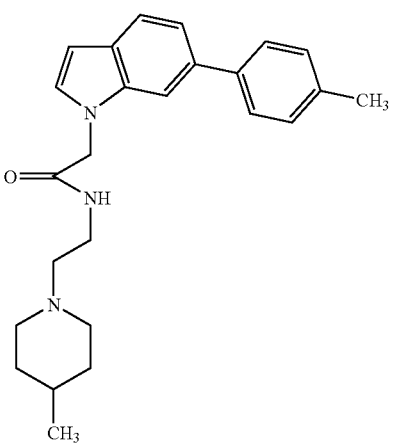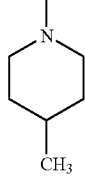 | +++ |

TABLE 2-continued
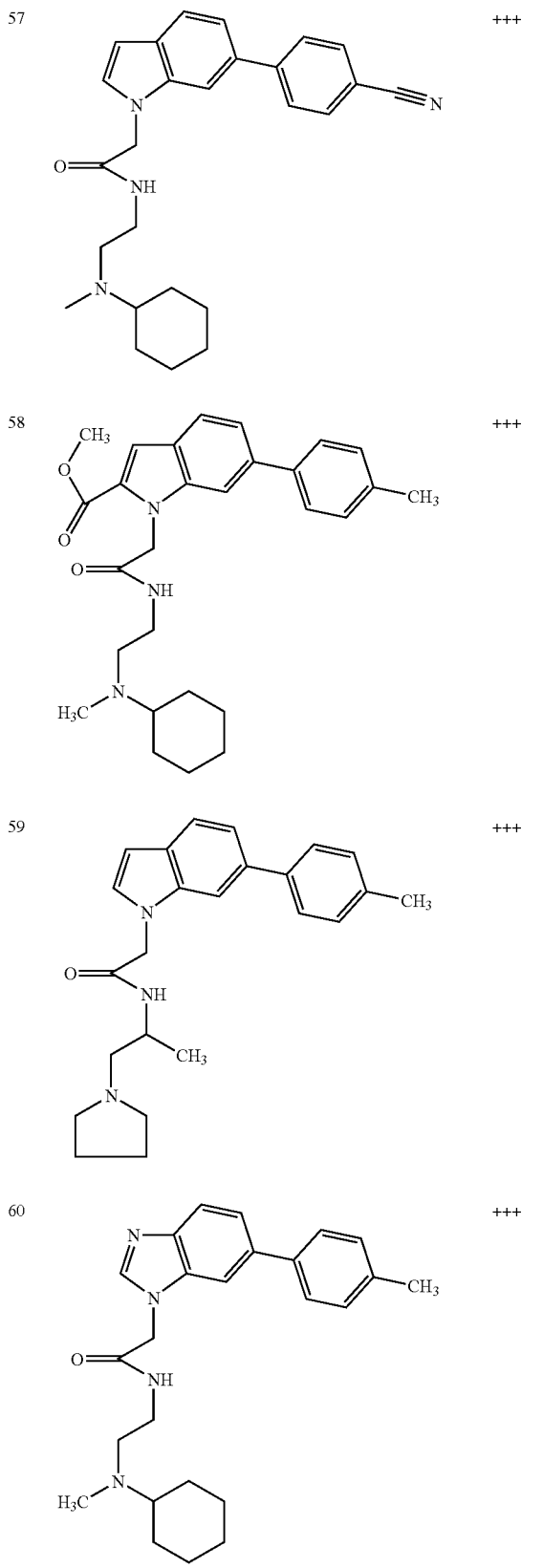
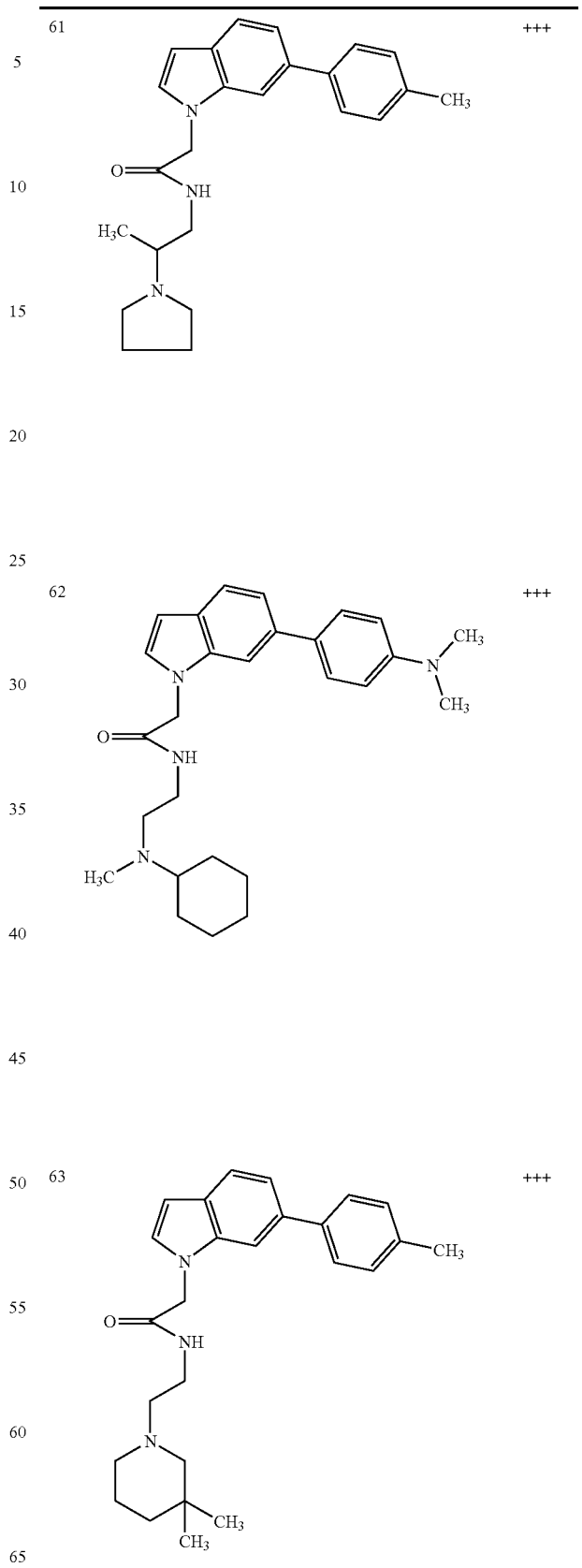

TABLE 2-continued

| | | |
|---|---|---|
| 64 | 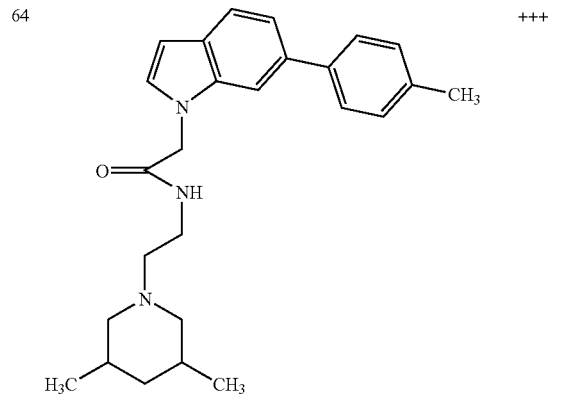 | +++ |
| 65 | 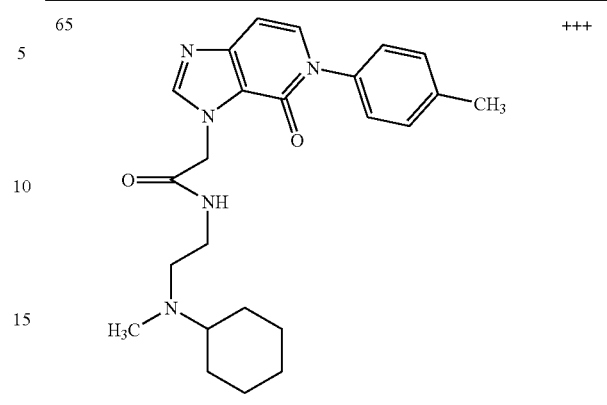 | +++ |

What is claimed is:

1. A compound having formula I:

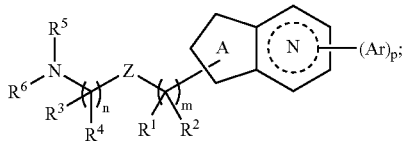

or a pharmaceutically acceptable salt thereof, wherein $R^1$, $R^2$, $R^3$ and $R^4$ at each occurrence are each independently selected from the group consisting of hydrogen, halogen, $C_{1-8}$ alkyl, $C_{1-8}$ haloalkyl, $C_{1-8}$ heteroalkyl, $C_{2-8}$ alkenyl and $C_{2-8}$ alkynyl; wherein the aliphatic portions of $R^1$—$R^4$ are each independently substituted with from 0-3 substituents selected from the group consisting of —OH, —OR''', —OC(O)NHR''', —OC(O)N(R''')$_2$, —SH, —SR''', —S(O)R''', —S(O)$_2$R''', —SO$_2$NH$_2$, —S(O)$_2$NHR''', —S(O)$_2$N(R''')$_2$, —NHS(O)$_2$R''', —NR'''S(O)$_2$R''', —C(O)NH$_2$, —C(O)NHR''', —C(O)N(R''')$_2$, —C(O)R''', —NHC(O)R''', —NR'''C(O)R''', —NHC(O)NH$_2$, —NR'''C(O)NH$_2$, —NR'''C(O)NHR''', —NHC(O)NHR''', —NR'''C(O)N(R''')$_2$, —NHC(O)N(R''')$_2$, —CO$_2$H, —CO$_2$R''', —NHCO$_2$R''', —NR'''CO$_2$R''', —CN, —NO$_2$, —NH$_2$, —NHR''', —N(R''')$_2$, —NR'''S(O)NH$_2$ and —NR'''S(O)$_2$NHR'''; wherein R''' at each occurrence is independently an unsubstituted $C_{1-6}$ alkyl;

$R^5$ and $R^6$ are each independently selected from the group consisting of hydrogen, $C_{1-8}$ alkyl, $C_{1-8}$ haloalkyl, $C_{2-8}$ alkenyl, $C_{2-8}$ alkynyl, $C_{3-10}$ cycloalkyl, $C_{3-10}$ heterocycloalkyl, $C_{1-8}$ acyl, $C_{1-8}$ alkyl-S(O)$_2$—, aryl, heteroaryl, aryl-$C_{1-6}$ alkyl and aryl-$C_{1-6}$ heteroalkyl, or optionally $R^5$ and $R^6$ are combined to form a 5- to 10-membered ring system having from 1-3 heteroatoms selected from the group consisting of N, O and S; wherein the aliphatic portions of $R^5$ and $R^6$ are further substituted with 0-3 substituents selected from the group consisting of —OH, —OR'', —OC(O)NHR'', —OC(O)N(R'')$_2$, —SH, —SR'', —S(O)R'', —S(O)$_2$R'', —SO$_2$NH$_2$, —S(O)$_2$NHR'', —S(O)$_2$N(R'')$_2$, —NHS(O)$_2$R'', —NR''S(O)$_2$R'', —C(O)NH$_2$, —C(O)NHR'', —C(O)N(R'')$_2$, —C(O)R'', —NHC(O)R'', —NR''C(O)R'', —NHC(O)NH$_2$, —NR''C(O)NH$_2$, —NR''C(O)NHR'', —NHC(O)NHR'', —NR''C(O)N(R'')$_2$, —NHC(O)N(R'')$_2$, —CO$_2$H, —CO$_2$R'', —NHCO$_2$R'', —NR''CO$_2$R'', —CN, —NO$_2$, —NH$_2$, —NHR'', —N(R'')$_2$, —NR''S(O)NH$_2$ and —NR''S(O)$_2$NHR'', wherein R'' at each occurrence is independently an unsubstituted $C_{1-6}$ alkyl;

Z is a linking group selected from the group consisting of —CONR$^b$— and —NR$^b$C(O) wherein R$^b$ at each occurrence is independently selected from the group consisting of hydrogen, $C_{1-8}$ acyl, $C_{1-8}$ alkyl-S(O)$_2$—, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl; wherein the aliphatic portions of Z are substituted with from 0-3 substituents independently selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein R$^o$ at each occurrence is independently an unsubstituted $C_{1-6}$ alkyl;

the subscripts m and n are each independently an integer from 1 to 6;

wherein $R^1$ and $R^2$, $R^3$ and $R^4$ are optionally are combined to form a 5-10 membered ring having from 0-2 heteroatoms selected from the group consisting of N, O and S; and when the subscript m or n is an integer from 2-6, the $R^1$ and $R^2$, or $R^3$ and $R^4$ substituents that are combined can be attached to the same or different carbon atoms;

the ring represented by

is a pyrrole ring substituted with 0-2 substitutents selected from the group consisting of -L$^1$R$^8$ and —R$^8$, wherein R$^8$ at each occurrence is selected from the group consisting of hydrogen, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkyl-$C_{1-6}$ alkyl, aryl-$C_{1-6}$ alkyl, heterocycloalkyl-$C_{1-6}$ alkyl, aryl-$C_{1-6}$ heteroalkyl, aryl, heteroaryl and halogen; and wherein L$^1$ is a linking group selected from the group consisting of —C(O)—, —C(=NOR$^e$)—, —C(=NR$^g$)—, —CO$_2$—, —CONR$^e$—, —OC(O)NR$^e$—, —NR$^e$C(O)—, —NR$^e$C(O)$_2$—, —NR$^e$C(O)NR$^f$—, —NHC(=NH)NH—, —NR$^g$C(=NH)NH—, —NHC(=NR$^g$)NH—, —NHC(=NH)—NR$^g$—, —S(O)—, —S(O)$_2$—, —NR$^e$S(O)$_2$—, —S(O)$_2$NR$^e$— and —NR$^e$S(O)$_2$NR$^f$—, wherein R$^e$ and R$^f$ at each occurrence are independently selected from the group consisting of hydrogen, $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl; R$^g$ is independently selected from the group consisting of $C_{1-8}$ alkyl, $C_{1-8}$ haloalkyl, $C_{2-8}$ heteroalkyl, $C_{3-6}$ cycloalkyl, $C_{2-8}$ alkenyl, $C_{2-8}$ alkynyl, aryl, heteroaryl and aryl-$C_{1-4}$ alkyl; wherein the aliphatic portions of R$^8$ are substituted with from 0-3 substituents selected from the group consisting of halogen, —OH, —OR$^q$, —OC(O)NHR$^q$, —OC(O)N(R$^q$)$_2$, —SH, —SR$^q$, —S(O)R$^q$, —S(O)$_2$R$^q$, —SO$_2$NH$_2$, —S(O)$_2$NHR$^q$, —S(O)$_2$N(R$^q$)$_2$, —NHS(O)$_2$R$^q$, —NR$^q$S(O)$_2$R$^q$, —C(O)NH$_2$, —C(O)NHR$^q$, —C(O)N(R$^q$)$_2$, —C(O)R$^q$, —NHC(O)R$^q$, —NR$^q$C(O)R$^q$, —NHC(O)NH$_2$, —NR$^q$C(O)NH$_2$, —NR$^1$C(O)NHR$^q$, —NHC(O)NHR$^q$, —NR$^q$C(O)N(R$^q$)$_2$, —NHC(O)N(R$^q$)$_2$, —CO$_2$H, —CO$_2$R$^q$, —NHCO$_2$R$^q$, —NR$^q$CO$_2$R$^q$, —CN, —NO$_2$, —NH$_2$, —NHR$^q$, —N(R$^q$)$_2$, —NR$^q$S(O)NH$_2$ and —NR$^q$S(O)$_2$NHR$^q$, wherein each R$^q$ is independently an unsubstituted $C_{1-6}$ alkyl;

the ring represented by

is a benzene ring having from 0-4 $R^7$ substituents; wherein $R^7$ at each occurrence is independently selected from the group consisting of halogen, cyano, heteroaryl, $-R^j$, $-NO_2$, $-CO_2R^h$, $-C(O)NR^hR^i$, $-C(O)R^h$, $-S(O)R^j$, $-S(O)_2R^j$, $-OC(O)R^h$, $-NR^h-C(O)NR^hR^i$, $-NH-C(NH_2)=NH$, $-NR^jC(NH_2)=NH$, $-NH-C(NH_2)=NR^j$, $-NH-C(NHR^j)=NH$, $-NR^hS(O)_2R^j$, $-NR^hS(O)_2R^j$, $-NR^hS(O)_2NR^hR^i$, $-N_3$, $-C(NOR^h)R^i$, $-C(NR^hV)=NV$, $-N(V)C(R^h)=NV$, $-X^iC(NOR^h)R^i$, $-X^iC(NR^hV)=NV$, $-X^iN(V)C(R^h)=NV$, $-X^iNR^hR^i$, $-X^iSR^h$, $-X^iCN$, $-X^iNO_2$, $-X^iCO_2R^h$, $-X^iCONR^hR^i$, $-X^iC(O)R^h$, $-X^iOC(O)NR^hR^i$, $-X^iNR^iC(O)R^h$, $-X^iNR^iC(O)_2R^j$, $-X^iNR^hC(O)NR^iR^j$, $-X^iNH-C(NH_2)=NH$, $-X^i-NR^jC(NH_2)=NH$, $-X^iNH-C(NH_2)=NR^j$, $-X^iNH-C(NHR^j)=NH$, $-X^iS(O)R^j$, $-X^iS(O)_2R^j$, $-X^iNR^hS(O)_2R^j$, $-X^iS(O)_2NR^hR^i$, $-X^iN_3$, $-NR^hR^i$, $-OR^h$, $-SR^h$, $-NR^iC(O)R^h$, $-NR^iC(O)_2R^j$, $-S(O)_2NR^hR^i$, $-X^iOR^h$, $-O-X^iOR^h$, $-O-X^i-NR^hR^i$ and $-NR^i-X^iCO_2R^h$, and optionally any two $R^7$ substituents located on adjacent atoms can be combined to form a 5- to 7-membered ring optionally having from 1-3 heteroatoms selected from the group consisting of N, O and S; wherein $X^i$ is $C_{1-4}$ alkylene, $C_{1-4}$ heteroalkylene, $C_{2-4}$ alkenylene or $C_{2-4}$ alkynylene; each $R^h$ and $R^i$ is independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-4}$ alkyl, and optionally, $R^h$ and $R^i$ when attached to the same nitrogen atom can be combined to form a five- or six-membered ring having from 0 to 2 additional heteroatoms as ring members; -each $R^j$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl; and each of $X^i$, $R^h$, $R^i$ and $R^j$ is further substituted with from 0-3 members selected from the group consisting of halogen, $-OH$, $-OR^r$, $-OC(O)NHR^r$, $-OC(O)N(R^r)_2$, $-SH$, $-SR^r$, $-S(O)R^r$, $-S(O)_2R^r$, $-SO_2NH_2$, $-S(O)_2NHR^r$, $-S(O)_2N(R^r)_2$, $-NHS(O)_2R^r$, $-NR^rS(O)_2R^r$, $-C(O)NH_2$, $-C(O)NHR^r$, $-C(O)N(R^r)_2$, $-C(O)R^r$, $-NHC(O)R^r$, $-NR^rC(O)R^r$, $-NHC(O)NH_2$, $-NR^rC(O)NH_2$, $-NR^RC(O)NHR^r$, $-NHC(O)NHR^r$, $-NR^rC(O)N(R^r)_2$, $-NHC(O)N(R^r)_2$, $-CO_2H$, $-CO_2R^r$, $-NHCO_2R^r$, $-NR^rCO_2R^r$, $-CN$, $-NO_2$, $-NH_2$, $-NHR^r$, $-N(R^r)_2$, $-NR^rS(O)NH_2$ and $-NR^rS(O)_2NHR^r$, wherein each $R^r$ is independently an unsubstituted $C_{1-6}$ alkyl, and wherein V is independently selected from the group consisting of $-R^j$, $-CN$, $-CO_2R^h$ and $-NO_2$;

Ar is a 5-10 membered aryl or a heteroaryl ring system having from 1-3 nitrogen atoms, said ring having from 1-5 $R^9$ substituents; wherein $R^9$ at each occurrence is independently selected from the group consisting of hydroxy, halogen, cyano, heteroaryl, $-R^m$, $-NO_2$, $-CO_2R^k$, $-C(O)NR^kR^L$, $-C(O)R^k$, $-S(O)R^m$, $-S(O)_2R^m$, $-OC(O)R^k$, $-NR^k-C(O)NR^kR^L$, $-NH-C(NH_2)=NH$, $-NR^mC(NH_2)=NH$, $-NH-C(NH_2)=NR^m$, $-NH-C(NHR^m)=NH$, $-NR^kS(O)_2R^m$, $-NR^kS(O)_2R^m$, $-NR^kS(O)_2NR^kR^L$, $-N_3$, $-C(NOR^k)R^L$, $-C(NR^kU)=NU$, $-N(U)C(R^k)=NU$, $-X^2C(NOR^k)R^L$, $-X^2C(NR^kU)=NU$, $-X^2N(U)C(R^k)=NU$, $-X^2NR^kR^L$, $-X^2SR^k$, $-X^2CN$, $-X^2NO_2$, $-X^2CO_2R^k$, $-X^2CONR^kR^L$, $-X^2C(O)R^k$, $-X^2OC(O)NR^kR^L$, $-X^2NR^LC(O)R^k$, $-X^2NR^LC(O)_2R^m$, $-X^2NR^kC(O)NR^LR^m$, $-X^2NH-C(NH_2)=NH$, $-X^2NR^mC(NH_2)=NH$, $-X^2NH-C(NH_2)=NR^m$, $-X^2NH-C(NHR^m)=NH$, $-X^2S(O)R^m$, $-X^2S(O)_2R^m$, $-X^2NR^kS(O)_2R^m$, $-X^2S(O)_2NR^kR^L$, $-X^2N_3$, $-NR^kR^L$, $-OR^m$, $-SR^k$, $-NR^LC(O)R^k$, $-NR^LC(O)_2R^m$, $-S(O)_2NR^kR^L$, $-X^2OR^k$, $-O-X^2OR^k$, $-O-X^2NR^kR^L$ and $-NR^L-X^2CO_2R^k$; and optionally any two $R^9$ substituents located on adjacent atoms can be combined to form a 5- to 7-membered ring optionally having from 1-3 heteroatoms selected from the group consisting of N, O and S; wherein $X^2$ is $C_{1-4}$ alkylene, $C_{1-4}$ heteroalkylene, $C_{2-4}$ alkenylene or $C_{2-4}$ alkynylene; each $R^k$ and $R^L$ is independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-4}$ alkyl, and optionally, $R^k$ and $R^L$ when attached to the same nitrogen atom can be combined to form a five or six-membered ring having from 0 to 2 additional heteroatoms as ring members; each $R^m$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-6}$ alkyl; and the aliphatic portions of $X^2$, $R^k$, $R^L$ and $R^m$ are further substituted with from 0-3 members selected from the group consisting of halogen, $-OH$, $-OR^s$, $-OC(O)NHR^s$, $-OC(O)N(R^s)_2$, $-SH$, $-SR^s$, $-S(O)R^s$, $-S(O)_2R^s$, $-SO_2NH_2$, $-S(O)_2NHR^s$, $-S(O)_2N(R^s)_2$, $-NHS(O)_2R^s$, $-NR^sS(O)_2R^s$, $-C(O)NH_2$, $-C(O)NHR^s$, $-C(O)N(R^s)_2$, $-C(O)R^s$, $-NHC(O)R^s$, $-NR^sC(O)R^s$, $-NHC(O)NH_2$, $-NR^sC(O)NH_2$, $-NR^sC(O)NHR^s$, $-NHC(O)NHR^s$, $-NR^sC(O)N(R^s)_2$, $-NHC(O)N(R^s)_2$, $-CO_2H$, $-CO_2R^s$, $-NHCO_2R^s$, $-NR^sCO_2R^s$, $-CN$, $-NO_2$, $-NH_2$, $-NHR^s$, $-N(R^s)_2$, $-NR^sS(O)NH_2$ and $-NR^sS(O)_2NHR^s$, wherein each $R^s$ is independently an unsubstituted $C_{1-6}$ alkyl, and wherein U is independently selected from the group consisting of $-R^m$, $-CN$, $-CO_2R^k$ and $-NO_2$; and the subscript p is 1.

2. The compound of claim 1, having the formula selected from the group consisting of:

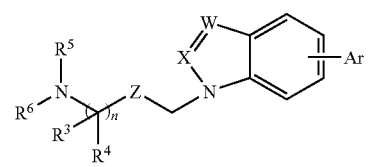

Ib

Ia wherein $R^3$ and $R^4$ at each occurrence are independently selected from the group consisting of hydrogen, halogen and $C_{1-8}$ alkyl;

$R^5$ and $R^6$ are each independently selected from the group consisting of hydrogen, $C_{1-8}$ alkyl, $C_{3-10}$ cycloalkyl, $C_{3-10}$ heterocycloalkyl, $C_{1-8}$ acyl, $C_{1-8}$ alkyl-$S(O)_2-$, aryl, heteroaryl, aryl-$C_{1-6}$ alkyl and aryl-$C_{1-6}$ heteroalkyl;

wherein optionally $R^5$ and $R^6$ are combined to form a 5- to 10-membered ring system having from 1-3 additional heteroatoms selected from the group consisting of N, O and S;

W and X are each independently selected from the group consisting of CH, $CR^8$ and $C(L^1R^8)$;

Z is selected from the group consisting of $-CONR^b-$ and $-NR^bC(O)-$;

the subscript n is an integer from 2-4; and

Ar is an optionally substituted ring system selected from the group consisting of phenyl, pyridyl, pyrimidinyl, benzofuranyl, quinolinyl, isoquinolinyl and indolyl.

3. The compound of claim 2, wherein Ar is a phenyl ring optionally substituted with hydroxy, halogen, cyano, —R$^m$, —NO$_2$, —C(O)NR$^k$R$^L$, —C(O)R$^k$, —NR$^k$S(O)$_2$R$^m$, —NR$^k$R$^L$, —R$^M$, or —NR$^L$(O)R$^k$.

4. The compound of claim 3, wherein Ar is a phenyl ring having the formula:

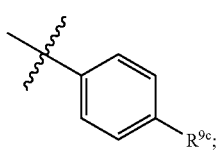

wherein R$^{9c}$ is selected from the group consisting of hydroxy, halogen, cyano, R$^m$, —NO$_2$, —C(O)NR$^k$R$^L$, —C(O)R$^k$, —NR$^k$S(O)$_2$R$^m$, —NR$^k$R$^L$, —OR$^m$, —NR$^L$C(O)R$^k$, —SR$^k$, and —CO$_2$R$^k$.

5. The compound of claim 3, wherein Ar is selected from the group consisting of:

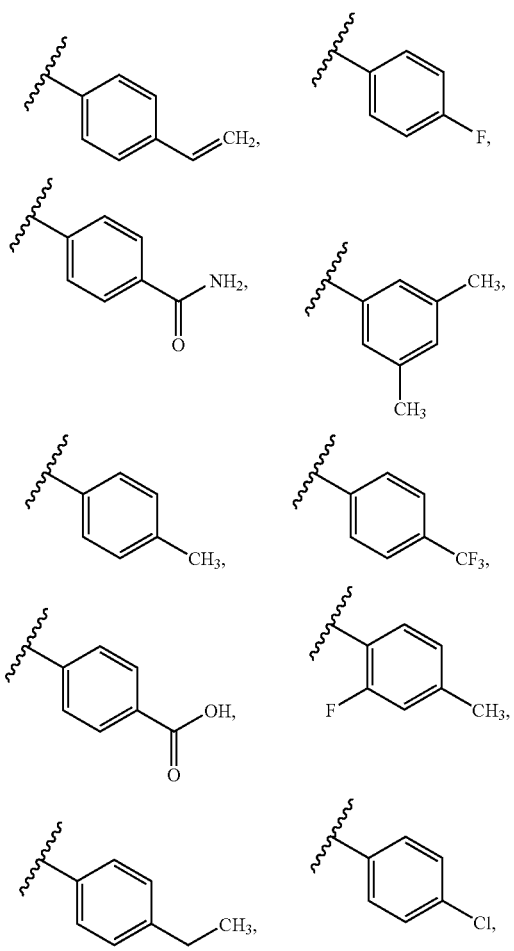

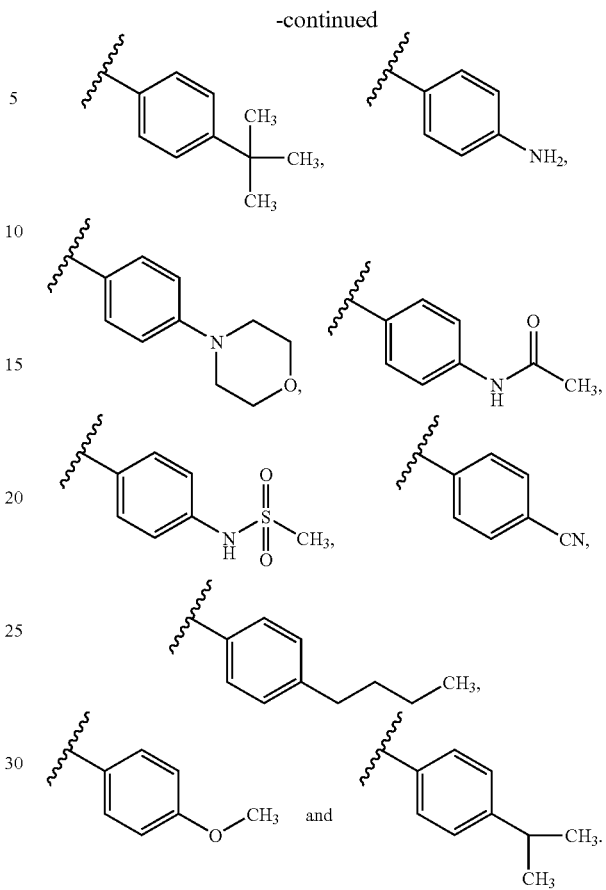

6. The compound of claim 2 wherein the Ar group is attached to the remainder of the molecule at the 6 position of said fused 6- membered aryl, heteroaryl, cycloalkyl or heterocycloalkyl ring.

7. The compound of claim 1, wherein R$^5$ and R$^6$ are each independently selected from the group consisting of hydrogen, C$_{1-8}$ alkyl, C$_{1-8}$ haloalkyl, C$_{2-8}$ alkenyl, C$_{2-8}$ alkynyl and C$_{3-8}$ cycloalkyl; or optionally R$^5$ and R$^6$ are combined to form a 5- to 10-membered heterocycloalkyl ring; and wherein the aliphatic portions of R$^5$ and R$^6$ are substituted with from 0-3 substituents selected from the group consisting of —OH, —OR″, —OC(O)NHR″, —OC(O)N(R″)$_2$, —SH, —S(O)R″, —S(O)$_2$R″, —SO$_2$NH$_2$, —S(O)$_2$NHR″, —S(O)$_2$N(R″)$_2$, —NHS(O)$_2$R″, —NR″S(O)$_2$R″, —C(O)NH$_2$, —C(O)NHR″, —C(O)N(R″)$_2$, —C(O)1e, —NHC(O)R″, —NR″C(O)R″, —NHC(O)NH$_2$, —NR″C(O)NH$_2$, —NR″C(O)NHR″, —NHC(O)NHR″, —NR″C(O)N(R″)$_2$, —NHC(O)N(R″)$_2$, —CO$_2$H, —CO$_2$R″, —NHCO$_2$R″, —NR″CO$_2$R″, —CN, —NO$_2$, —NH$_2$, —NHR″, —N(R″)$_2$, —NR″S(O)NH$_2$ and —NR″S(O)$_2$NHR″.

8. The compound of claim 7, wherein R$^5$ is an optionally substituted member selected from the group consisting of C$_{1-8}$ alkyl, C$_{2-8}$ alkenyl and C$_{2-8}$ alkynyl; and R$^6$ is an optionally substituted C$_{3-10}$ membered cycloalkyl ring.

9. The compound of claim 8, wherein R$^5$ is methyl, ethyl, n-propyl, isopropyl, isobutyl, tert-butyl or n-butyl; and R$^6$ is cyclopentyl, cyclohexyl, cycloheptyl or cyclooctyl.

10. The compound of claim 7, wherein in formula I —NR⁵R⁶ is selected from the group consisting of:
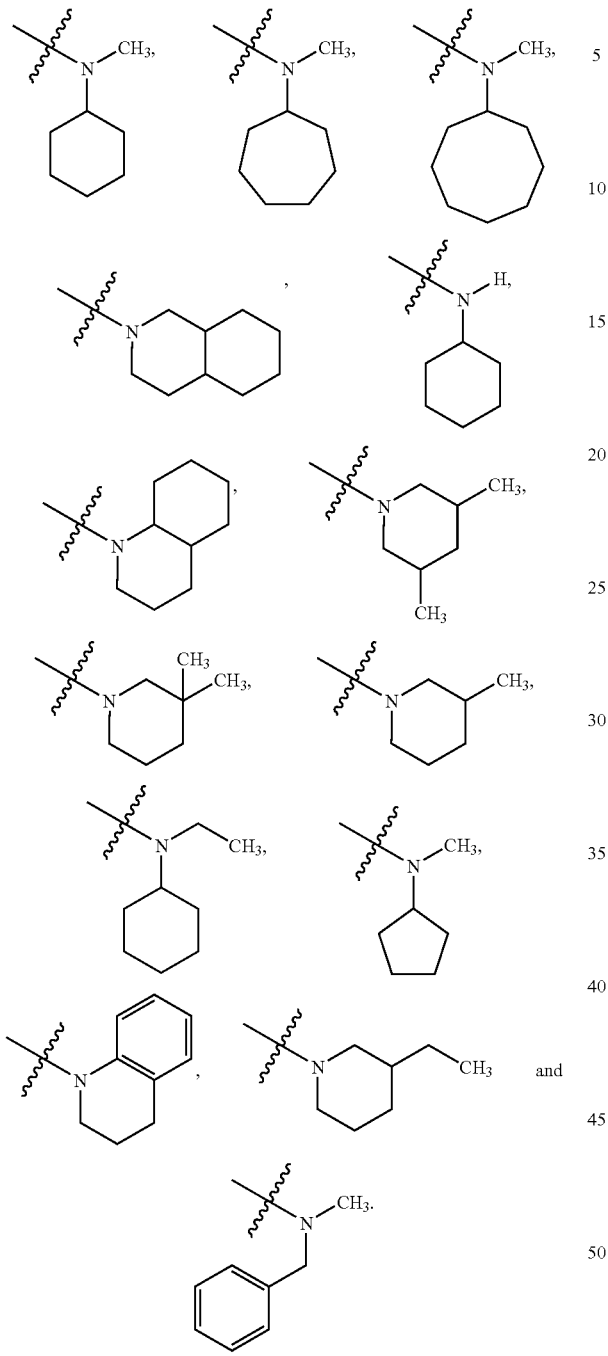
11. The compound of claim 1, wherein R⁵R⁶N—(CR³R⁴)$_n$ Z— is selected from the group consisting of:
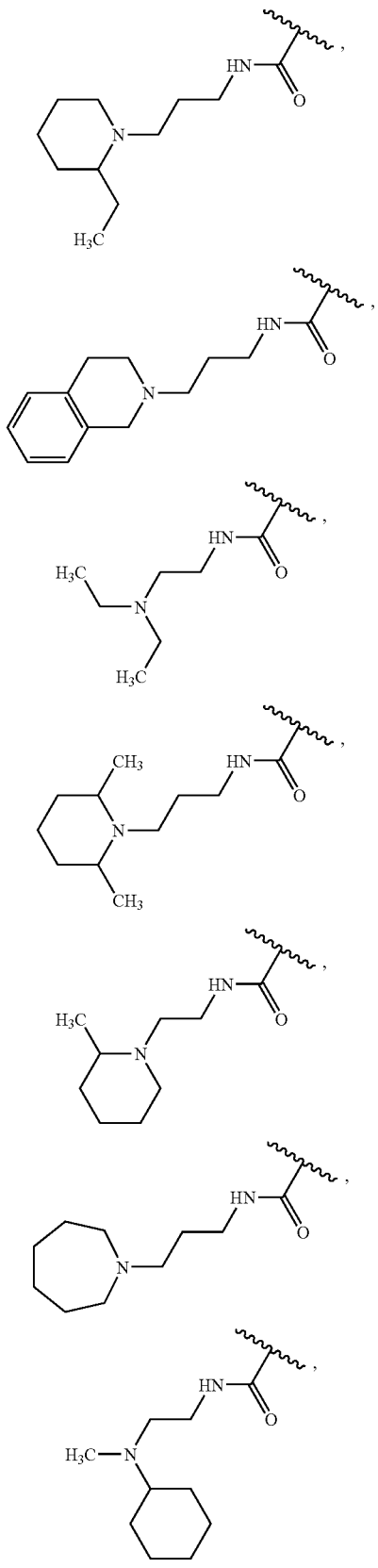

-continued
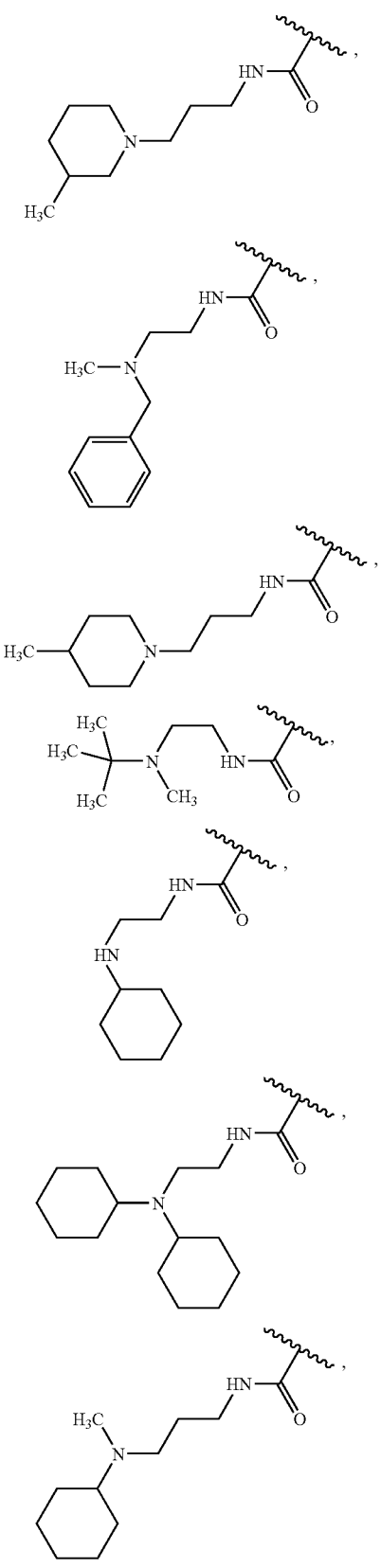
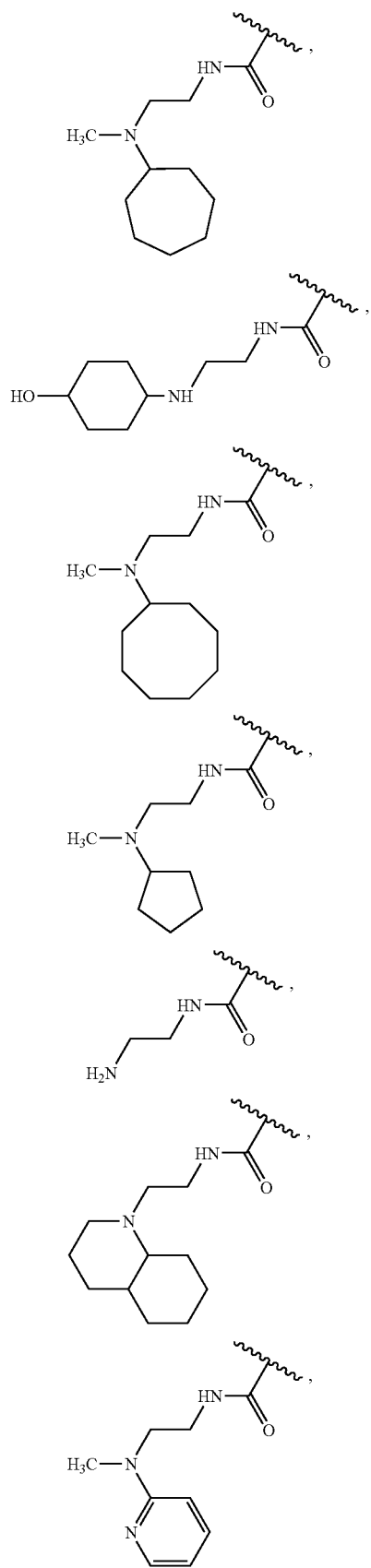

-continued
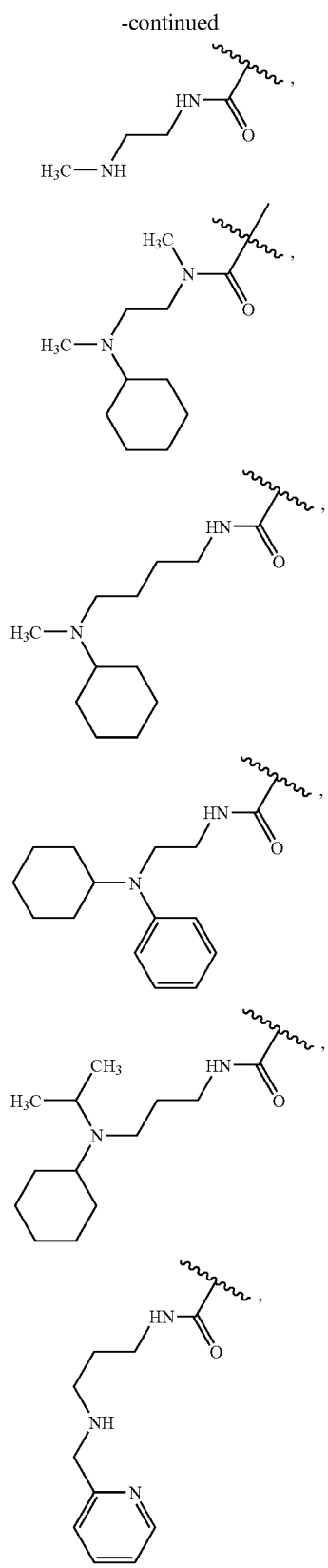
-continued
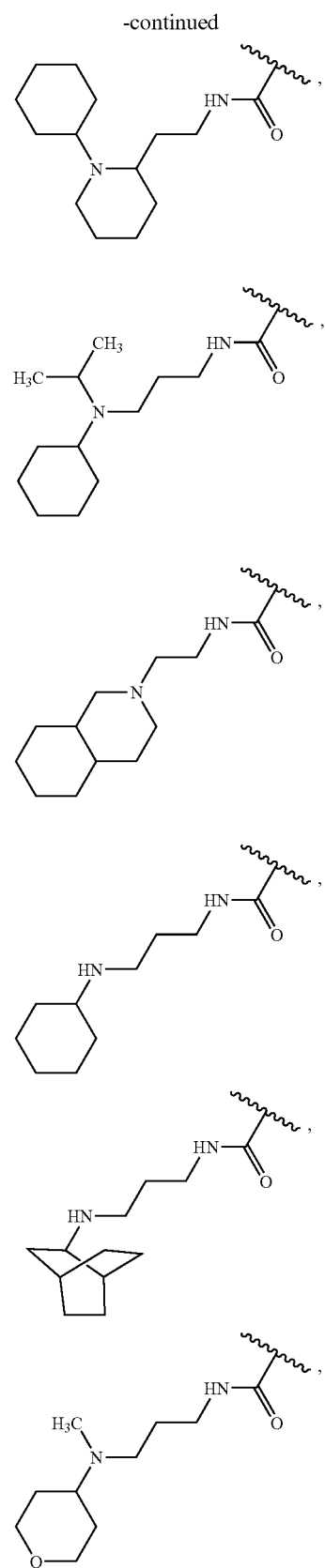

-continued
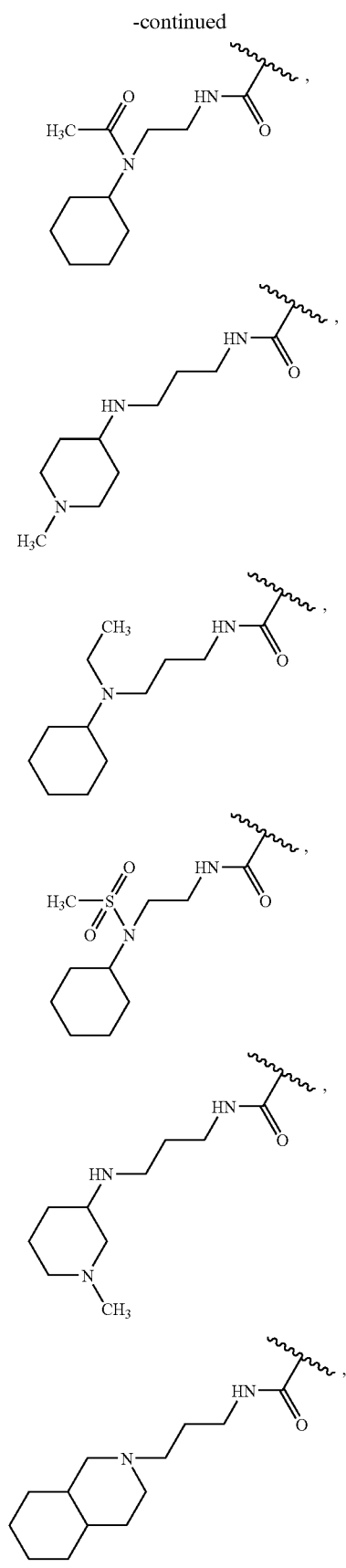
-continued
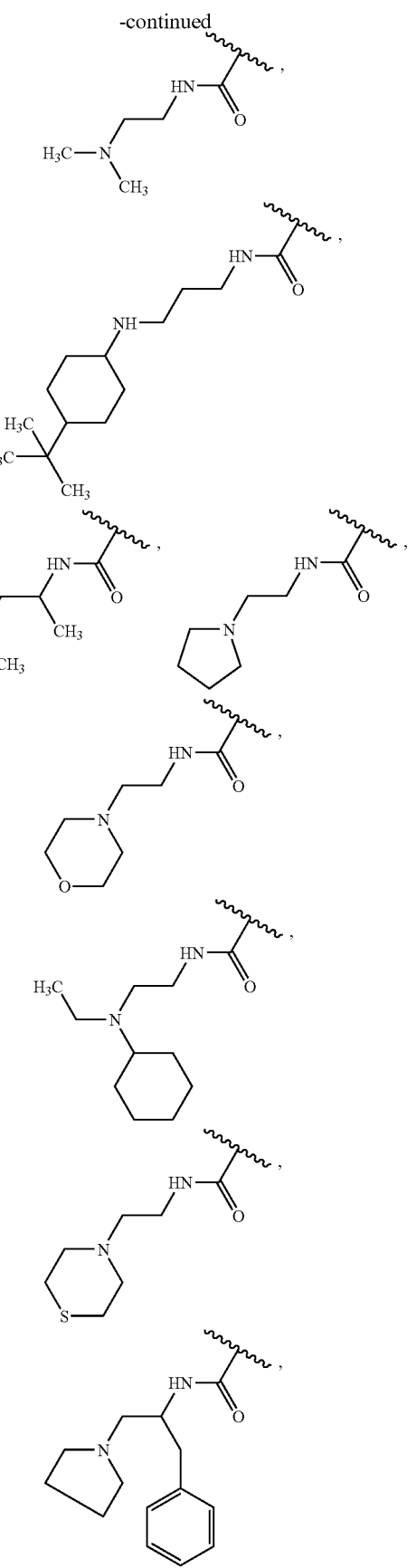

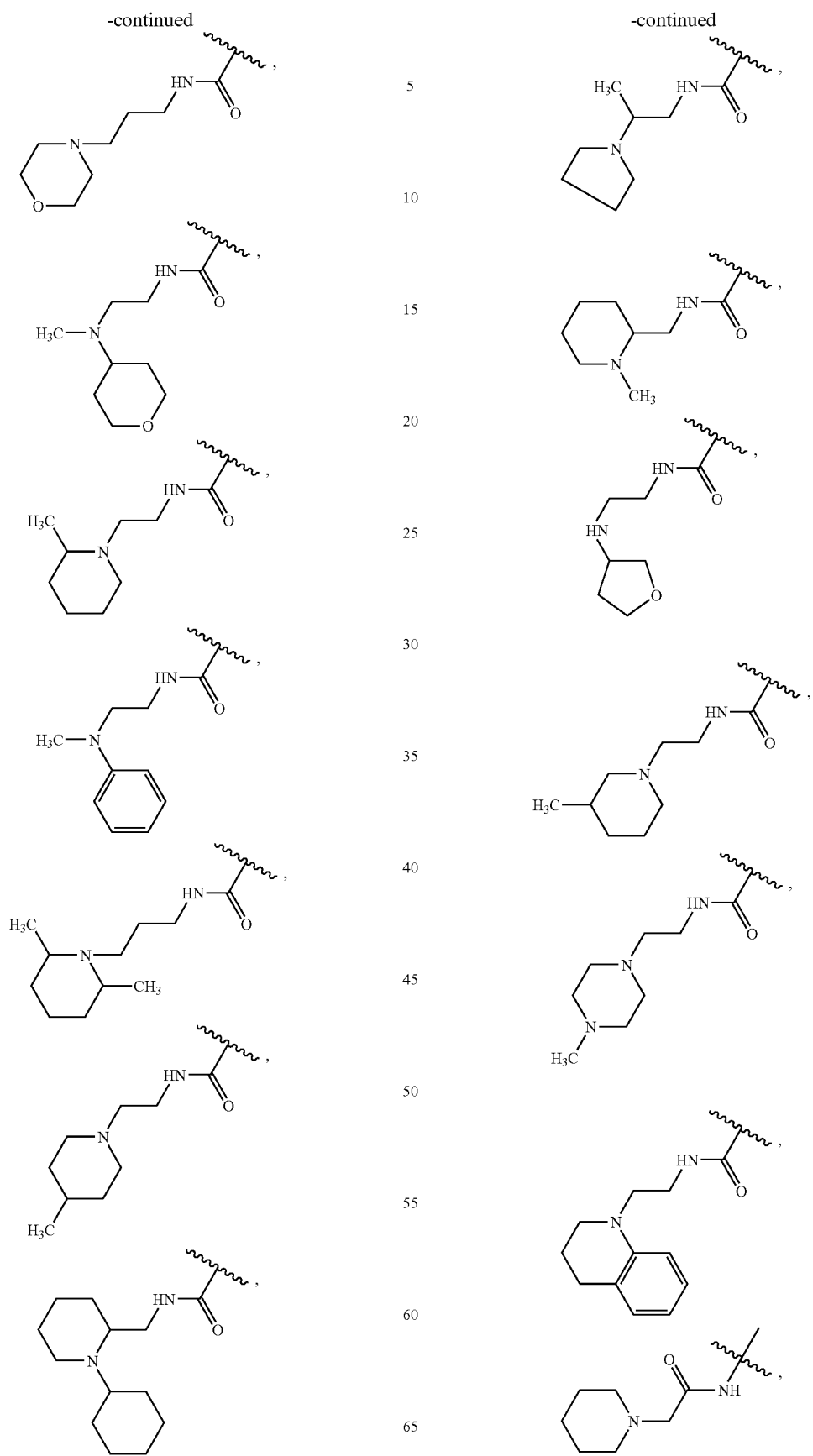

-continued
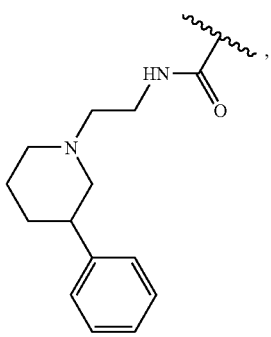
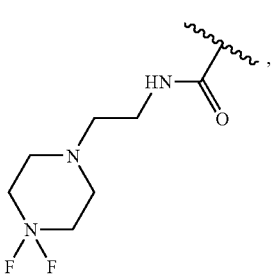
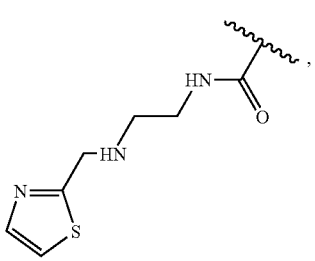
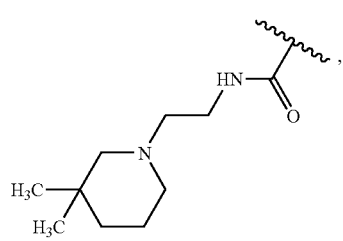
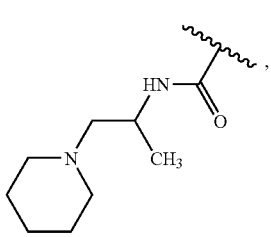
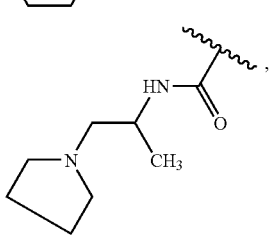
-continued
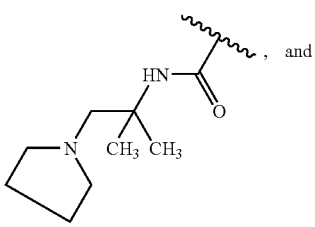
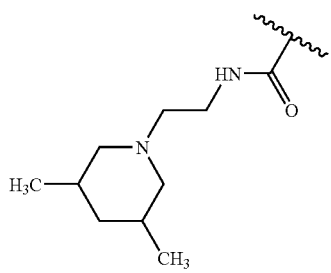
12. A pharmaceutical composition comprising a compound of claim 1 and a pharmaceutically acceptable excipient.
13. The compound of claim 2 —$NR^5R^6$ is selected from the group consisting of
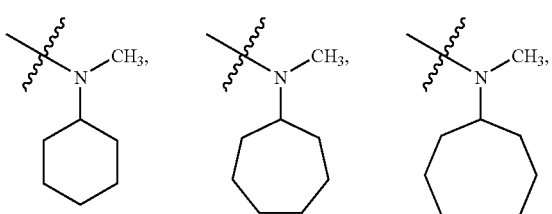
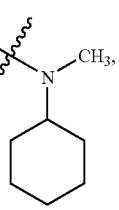 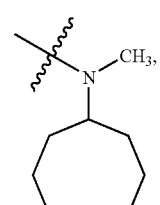
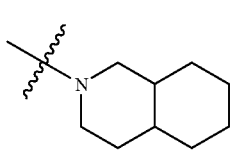 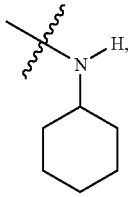
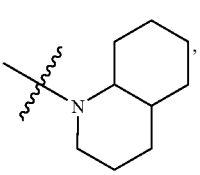 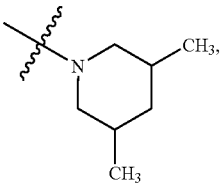
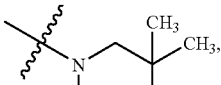 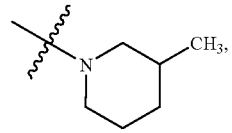
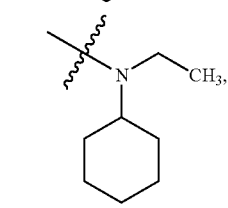 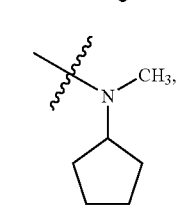

-continued

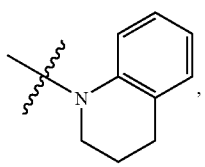 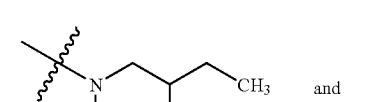 and

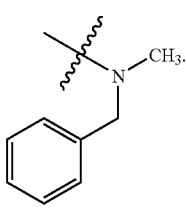

14. The compound of claim 13, wherein Ar is a phenyl ring optionally substituted with hydroxy, halogen, cyano, —$R^m$, —$NO_2$, —$C(O)NR^kR^L$, —$C(O)R^k$, —$NR^kS(O)_2R^m$, —$NR^kR^L$, —$OR^m$, or —$NR^LC(O)R^k$;
  wherein each $R^k$ and $R^L$ is independently selected from the group consisting of hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl and aryl-$C_{1-4}$ alkyl, and optionally, $R^k$ and $R^L$ when attached to the same nitrogen atom can be combined to form a five or six-membered ring having from 0 to 2 additional heteroatoms as ring members;
  each $R^m$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, and aryl-$C_{1-6}$ alkyl; and
  the aliphatic portions of $R^k$, $R^L$ and $R^m$ are further substituted with from 0-3 members selected from the group consisting of halogen, —OH, —$OR^s$, —$OC(O)NHR^s$, —$OC(O)N(R^s)_2$, —SH, —$SR^s$, —$S(O)R^s$, —$S(O)_2R^s$, —$SO_2NH_2$, —$S(O)_2NHR^s$, —$S(O)_2N(R^s)_2$, —$NHS(O)_2R^s$, —$NR^sS(O)_2R^s$, —$C(O)NH_2$, —$C(O)NHR^s$, —$C(O)N(R^s)_2$, —$C(O)R^s$, —$NHC(O)R^s$, —$NR^sC(O)R^s$, —$NHC(O)NH_2$, —$NR^sC(O)NH_2$, —$NR^sC(O)NHR^s$, —$NHC(O)NHR^s$, —$NR^sC(O)N(R^s)_2$, —$NHC(O)N(R^s)_2$, —$CO_2H$, —$CO_2R^s$, —$NHCO_2R^s$, —$NR^sCO_2R^s$, —CN, —$NO_2$, —$NH_2$, —$NHR^s$, —$N(R^s)_2$, —$NR^sS(O)NH_2$ and —$NR^sS(O)_2NHR^s$, wherein each $R^s$ is independently an unsubstituted $C_{1-6}$ alkyl.

15. The compound of claim 14, wherein Ar is a phenyl ring having the formula:

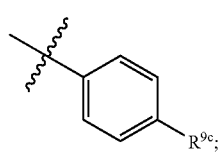

wherein $R^{9e}$ is selected from the group consisting of hydroxy, halogen, cyano, $R^m$—$NO_2$, —$C(O)NR^kR^L$, —$C(O)R^k$, —$NR^kS(O)_2R^m$, —$NR^kR^L$, —$OR^m$, —$NR^LC(O)R^k$, —$SR^k$, and —$CO_2R^k$.

16. The compound of claim 14, wherein Ar is selected from the group consisting of:

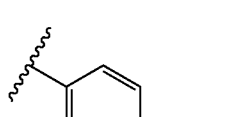 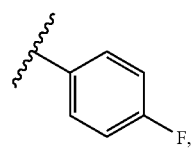

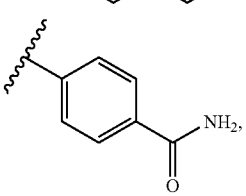 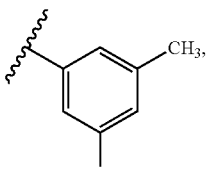

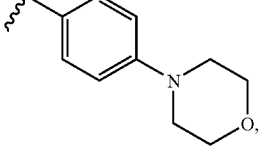 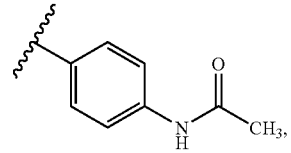

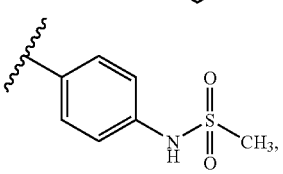 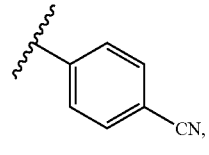

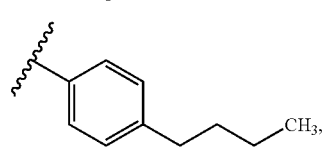

-continued
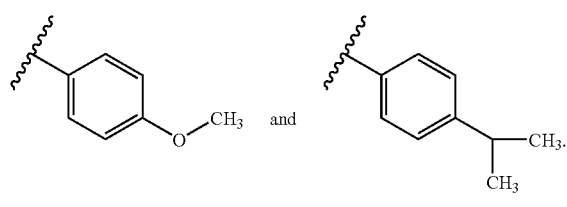 and
17. The compound of claim 13 wherein the Ar group is attached to the remainder of the molecule at the 6 position of said fused 6- membered aryl, heteroaryl, cycloalkyl or heterocycloalkyl ring.
18. The compound of claim 1, wherein the compound has a structure selected from the following formulae:
1
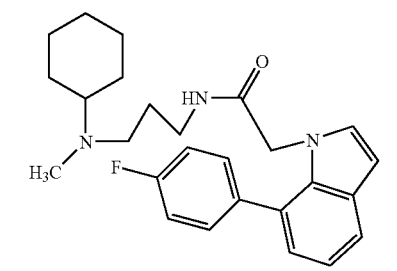
4
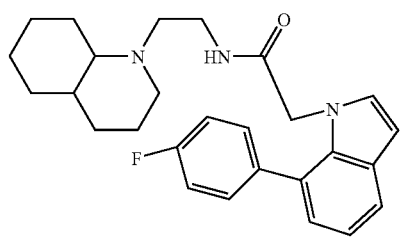
3
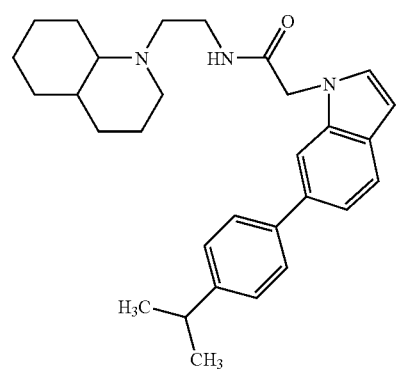
8
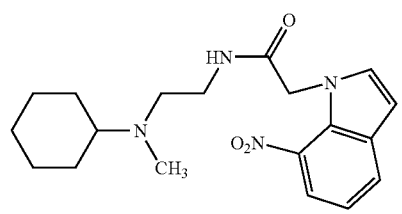
-continued
11
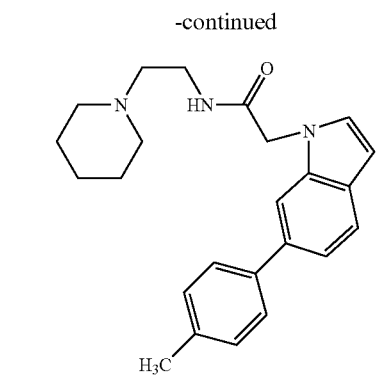
14
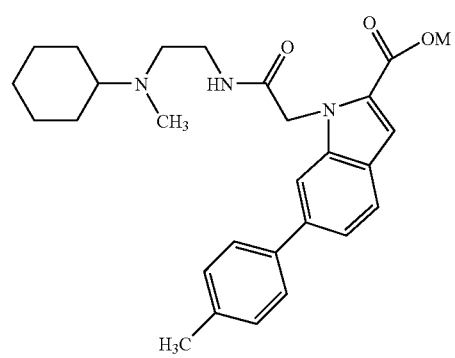
13
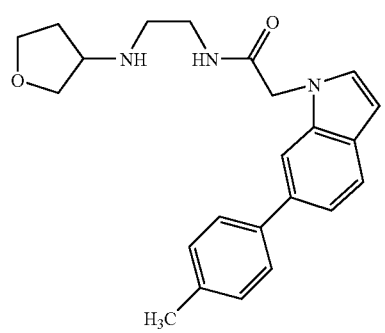
20
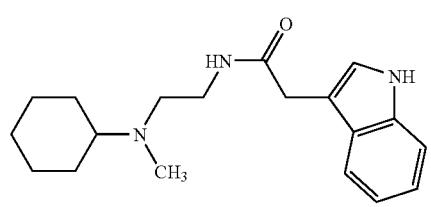
15
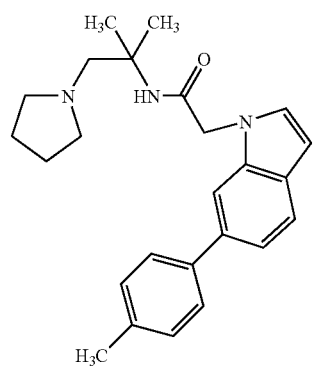

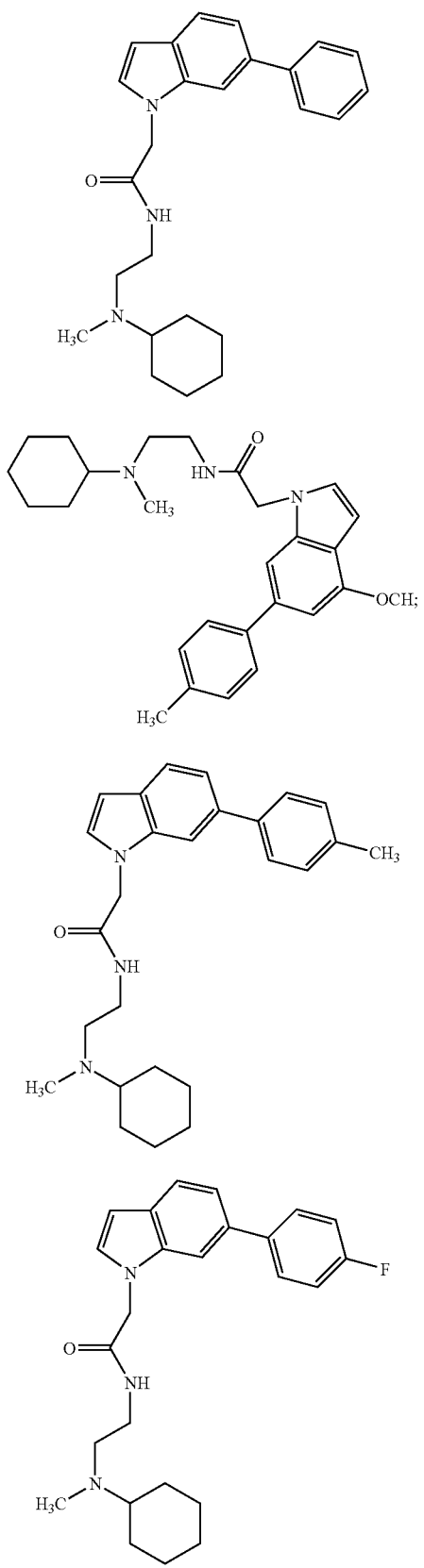
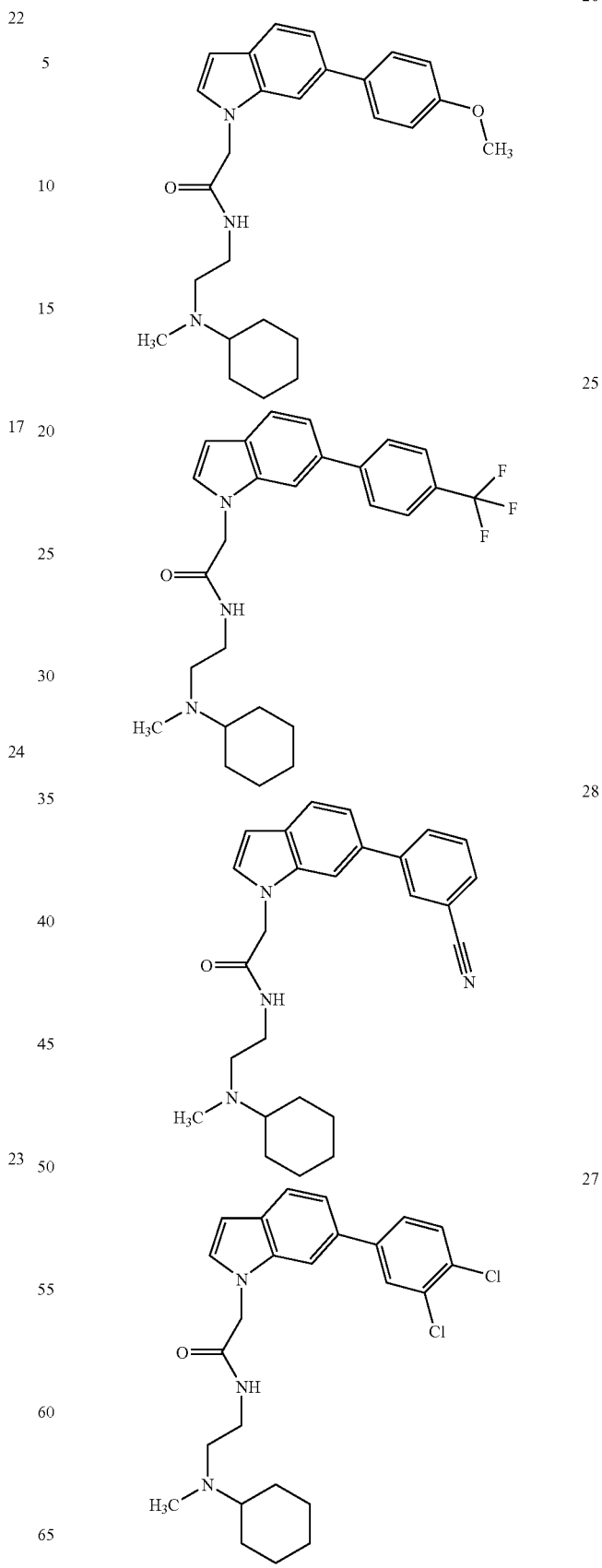

161                                    162
-continued                             -continued
30                                     34
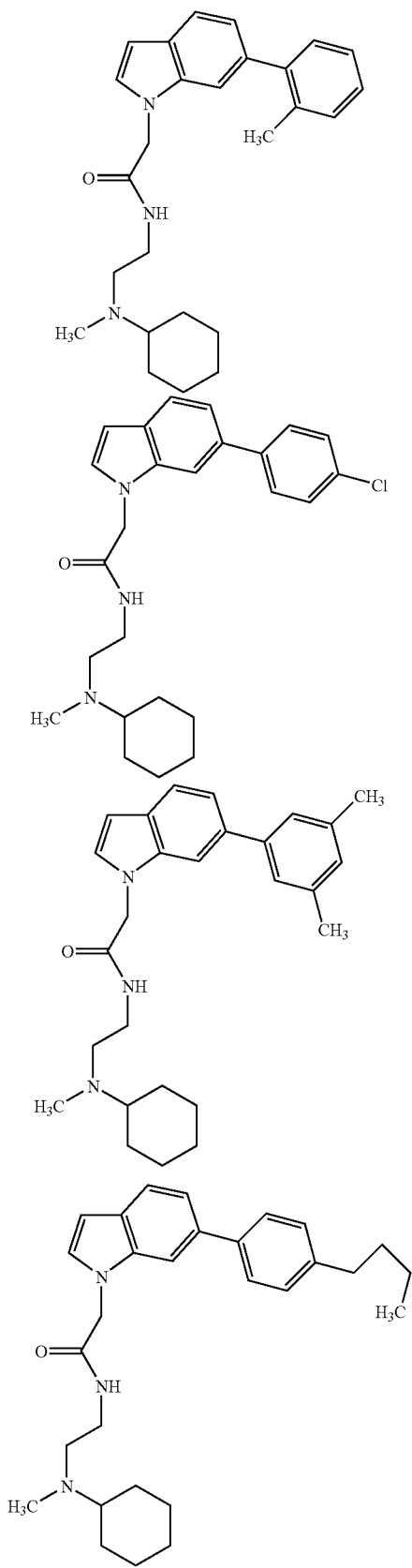
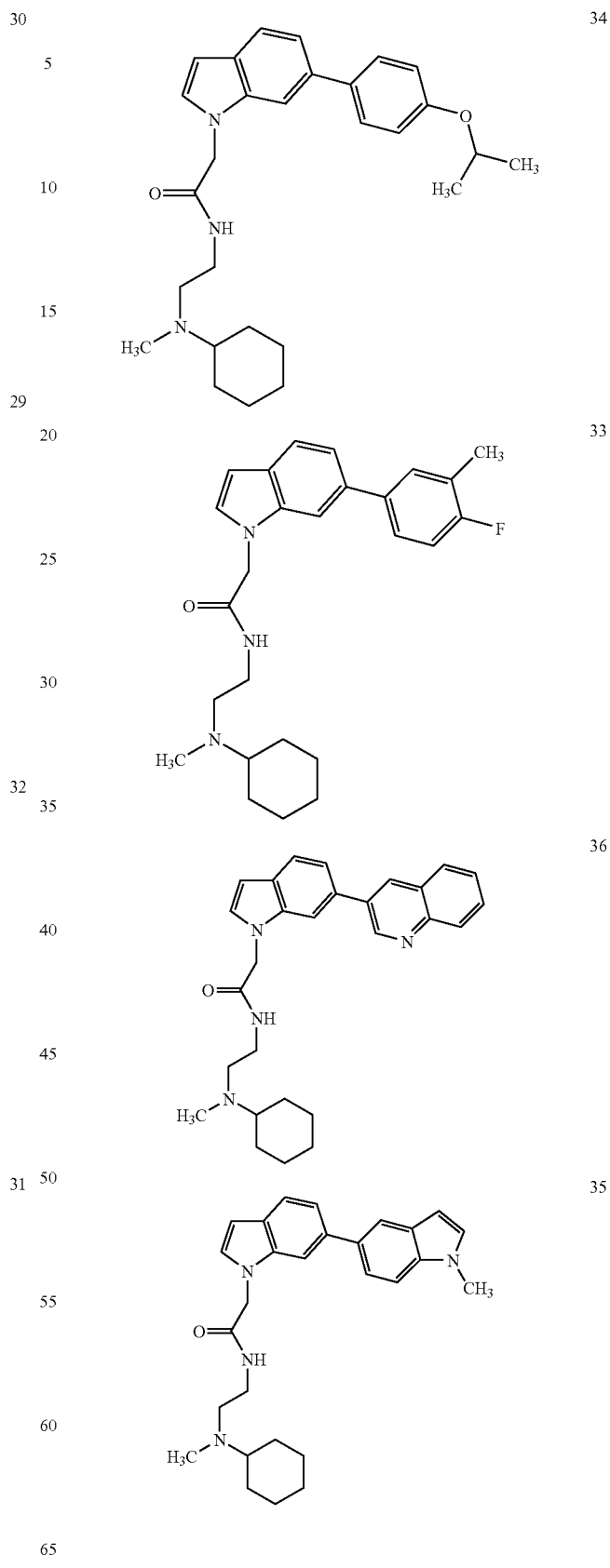

163                                          164
38
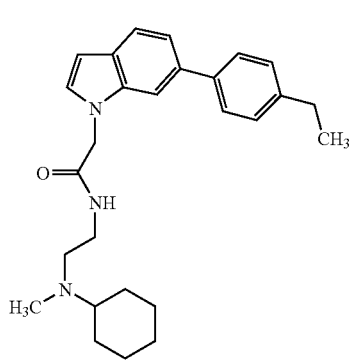
37
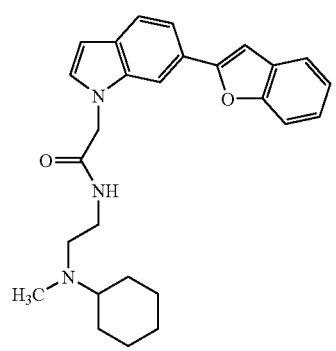
40
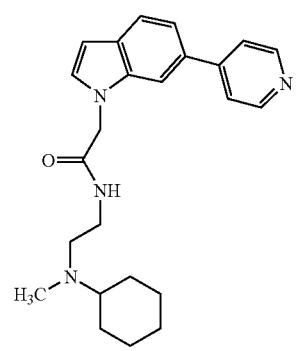
39
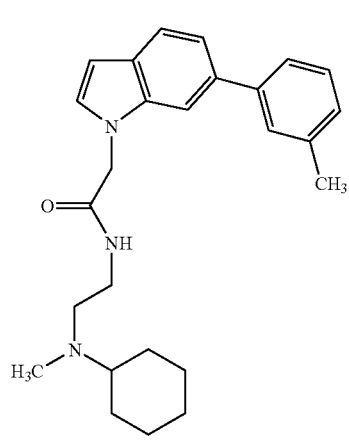
42
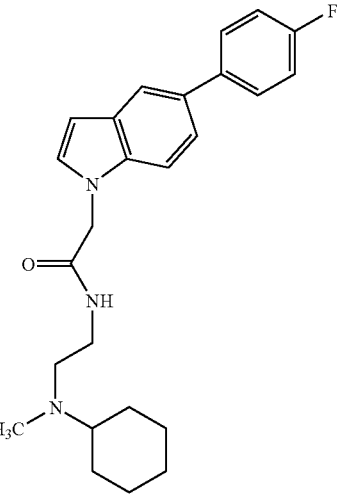
41
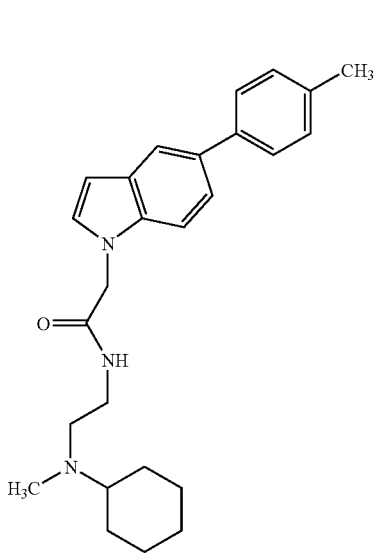
44
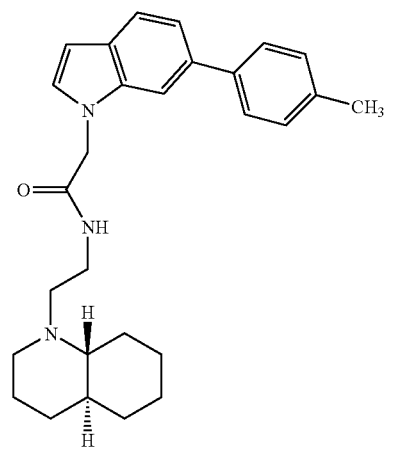

-continued
43
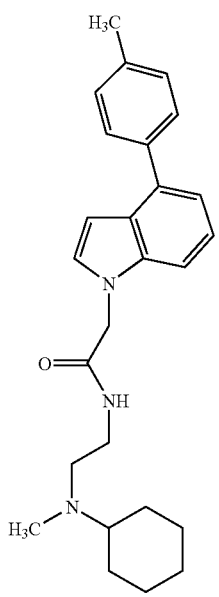
46
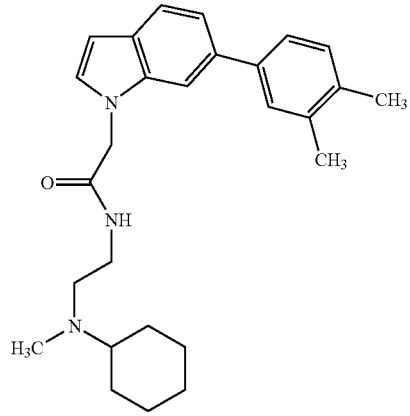
45
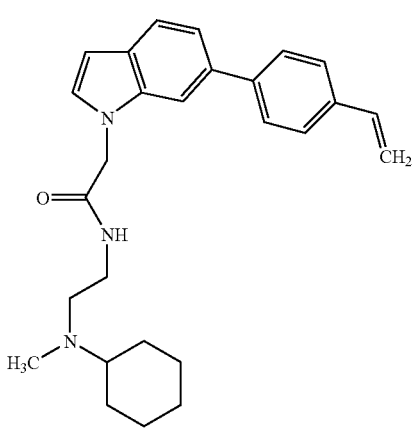
-continued
48
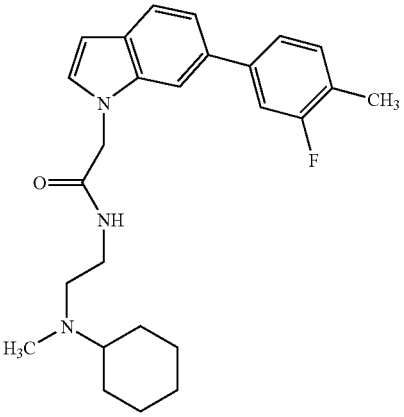
47
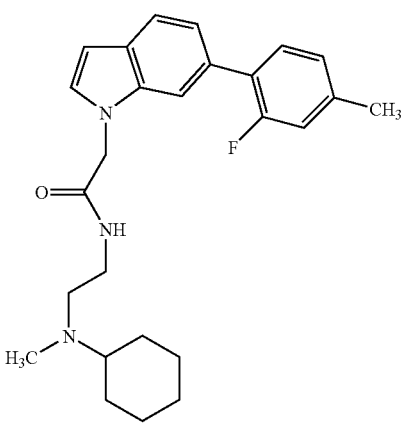
50
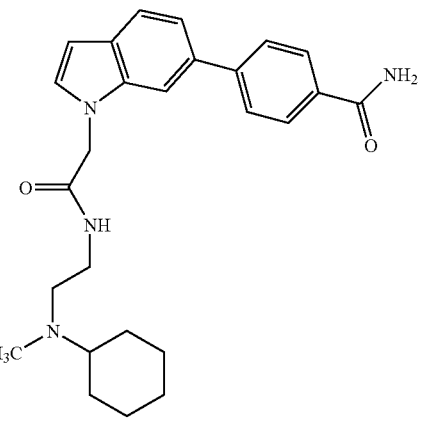

| 51 | 55 |
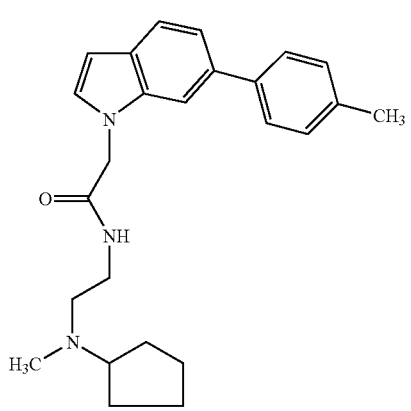
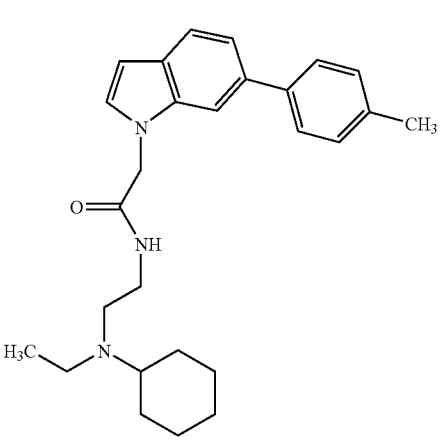
| 52 | |
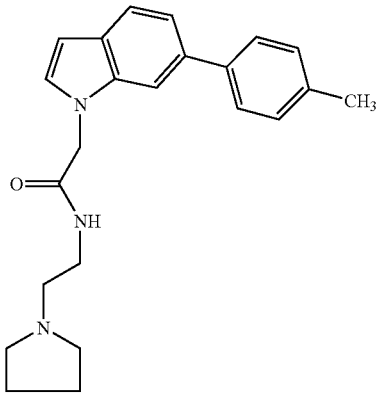
| | 56 |
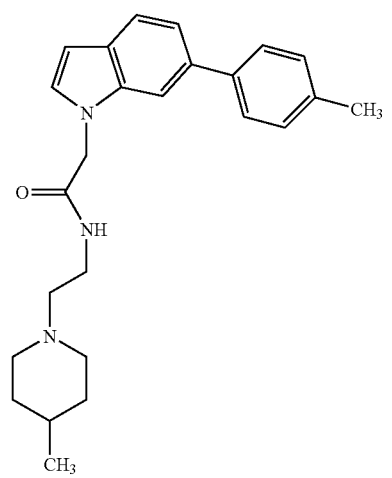
| 53 | |
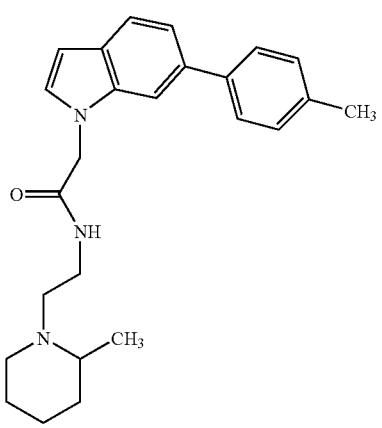
| 54 | 57 |
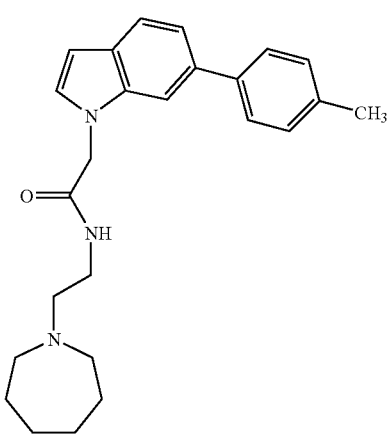
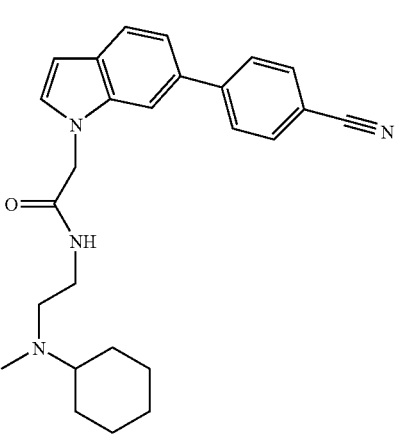

-continued
58
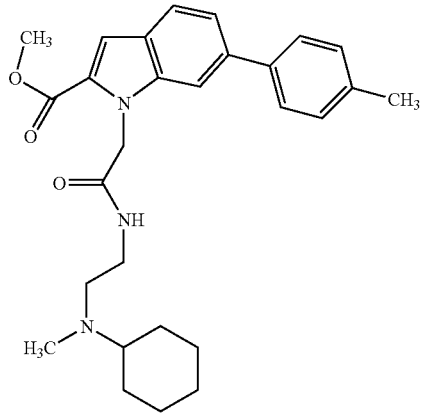
59
62
-continued
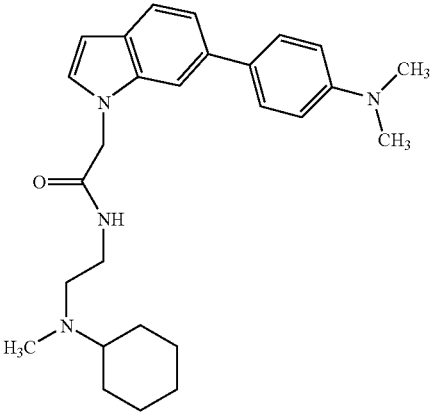
64
* * * * *

UNITED STATES PATENT AND TRADEMARK OFFICE
CERTIFICATE OF CORRECTION

PATENT NO.        : 7,807,704 B2
APPLICATION NO.   : 11/731695
DATED             : October 5, 2010
INVENTOR(S)       : Thomas et al.

It is certified that error appears in the above-identified patent and that said Letters Patent is hereby corrected as shown below:

In the Claims:

Column 138, Claim 1, Line 52: please delete "-$NR^1C(O)$" and replace it with -- -$NR^qC(O)$ --

Column 141, Claim 3, Line 8: please delete "–$R^M$" and replace it with -- -$OR^m$ --

Column 142, Claim 7, Line 50: please insert -- -$SR^n$ -- after "–SH,"

Column 142, Claim 7, Line 53: please delete "-$C(O)1e$" and replace it with -- -$C(O)R^n$ --

Signed and Sealed this
Third Day of July, 2012

David J. Kappos
*Director of the United States Patent and Trademark Office*

SEQUENCE LISTING

<160> NUMBER OF SEQ ID NOS: 12

<210> SEQ ID NO 1
<211> LENGTH: 1089
<212> TYPE: DNA
<213> ORGANISM: Homo sapiens
<220> FEATURE:
<223> OTHER INFORMATION: human chemokine receptor CXCCKR2 (CXCR7, hRDC1)
      coding sequence

<400> SEQUENCE: 1

```
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacacccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa acagggctc   1020 accaagctca tcgatgcctc cagagtctca gagacggagt actctgcctt ggagcagagc   1080
accaaatga                                                          1089
```

<210> SEQ ID NO 2
<211> LENGTH: 362
<212> TYPE: PRT
<213> ORGANISM: Homo sapiens
<220> FEATURE:
<223> OTHER INFORMATION: human chemokine receptor CXCCKR2 (CXCR7, hRDC1)

<400> SEQUENCE: 2

```
Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360
```

<210> SEQ ID NO 3
<211> LENGTH: 1089
<212> TYPE: DNA
<213> ORGANISM: Homo sapiens
<220> FEATURE:
<223> OTHER INFORMATION: human chemokine receptor CXCCKR2.2 (CXCR7, hRDC1) coding sequence

<400> SEQUENCE: 3

```
atggatctgc acctcttcga ctacgccgag ccaggcaact tctcggacat cagctggcca      60
tgcaacagca gcgactgcat cgtggtggac acggtgatgt gtcccaacat gcccaacaaa     120
agcgtcctgc tctacacgct ctccttcatt tacatttttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc ggcattttct tcctcacgtg catgagcgtg     420
gaccgctacc tctccatcac ctacttcacc aacacccccca gcagcaggaa gaagatggta     480
cgccgtgtcg tctgcatcct ggtgtggctg ctggccttct gcgtgtctct gcctgacacc     540
tactacctga gaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa aacgggctc    1020
accaagctca tcgatgcctc cagagtgtcg agacggagt actccgcctt ggagcaaaac    1080
gccaagtga                                                            1089
```

<210> SEQ ID NO 4
<211> LENGTH: 362
<212> TYPE: PRT
<213> ORGANISM: Homo sapiens
<220> FEATURE:
<223> OTHER INFORMATION: human chemokine receptor CXCCKR2.2 (CXCR7, hRDC1)

<400> SEQUENCE: 4

```
Met Asp Leu His Leu Phe Asp Tyr Ala Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45

Phe Ile Tyr Ile Phe Ile Phe Val Ile Gly Met Ile Ala Asn Ser Val
    50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
```

```
                100               105               110
Gly Glu Leu Thr Cys Lys Val Thr His Leu Ile Phe Ser Ile Asn Leu
        115                 120                 125

Phe Ser Gly Ile Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
                180                 185                 190

Glu Thr Tyr Cys Arg Ser Phe Tyr Pro Glu His Ser Ile Lys Glu Trp
            195                 200                 205

Leu Ile Gly Met Glu Leu Val Ser Val Val Leu Gly Phe Ala Val Pro
    210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
                260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
                340                 345                 350

Glu Tyr Ser Ala Leu Glu Gln Asn Ala Lys
        355                 360

<210> SEQ ID NO 5
<211> LENGTH: 1089
<212> TYPE: DNA
<213> ORGANISM: Homo sapiens
<220> FEATURE:
<223> OTHER INFORMATION: human chemokine receptor CXCCKR2.3 (CXCR7,
      hRDC1) coding sequence

<400> SEQUENCE: 5
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacattttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg cctcaccat cccagtctgg     300 gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
```

-continued

```
tactacctga agaccgtcac gtctgcgtcc aacaatgaga cctactgccg gtccttctac    600
cccgagcaca gcatcaagga gtggctgatc ggcatggagc tggtctccgt tgtcttgggc    660
tttgccgttc ccttctccat tgtcgctgtc ttctacttcc tgctggccag agccatctcg    720
gcgtccagtg accaggagaa gcacagcagc cggaagatca tcttctccta cgtggtggtc    780
ttccttgtct gctggttgcc ctaccacgtg gcggtgctgc tggacatctt ctccatcctg    840
cactacatcc ctttcacctg ccggctggag cacgccctct tcacgccct gcatgtcaca     900 cagtgcctgt cgctggtgca ctgctgcgtc aaccctgtcc tctacagctt catcaatcgc    960
aactacaggt acgagctgat gaaggccttc atcttcaagt actcggccaa aacagggctc   1020
accaagctca tcgatgcctc cagagtctca gagacggagt actctgcctt ggagcagagc   1080
accaaatga                                                           1089
```

```
<210> SEQ ID NO 6
<211> LENGTH: 362
<212> TYPE: PRT
<213> ORGANISM: Homo sapiens
<220> FEATURE:
<223> OTHER INFORMATION: human chemokine receptor CXCCKR2.3 (CXCR7,
      hRDC1)

<400> SEQUENCE: 6
```

```
Met Asp Leu His Leu Phe Asp Tyr Ser Glu Pro Gly Asn Phe Ser Asp
 1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Gly Ser Ile Phe Phe Leu Thr Cys Met Ser Val Asp Arg Tyr Leu
    130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
    210                 215                 220

Phe Ser Ile Val Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255
```

```
Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
            325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
            355                 360
```

<210> SEQ ID NO 7
<211> LENGTH: 1089
<212> TYPE: DNA
<213> ORGANISM: Homo sapiens
<220> FEATURE:
<223> OTHER INFORMATION: human chemokine receptor CXCCKR2.4 (CXCR7, hRDC1) coding sequence

<400> SEQUENCE: 7

```
atggatctgc atctcttcga ctactcagag ccagggaact tctcggacat cagctggcca      60
tgcaacagca gcgactgcat cgtggtggac acggtgatgt gtcccaacat gcccaacaaa     120
agcgtcctgc tctacacgct ctccttcatt tacatttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcggc agcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga gaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggctgcc ctaccacgtg gcggtgctgc tggacatctt ctccatcctg     840
cactacatcc ctttcacctg ccggctggag cacgccctct tcacgccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa acagggctc    1020
accaagctca tcgatgcctc cagagtctca gagacggagt actctgcctt ggagcagagc    1080
accaaatga                                                           1089
```

<210> SEQ ID NO 8
<211> LENGTH: 362
<212> TYPE: PRT
<213> ORGANISM: Homo sapiens
<220> FEATURE:
<223> OTHER INFORMATION: human chemokine receptor CXCCKR2.4 (CXCR7, hRDC1)

```
<400> SEQUENCE: 8

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
            115                 120                 125

Phe Gly Ser Ile Phe Phe Leu Thr Cys Met Ser Val Asp Arg Tyr Leu
        130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360

<210> SEQ ID NO 9
<211> LENGTH: 1089
<212> TYPE: DNA
<213> ORGANISM: Homo sapiens
<220> FEATURE:
<223> OTHER INFORMATION: human chemokine receptor CXCCKR2.5 (CXCR7,
      hRDC1) coding sequence
```

-continued

<400> SEQUENCE: 9

```
atggatctgc atctcttcga ctactcagag ccagggaact tctcggacat cagctggccg      60
tgcaacagca gcgactgcat cgtggtggac acggtgatgt gtcccaacat gcccaacaaa     120
agcgtcctgc tctacacgct ctccttcatt tacatttca tcttcgtcat cggcatgatt     180
gccaactccg tggtggtctg ggtgaatatc caggccaaga ccacaggcta tgacacgcac     240
tgctacatct tgaacctggc cattgccgac ctgtgggttg tcctcaccat cccagtctgg     300
gtggtcagtc tcgtgcagca caaccagtgg cccatgggcg agctcacgtg caaagtcaca     360
cacctcatct tctccatcaa cctcttcagc agcattttct tcctcacgtg catgagcgtg     420
gaccgctacc tctccatcac ctacttcacc aacaccccca gcagcaggaa gaagatggta     480
cgccgtgtcg tctgcatcct ggtgtggctg ctggccttct gcgtgtctct gcctgacacc     540
tactacctga agaccgtcac gtctgcgtcc aacaatgaga cctactgccg gtccttctac     600
cccgagcaca gcatcaagga gtggctgatc ggcatggagc tggtctccgt tgtcttgggc     660
tttgccgttc ccttctccat tatcgctgtc ttctacttcc tgctggccag agccatctcg     720
gcgtccagtg accaggagaa gcacagcagc cggaagatca tcttctccta cgtggtggtc     780
ttccttgtct gctggttgcc ctaccacgtg gcggtgctgc tggacatctt ctccatcctg     840
cactacatcc ctttcacctg ccggctggag cacgccctct tcacggccct gcatgtcaca     900
cagtgcctgt cgctggtgca ctgctgcgtc aaccctgtcc tctacagctt catcaatcgc     960
aactacaggt acgagctgat gaaggccttc atcttcaagt actcggccaa acagggctc    1020
accaagctca tcgatgcctc cagagtctca gagacggagt actccgcctt ggagcagagc    1080
accaaatga                                                             1089
```

<210> SEQ ID NO 10
<211> LENGTH: 362
<212> TYPE: PRT
<213> ORGANISM: Homo sapiens
<220> FEATURE:
<223> OTHER INFORMATION: human chemokine receptor CXCCKR2.5 (CXCR7, hRDC1)

<400> SEQUENCE: 10

```
Met Asp Leu His Leu Phe Asp Tyr Ser Glu Pro Gly Asn Phe Ser Asp
  1               5                  10                  15

Ile Ser Trp Pro Cys Asn Ser Ser Asp Cys Ile Val Val Asp Thr Val
             20                  25                  30

Met Cys Pro Asn Met Pro Asn Lys Ser Val Leu Leu Tyr Thr Leu Ser
         35                  40                  45

Phe Ile Tyr Ile Phe Ile Phe Val Ile Gly Met Ile Ala Asn Ser Val
     50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Leu Thr
                 85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
        115                 120                 125

Phe Ser Ser Ile Phe Phe Leu Thr Cys Met Ser Val Asp Arg Tyr Leu
    130                 135                 140
```

-continued

```
Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Val Leu Gly Phe Ala Val Pro
210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
                260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
        290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
                340                 345                 350

Glu Tyr Ser Ala Leu Glu Gln Ser Thr Lys
            355                 360

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:PCR primer
      hRDC1F

<400> SEQUENCE: 11
gaatgcggcc gctatggatc tgcatctctt cgact                              35

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:PCR primer
      hRDC1R

<400> SEQUENCE: 12
gaatgcggcc gctcatttgg tgctctgctc caag                               34
```